(12) United States Patent
Renou et al.

(10) Patent No.: US 9,029,411 B2
(45) Date of Patent: May 12, 2015

(54) THIOPHENES AND USES THEREOF

(75) Inventors: Christelle C. Renou, Stoneham, MA (US); Tricia J. Vos, Medford, MA (US); Matthew O. Duffey, Boston, MA (US); Robert Downham, Newmarket (GB)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 965 days.

(21) Appl. No.: 12/321,871

(22) Filed: Jan. 26, 2009

(65) Prior Publication Data

US 2009/0325925 A1    Dec. 31, 2009

Related U.S. Application Data

(60) Provisional application No. 61/062,439, filed on Jan. 25, 2008.

(51) Int. Cl.
| | | |
|---|---|---|
| *A61K 31/38* | (2006.01) | |
| *C07D 333/36* | (2006.01) | |
| *C07D 409/04* | (2006.01) | |
| *C07D 333/38* | (2006.01) | |
| *C07D 333/40* | (2006.01) | |
| *C07D 409/12* | (2006.01) | |
| *C07D 417/12* | (2006.01) | |

(52) U.S. Cl.
CPC ............ *C07D 409/04* (2013.01); *C07D 333/38* (2013.01); *C07D 333/40* (2013.01); *C07D 409/12* (2013.01); *C07D 417/12* (2013.01)

(58) Field of Classification Search
USPC ............................................ 514/447; 549/68
See application file for complete search history.

(56) References Cited

U.S. PATENT DOCUMENTS

| | | | |
|---|---|---|---|
| 3,257,203 | A | 6/1966 | Sus et al. |
| 3,821,384 | A | 6/1974 | Ariyan et al. |
| 3,852,293 | A | 12/1974 | Ariyan et al. |
| 4,371,607 | A | 2/1983 | Donges |
| 5,134,142 | A | 7/1992 | Matsuo et al. |
| 6,015,826 | A | 1/2000 | Pechacek et al. |
| 6,555,501 | B1 | 4/2003 | Bastiaans et al. |
| 6,608,087 | B1 | 8/2003 | Charifson et al. |
| 6,984,652 | B2 | 1/2006 | Yager et al. |
| 7,074,801 | B1 | 7/2006 | Yoshida et al. |
| 7,405,235 | B2 | 7/2008 | Levy et al. |
| 7,504,513 | B2 | 3/2009 | Boylan et al. |
| 7,511,041 | B2 | 3/2009 | Shimada et al. |
| 7,560,568 | B2 | 7/2009 | Emmitte |
| 7,741,348 | B2 | 6/2010 | Nan et al. |
| 8,183,240 | B2 | 5/2012 | Cardin et al. |
| 8,440,664 | B2 | 5/2013 | Cardin et al. |
| 8,586,582 | B2 | 11/2013 | Liang et al. |
| 8,765,746 | B2 | 7/2014 | Freeze et al. |
| 8,796,268 | B2 | 8/2014 | Freeze et al. |
| 8,796,271 | B2 | 8/2014 | Hirose et al. |
| 2002/0022729 | A1 | 2/2002 | Kawai et al. |
| 2003/0096816 | A1 | 5/2003 | Cao et al. |
| 2004/0116425 | A1 | 6/2004 | Li et al. |
| 2004/0198773 | A1 | 10/2004 | Hart et al. |
| 2004/0248896 | A1 | 12/2004 | Dean et al. |
| 2004/0266751 | A1 | 12/2004 | King |
| 2005/0004122 | A1 | 1/2005 | Brown et al. |
| 2005/0054697 | A1 | 3/2005 | Yager et al. |
| 2005/0124678 | A1 | 6/2005 | Levy et al. |
| 2006/0041006 | A1 * | 2/2006 | Ibrahim et al. ................ 514/422 |
| 2006/0074119 | A1 | 4/2006 | Andrews et al. |
| 2006/0128732 | A1 | 6/2006 | Shimada et al. |
| 2006/0199804 | A1 | 9/2006 | Hummersone et al. |
| 2007/0066666 | A1 | 3/2007 | Emmitte |
| 2007/0142415 | A1 | 6/2007 | Vanotti et al. |
| 2007/0203210 | A1 | 8/2007 | Boylan et al. |
| 2008/0021217 | A1 | 1/2008 | Borchardt et al. |
| 2008/0045570 | A1 | 2/2008 | Brenchley et al. |
| 2008/0132546 | A1 | 6/2008 | Basarab et al. |
| 2008/0255120 | A1 | 10/2008 | Lin et al. |
| 2008/0293716 | A1 | 11/2008 | Drewry et al. |

(Continued)

FOREIGN PATENT DOCUMENTS

| | | |
|---|---|---|
| DE | 275870 A1 | 7/1990 |
| EP | 0853083 A1 | 7/1998 |

(Continued)

OTHER PUBLICATIONS

Rehwald, Matthias et al.., "New Syntheses of 2,4-Diaminothiophenes—Use of (1,3-Oxathiol-2-Ylidene)Malononitrile," *Heterocyles*, vol. 45, No. 3, (1997), pp. 493-500.

Heyde, Cornelia et al., "A Simple Route to N-N-Dialkyl Derivatives of 2-Amino-5-thiophenecarboxylates ," *European Journal of Organic Chemistry*, vol. 19, (2000), pp. 3273-3278.

International Search Report and Written Opinion dated Jun. 10, 2009 from International Application No. PCT/US2009/000513, which relates to U.S. Appl. No. 12/321,871.

"2-Thiophenecarboxylic acid, 3-(4-chlorophenyl)-4-cyano-5-(4-morpholinyl)-(CA Index Name)," CAS Registry No. 883097-33-4, entered May 5, 2006.

"2-Thiophenecarboxylic acid, 3-(4-chlorophenyl)-4-cyano-5-(4-morpholinyl)-, methyl ester (CA Index Name)," CAS Registry No. 882283-38-7, entered Apr. 30, 2006.

(Continued)

*Primary Examiner* — Paul Zarek
(74) *Attorney, Agent, or Firm* — Choate, Hall & Stewart LLP; Andrea L. C. Reid

(57) ABSTRACT

This invention provides thiophene compounds of formula I:

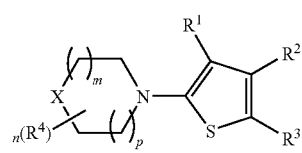

wherein $R^1$, $R^2$, $R^3$, $R^4$, n, p, and m are as described in the specification. The compounds are inhibitors of PI3K and are thus useful for treating proliferative, inflammatory, or cardiovascular disorders.

11 Claims, No Drawings

(56) References Cited

U.S. PATENT DOCUMENTS

| | | |
|---|---|---|
| 2008/0306060 A1 | 12/2008 | Alexander et al. |
| 2008/0306121 A1 | 12/2008 | Nan et al. |
| 2009/0012031 A1 | 1/2009 | Chinnaiyan et al. |
| 2009/0030016 A1 | 1/2009 | Gandhi et al. |
| 2009/0036435 A1 | 2/2009 | Curry et al. |
| 2009/0247567 A1 | 10/2009 | Do et al. |
| 2010/0075951 A1 | 3/2010 | Cardin et al. |
| 2010/0130473 A1 | 5/2010 | Hummersone et al. |
| 2010/0256172 A1 | 10/2010 | Shi et al. |
| 2010/0267759 A1 | 10/2010 | Seefeld et al. |
| 2011/0003806 A1 | 1/2011 | Hirose et al. |
| 2011/0003807 A1 | 1/2011 | Banno et al. |
| 2011/0021531 A1 | 1/2011 | Chobanian et al. |
| 2012/0142732 A1 | 6/2012 | Cullis et al. |
| 2012/0172345 A1 | 7/2012 | Freeze et al. |
| 2012/0178723 A1 | 7/2012 | Hirose et al. |
| 2012/0214794 A1 | 8/2012 | Freeze et al. |
| 2013/0165464 A1 | 6/2013 | Chau et al. |
| 2013/0165472 A1 | 6/2013 | Chau et al. |
| 2013/0165483 A1 | 6/2013 | Chau et al. |
| 2013/0217689 A1 | 8/2013 | Cardin et al. |
| 2013/0267563 A1 | 10/2013 | Hirose et al. |

FOREIGN PATENT DOCUMENTS

| | | |
|---|---|---|
| GB | 874634 A | 8/1961 |
| JP | 10087490 | 4/1998 |
| JP | 2007-197324 A | 8/2007 |
| WO | WO-97/12615 A1 | 4/1997 |
| WO | WO-98/08845 A1 | 3/1998 |
| WO | WO-98/47894 A1 | 10/1998 |
| WO | WO-00/02871 A1 | 1/2000 |
| WO | WO-00/35912 A1 | 6/2000 |
| WO | WO-00/63204 A2 | 10/2000 |
| WO | WO-02/088107 A1 | 11/2002 |
| WO | WO-03/015776 A1 | 2/2003 |
| WO | WO-03/027085 A2 | 4/2003 |
| WO | WO-03/027107 A1 | 4/2003 |
| WO | WO-03/040096 A2 | 5/2003 |
| WO | WO-2004/016592 A1 | 2/2004 |
| WO | WO-2004/016741 A2 | 2/2004 |
| WO | WO-2004/096797 A1 | 11/2004 |
| WO | WO-2006/046031 A1 | 5/2006 |
| WO | WO-2006/068933 A2 | 6/2006 |
| WO | WO-2006/069063 A1 | 6/2006 |
| WO | WO 2006/078287 A2 | 7/2006 |
| WO | WO-2006/102194 A1 | 9/2006 |
| WO | WO-2006/114313 A1 | 11/2006 |
| WO | WO-2007/002559 A1 | 1/2007 |
| WO | WO-2007/043400 A1 | 4/2007 |
| WO | WO-2007/087488 A2 | 8/2007 |
| WO | WO-2007/096315 A1 | 8/2007 |
| WO | WO-2007/110344 A1 | 10/2007 |
| WO | WO 2007/129044 A1 | 11/2007 |
| WO | WO 2007/129161 A2 | 11/2007 |
| WO | WO-2007/138110 A2 | 12/2007 |
| WO | WO-2008/014238 A2 | 1/2008 |
| WO | WO-2008/021235 A2 | 2/2008 |
| WO | WO-2008/023159 A1 | 2/2008 |
| WO | WO-2008/024980 A2 | 2/2008 |
| WO | WO-2008/036541 A1 | 3/2008 |
| WO | WO-2008/047109 A1 | 4/2008 |
| WO | WO-2008/083070 A1 | 7/2008 |
| WO | WO-2008/090382 A1 | 7/2008 |
| WO | WO-2008/097835 A2 | 8/2008 |
| WO | WO-2008/098105 A1 | 8/2008 |
| WO | WO-2008/134679 A1 | 11/2008 |
| WO | WO-2008/139161 A1 | 11/2008 |
| WO | WO-2008/157273 A1 | 12/2008 |
| WO | WO-2009/040730 A2 | 4/2009 |
| WO | WO-2009/042607 A1 | 4/2009 |
| WO | WO-2009/049028 A1 | 4/2009 |
| WO | WO-2009/094224 A1 | 7/2009 |
| WO | WO-2009/106885 A1 | 9/2009 |
| WO | WO-2009/122148 A1 | 10/2009 |
| WO | WO-2009/154741 A1 | 12/2009 |
| WO | WO-2009/158374 A2 | 12/2009 |
| WO | WO-2010/001126 A1 | 1/2010 |
| WO | WO-2010/005841 A1 | 1/2010 |
| WO | WO-2010/017079 A1 | 2/2010 |
| WO | WO-2010/055304 A2 | 5/2010 |
| WO | WO-2010/071741 A1 | 6/2010 |
| WO | WO-2010/080873 A1 | 7/2010 |
| WO | WO-2010/090716 A1 | 8/2010 |
| WO | WO-2010/121675 A2 | 10/2010 |
| WO | WO-2010/132598 A1 | 11/2010 |
| WO | WO-2011/043371 A1 | 4/2011 |

OTHER PUBLICATIONS

Pinto, Ivan L. et al., "The Synthesis of 5-alkoxy and 5-amino Substituted Thiophenes," *Tetrahedron Letters*, vol. 41, No. 10, (2000), pp. 1597-1600.

Hirai, Kentaro et al., "Heterocyclic Cation Systems. 14. Synthesis of Thieno[3,2-e][1,4]diazepine, Thiazolo[4,5-e][1,4]diazepine, and s-Triazolo[3,4-c]thiazolo[4,5-e][1,4]diazepine Derivatives," *Journal of Organic Chemistry*, vol. 45, (1980), pp. 253-260.

Datta, A. et al., "A Novel Route to Methyl 3-3(3,4-Disubstituted 5-alkylthio/amino-2-thienyl) propenoates," *Synthesis*, vol. 7, (1988), pp. 556-567.

Raap, R., "Some Synthesis With Dimethyl Monothionemalonate," *Canadian Journal of Chemistry*, vol. 46, No. 13, (1968), pp. 2255-2261.

Hirai, Kentaro et al., "Novel Synthesis of Thiophene Derivatives from 1,3-Oxathiol-2-ylideneimmonium Salt," *Chemical & Pharmaceutical Bulletin*, vol. 19, No. 10, (1971), pp. 2194-2197.

1,2,4-Oxadiazole, 5-[5-(1H-imidazol-2-yl)-2-thienyl]-3-(methoxymethyl)-(CA Index Name), CAS Registry No. 1069660-66-7, entered Nov. 2, 2008.

1,2,4-Oxadiazole-3-ethanamine, 5-[5-(1H-imidazol-2-yl)-2-thienyl]-N,N-dimethyl- (CA Index Name), CAS Registry No. 1066888-52-5, entered Oct. 27, 2008.

1H-Pyrazole-1-carboxylic acid, 5-[2,2'-bithiophen]-5-yl-, ethyl ester (CA Index Name), CAS Registry No. 957595-63-0, entered Dec. 12, 2007.

2,7-Naphthyridine, 1,2,3,4-tetrahydro-5-[5-[5-(1H-imidazol-2-yl)-2-thienyl]-1,2,4-oxadiazol-3-yl]-6-methyl- (CA Index Name), CAS Registry No. 1069717-72-1, entered Nov. 2, 2008.

2-Thiazolamine, 4-[5-(2H-tetrazol-5-yl)-2-thienyl]- (CA Index Name), CAS Registry No. 937625-84-8, entered Jun. 17, 2007.

3H-1,2,4-Triazole-3-thione, 2,4-dihydro-4-methyl-5-[4-methyl-2-(5-methyl-3-isoxazolyl)-5-thiazolyl]-(CA Index Name), CAS Registry No. 264616-86-6, entered May 12, 2000.

4-Oxazolecarboxylic acid, 5-[(ethoxymethylene)amino]-2-(4-pyridinyl)-, ethyl ester- (CA Index Name), CAS Registry No. 885901-22-4, entered May 29, 2006.

4-Thiazolecarboxamide, 2-(4-acetyl-5-methyl-1H-1,2,3-triazol-1-yl)-N,N-diethyl-5-phenyl- (CA Index Name), CAS Registry No. 709639-21-4, entered Jul. 14, 2004.

Abdelrazek et al., Heterocyclic Synthesis with Nitriles: Synthesis of Some Novel Thiophene and Thieno[2,3-d]Pyrimidine Derivatives, Phosphorus, Sulfur, and Silicon, 71:93-97 (1992).

Acetamide, N-(3,5-dichlorophenyl)-2-[[4-methyl-5-[4-methyl-2-(5-methyl-3-isoxazolyl)-5-thiazolyl]-4H-1,2,4-triazol-3-yl]thio]- (CA Index Name), CAS Registry No. 264626-19-9, entered May 12, 2000.

Acetamide, N-(4-chlorophenyl)-2-[[4-methyl-5-[4-methyl-2-(5-methyl-3-isoxazolyl)-5-thiazolyl]-4H-1,2,4-triazol-3-yl]thio]-(CA Index Name), CAS Registry No. 264626-21-3, entered May 12, 2000.

Adib, M. et al., Facile One-Pot Three-Component Synthesis of Functionalized Pyridylfuran-2-amines, Helvetica Chimica Acta, 89(2):299-303 (2006).

Al-Azawe et al., Synthesis of 2,5-Disubstituted Thiazoles and Their Reactions with Grignard Reagents, Journal of the Iraqi Chemical Society, 13(1): 1-13 (1988).

Batista et al., Synthesis and characterization of new thienylpyrrolyl-benzothiazoles as efficient and thermally stable nonlinear optical chromophores, Tetrahedron, 63(20):4258-4265 (2007).

(56) References Cited

OTHER PUBLICATIONS

Batista et al., Synthesis and Second-Order Nonlinear Optical Properties of New Chromophores Containing Benzimidazole, Thiophene, and Pyrrole Heterocycles, Tetrahedron, 63(39): 9842-9849 (2007).
Benzamide, N,N'-(4,4'-di-2-thienyl[2,2'-bithiazole]-5,5'-diyl)bis- (CA Index Name) CAS Registry No. 691381-57-4, entered Jun. 10, 2004.
Benzamide, N,N'-[4,4'-bis(4-fluorophenyl)[2,2'-bithiazole]-5,5'-diyl]bis[4-methyl- (CA Index Name) CAS Registry No. 691381-60-9, entered Jun. 10, 2004.
Benzamide, N-(4'-amino-2',3'-dihydro-3',4-diphenyl-2'-thioxo[2,5'-bithiazol]-5-yl)- (CA Index Name)CAS Registry No. 879910-33-5, entered Apr. 10, 2006.
Benzamide, N-[2-(5-amino-1-phenyl-1H-pyrazol-4-yl)-4-phenyl-5-thiazolyl]-4-methyl- (CA Index Name), CAS Registry No. 1017527-68-2, entered Apr. 27, 2008.
Berndt, A. et al., The p110δ crystal structure uncovers mechanisms for selectivity and potency of novel PI3K inhibitors, Nature Chemical Biology, 6(2):117-124 (2010).
Boppana, K. et al., Knowledge based identification of MAO-B selective inhibitors using pharmacophore and structure based virtual screening models, European Journal of Medicinal Chemistry, 44:3584-3590 (2009).
Carbamic acid, N,N'-(4,4'-di-2-thienyl[2,2'-bithiazole]-5,5'-diyl)bis-,C,C'-dimethyl ester (CA Index Name) CAS Registry No. 691381-58-5, entered Jun. 10, 2004.
Carbamic acid,4,4'-diphenyl[2,2'-bithiazole]-5,5'-diyl)bis-, dimethyl ester (9CI)(CA Index Name), CAS Registry No. 505060-78-6, entered Apr. 25, 2003.
Chattopadhyay, S. K. et al., Efficient Construction of the Carbon Skeleton of the Novel Polyoxazole-Based Cyclopeptide IB-01211 via a Biomimetic Macrocyclisation,Synlett, 4:555-558 (2010).
Choi, W. et al., Synthesis and Antiproliferative Activities of 1-Substituted-3-(3-chloro-5-methoxyphenyl)-4-pyridinylpyrazole Derivatives Against Melanoma Cell Line, Bulletin of the Korean Chemical Society, 30(9):2027-2031 (2009).
Cudworth et al., Structure-Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).
Database CAS Registry (Columbus, Ohio), RN 893689-50-4 (Entered Jul. 17, 2006).
Database CAS Registry (Columbus, Ohio), RN 893692-42-7 (Entered Jul. 17, 2006).
Database CAS Registry (Columbus, Ohio), RN 893704-20-6 (Entered Jul. 17, 2006).
Database CAS Registry (Columbus, Ohio), RN 893705-40-3 (Entered Jul. 17, 2006).
Database CAS Registry (Columbus, Ohio), RN 898517-78-7 (Entered Aug. 3, 2006).
Emmitte et al., Discovery of Thiophene Inhibitors of Polo-like Kinase, Bioorganic & Medicinal Chemistry Letters, 19(3): 1018-1021 (2009).
Fletcher, A. N. et al., Laser Dye Stability, Part 12. The Pyridinium Salts, Applied Physics, B43:155-160 (1987).
Fridman et al., Spectroscopy, Photophysical and Photochemical Properties of Bisimidazole, Derivatives, Journal of Photochemistry and Photobiology, A: Chemistry, 188(1): 25-33 (2007).
Golub, T.R. et al., Molecular classification of cancer: class discovery and class prediction by gene expression monitoring, Science, 286(5439):531-7 (1999).
Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).
Hernandez, D. et al., Synthesis and Antitumor Activity of Mechercharmycin A Analogues, Journal of Medicinal Chemistry, 51: 5722-5730 (2008).
Hernandez, D. et al., Synthesis of Natural Product Derivatives Containing 2,4-Concatenated Oxazoles, European Journal of Organic Chemistry, (19): 3389-3396 (2008).

Imidazo[1,2-a]pyridine, 6-[3-[5-(2H-tetrazol-5-yl)-2-thienyl]-1H-pyrazol-4-yl]-3-(2-thiazolyl)-(CA Index Name) CAS Registry No. 732241-18-8, entered Aug. 25, 2004).
International Search Report for PCT-US09-03607, 4 pages (Sep. 23, 2009).
International Search Report for PCT-US10-00234, 3 pages (Jun. 1, 2010).
International Search Report for PCT-US11-47245, 2 pages (Dec. 22, 2011).
International Search Report for PCT-US11-47407, 2 pages (Dec. 22, 2011).
International Search Report for PCT-US11-56135, 4 pages (May 31, 2012).
Laszlo et al., Pyrroles and Other Heterocycles as Inhibitors of P38 Kinase, Bioorganic and Medical Chemistry Letters, 8: 2689-2694 (1998).
Lethu et al., Discovery of a New Class of Protein Farnesyltransferase Inhibitors in the Arylthiophene Series, J. Med. Chem., 52: 6205-6208 (2009).
Liang, J. et al., Crystal Structure of PI3K SH3 Domain at 2.0 A Resolution, Journal of Molecular Biology, 257:632-643 (1996).
Lima, L. et al., Bioisosterism: A Useful Strategy for Molecular Modification and Drug Design, Current Medicinal Chemistry, 12: 23-49 (2005).
Liu et al., Highly Selective and Potent Thiophenes as PI3K Inhibitors with Oral Antitumor Activity, Med. Chem. Lett., 2:809-813 (2011).
Lucchesini, A Simple Way to Sequentially Connected Polycycles Containing Terminal Pyrrole Rings: Synthesis of Possible Precursors of Materials for Nonlinear Optics, Tetrahedron, 48(45): 9951-9966 (1992).
Mamedov et al., Synthesis and Some Properties of the Methyl Ester and N,N-diethylamide of 2-Azido-5-Phyenyl-4-Thiazolecarboxylic Acid, Chemistry of Heterocyclic Compounds, 29(5): 607-611 (1993).
Matschke et al., Quinomethides Versus Unsymmetric Hybrids: Two Variations of Non-Radicaloid SEM-States in Four-Electron Redox Systems of bis-4H-imidazoles, Structural Chemistry, 19(3):399-405 (2008).
Menear, K. A. et al., Identification and optimisation of novel and selective small molecular weight kinase inhibitors of mTOR, Bioorganic & Medicinal Chemistry Letters, 19:5898-5901 (2009).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-yl)-2-thienyl]-, Ryan Scientific Screening Library, Publication date: Jan. 25, 2008, CAS Registry No. 851954-74-0.
Nagasaki et al., Casreact 139:52925 (2003).
Nagasaki et al., Useful Synthesis of Various Thiazole and Polythiazolyl Derivatives from Thiocarboxamide and -Bromacyl Compound, Heterocycles, 60(2): 321-335 (2003).
Pyrazolo[1,5-a]pyrimidin-7(4H)-one,3-ethyl-5-[5-(1H-imidazol-2-yl)-2-thienyl]- (CA Index Name), CAS Registry No. 1087437-07-7, entered Dec. 21, 2008.
Revesz, L. et al., SAR of 2,6-Diamino-3,5-difluoropyridinyl Substituted Heterocycles as Novel p38 MAP Kinase Inhibitors, Bioorganic & Medicinal Chemistry Letters, 12(16):2109-2112 (2002).
Sheridan, The Most Common Chemical Replacements in Drug-Like Compounds, J. Chem. Inf. Comput. Sci., 42:103-108 (2002).
Thompson, M. J. et al., Development of a Diversity-Oriented Approach to Oxazole-5-amide Libraries, Journal of Organic Chemistry, 74(10):3856-3865 (2009).
Wang, Q. et al., Copper-Mediated Amidation of Heterocyclic and Aromatic C—H Bonds, Organic Letters, 11( 22): 5178-5180 (2009).
Welker et al., Recent Syntheses of PI3K-Akt-mTOR signaling pathway inhibitors, Bioorganic & Medicinal Chemistry, 21(14): 4063-4091 (2013).
Written Opinion for PCT-US09-03607, 5 pages (Sep. 23, 2009).
Written Opinion for PCT-US10-00234, 6 pages (Jun. 1, 2010).
Written Opinion for PCT-US11-47245, 5 pages (Dec. 22, 2011).
Written Opinion for PCT-US11-47407, 7 pages (Jun. 10, 2009).
Written Opinion for PCT-US11-56135, 13 pages (May 31, 2012).

(56) References Cited

OTHER PUBLICATIONS

Zhang, F. et al., Decarboxylative C—H Cross-Coupling of Azoles, Angew. Chem. Int. Ed., 49(15): 2768-2771 (2010).

Zhou et al., Selenium-Containing Heterocycles from Isoselenocyanates: Synthesis of 1,3-Selenazoles from N-Phenylimidoyl Isoselenocyanates, Helvetica Chimica Acta, 83: 1576-1598 (2000).

* cited by examiner

THIOPHENES AND USES THEREOF

The present application claims the benefit of U.S. Provisional Application Ser. No. 61/062,439, filed Jan. 25, 2008. The entire contents of U.S. Provisional Application Ser. No. 61/062,439 are incorporated herein by this reference.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)); ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); Di Vizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Clearly, it would be beneficial to provide novel PI3K inhibitors that possess good therapeutic properties, especially for the treatment of proliferative, inflammatory, or cardiovascular disorders.

DETAILED DESCRIPTION OF THE INVENTION

1. General Description of Compounds of the Invention

This invention provides compounds that are inhibitors of PI3K, and accordingly are useful for the treatment of proliferative, inflammatory, or cardiovascular disorders. The compounds of this invention are represented by formula I:

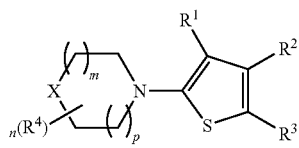

I or a pharmaceutically acceptable salt thereof, wherein:
$R^1$ is H, —CN, —COOR$^{1a}$, or —CON(R$^{1a}$)$_2$,
  wherein each occurrence of R$^{1a}$ is independently hydrogen or optionally substituted C$_{1-4}$aliphatic;
$R^2$ is —Z—R$^6$, or —R$^6$, wherein:
  Z is selected from an optionally substituted C$_{1-3}$alkylene chain, —O—, —N(R$^{2a}$)—, —S—, —S(O)—, —S(O)$_2$—, —C(O)—, —CO$_2$—, —C(O)NR$^{2a}$—, —N(R$^{2a}$)CO—, —N(R$^{2a}$)CO$_2$—, —S(O)$_2$NR$^{2a}$—, —N(R$^{2a}$)S(O)$_2$—, —OC(O)N(R$^{2a}$)—, —N(R$^{2a}$)C(O)NR$^{2a}$—, —NR$^{2a}$)S(O)$_2$N(R$^{2a}$)—, or —OC(O)—,
  $R^{2a}$ is hydrogen or an optionally substituted C$_{1-4}$ aliphatic, and
  $R^6$ is an optionally substituted group selected from C$_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur,
$R^3$ is —V$_1$—R$^{3c}$, -T$_1$-R$^{3b}$, or —V$_1$-T$_1$-R$^{3b}$ wherein:
  $V_1$ is —C(O)—, —NR$^{3a}$—, —CO$_2$—, —C(O)NR$^{3a}$—, C(O)NR$^{3a}$O—, —NR$^{3a}$C(O)NR$^{3a}$—, —NR$^{3a}$S(O)$_2$—, or —NR$^{3a}$S(O)$_2$NR$^{3a}$—;
  each occurrence of R$^{3a}$ is independently hydrogen or an optionally substituted group selected from C$_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  $T_1$ is an optionally substituted C$_1$-C$_6$alkylene chain wherein the alkylene chain optionally is interrupted by —N(R$^{3a}$)—, —O—, —S—, —S(O)—, —S(O)$_2$—, —C(O)—, —C(O)O—, —C(O)N(R$^{3a}$)—, —S(O)$_2$N(R$^{3a}$)—, —OC(O)N(R$^{3a}$)—, —N(R$^{3a}$)C(O)—, —N(R$^{3a}$)SO$_2$—, —N(R$^{3a}$)C(O)O—, —NR$^{3a}$C(O)N(R$^{3a}$)—, —N(R$^{3a}$)S(O)$_2$N(R$^{3a}$)—, —OC(O)—, or —C(O)N(R$^{3a}$)—O— or wherein T$_1$ forms part of an optionally substituted 3-7 membered cycloaliphatic or heterocyclyl ring;
  each occurrence of R$^{3b}$ is independently hydrogen, halogen, —CN, —NO$_2$, —N(R$^{3a}$)$_2$, —OR$^{3a}$, —SR$^{3a}$, —S(O)$_2$R$^{3a}$, —C(O)R$^{3a}$, —C(O)OR$^{3a}$, —C(O)N(R$^{3a}$)$_2$, —S(O)$_2$N(R$^{3a}$)$_2$, —OC(O)N(R$^{3a}$)$_2$, —N(R$^{3a}$)C(O)R$^{3a}$, —N(R$^{3a}$)SO$_2$R$^{3a}$, —N(R$^{3a}$)C(O)OR$^{3a}$, —N(R$^{3a}$)C(O)N(R$^{3a}$)$_2$, or —N(R$^{3a}$)SO$_2$N(R$^{3a}$)$_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of R$^{3c}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or
  $R^{3a}$ and $R^{3c}$ taken together with a nitrogen atom to which they are bound form an optionally substituted 4-7-membered heterocyclyl ring having 0-1 additional heteroatoms independently selected from nitrogen, oxygen, or sulfur;
each occurrence of $R^4$ is independently —R$^{4a}$, -T$_2$-R$^{4d}$, or —V$_2$-T$_2$-R$^{4d}$, wherein:
  each occurrence of R$^{4a}$, as valency and stability permit, is independently fluorine, =O, =S, —CN, —NO$_2$, —R$^{4c}$, —N(R$^{4b}$)$_2$, —OR$^{4b}$, —SR$^{4c}$, —S(O)$_2$R$^{4c}$, —C(O)R$^{4b}$, —C(O)OR$^{4b}$, —C(O)N(R$^{4b}$)$_2$, —S(O)$_2$N(R$^{4b}$)$_2$, —OC(O)N(R$^{4b}$)$_2$, —N(R$^{4e}$)C(O)R$^{4b}$, —N(R$^{4e}$)SO$_2$R$^{4c}$, —N(R$^{4e}$)C(O)OR$^{4b}$, —N(R$^{4e}$)C(O)N(R$^{4b}$)$_2$, or —N(R$^{4e}$)SO$_2$N(R$^{4b}$)$_2$, or two occurrences of R$^{4b}$, taken together with a nitrogen atom to which they are bound, form an optionally substituted 4-7-membered heterocyclyl ring having 0-1 additional heteroatoms selected from nitrogen, oxygen, or sulfur;
  each occurrence of R$^{4b}$ is independently hydrogen or an optionally substituted group selected from C$_1$-C$_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of R$^{4c}$ is independently an optionally substituted group selected from C$_1$-C$_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of R$^{4d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of R$^{4e}$ is independently hydrogen or an optionally substituted C$_{1-6}$ aliphatic group;
  each occurrence of $V_2$ is independently —N(R$^{4e}$)—, —O—, —S—, —S(O)—, —S(O)$_2$—, —C(O)—, —C(O)O—, —C(O)N(R$^{4e}$)—, —S(O)$_2$N(R$^{4e}$)—, —OC(O)N(R$^{4e}$)—, —N(R$^{4e}$)C(O)—, —N(R$^{4e}$)SO$_2$—, —N(R$^{4e}$)C(O)O—, —N eC(O)N(R$^{4e}$)—, —N(R$^{4e}$)SO$_2$N(R$^{4e}$)—, —OC(O)—, or —C(O)N(R$^{4e}$)—O—; and
  $T_2$ is an optionally substituted C$_1$-C$_6$alkylene chain wherein the alkylene chain optionally is interrupted by —N(R$^{4a}$)—, —O—, —S—, —S(O)—, —S(O)$_2$—, —C(O)—, —C(O)O—, —C(O)N(R$^{4a}$)—, —S(O)$_2$N(R$^{4a}$)—, —OC(O)N(R$^{4a}$)—, —N(R$^{4a}$)C(O)—, —N(R$^{4a}$)SO$_2$—, —N(R$^{4a}$)C(O)O—, —NR$^{4a}$C(O)N(R$^{4a}$)—, —N(R$^{4a}$)S(O)$_2$N(R$^{4a}$)—, —OC(O)—, or —C(O)N(R$^{4a}$)—O— or wherein T$_2$ or a portion thereof optionally forms part of an optionally substituted 3-7 membered cycloaliphatic or heterocyclyl ring;

n is 0-6;

m is 0, 1, or 2;

p is 0, 1, or 2; and

X is O, S, C(O), S(O), S(O)$_2$, —CHF, —CF$_2$, or —CHOH, provided that:
(a) when $R^1$ is H, then $R^2$ is an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen or sulfur; and
(b) a compound of formula I is other than:
(i) 2-thiophenecarboxylic acid, 3-(4-chlorophenyl)-4-cyano-5-(4-morpholinyl)-;
(ii) 2-thiophenecarboxylic acid, 3-(4-chlorophenyl)-4-cyano-5-(4-morpholinyl)-, methyl ester;
(iii) 3-thiophenecarbonitrile, 5-benzoyl-4-(methylamino)-2-(4-morpholinyl)-;
(iv) Acetamide, N-[2-benzoyl-4-cyano-5-(4-morpholinyl)-3-thienyl]-2-iodo-;
(v) Acetamide, N-[2-benzoyl-4-cyano-5-(4-morpholinyl)-3-thienyl]-2-chloro-;
(vi) Acetamide, N-[2-benzoyl-4-cyano-5-(4-morpholinyl)-3-thienyl]-2-chloro-N-methyl-; or
(vii) 2-Propenoic acid, 3-[3-(4-chlorophenyl)-5-(4-morpholinyl)-2-thienyl]-, methyl ester.

2. Compounds and Definitions

Compounds of this invention include those described generally for formula I above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$aromatic hydrocarbon moiety comprising one to three aromatic rings. Preferably, the aryl group is a $C_{6-10}$aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, $-NO_2$, $-CN$, $-R^+$, $-C(R^+)=C(R^+)_2$, $-C\equiv C-R^+$, $-OR^+$, $-SR^\circ$, $-S(O)R^\circ$, $-SO_2R^\circ$, $-SO_3R^+$, $-SO_2N(R^+)_2$, $-N(R^+)_2$, $-NR^+C(O)R^+$, $-NR^+C(S)R^+$, $-NR^+C(O)N(R^+)_2$, $-NR^+C(S)N(R^+)_2$, $-N(R^+)C(=NR^+)-N(R^+)_2$, $-N(R^+)C(=NR^+)-R^\circ$, $-NR^+CO_2R^+$, $-NR^+SO_2R^\circ$, $-NR^+SO_2N(R^+)_2$, $-O-C(O)R^+$, $-O-CO_2R^+$, $-OC(O)N(R^+)_2$, $-C(O)R^+$, $-C(S)R^\circ$, $-CO_2R^+$, $-C(O)-C(O)R^+$, $-C(O)N(R^+)_2$, $-C(S)N(R^+)_2$, $-C(O)N(R^+)-OR^+$, $-C(O)N(R^+)C(=NR^+)-N(R^+)_2$, $-N(R^+)C(=NR^+)-N(R^+)-C(O)R^+$, $-C(=NR^+)-N(R^+)_2$, $-C(=NR^+)-OR^+$, $-N(R^+)-N(R^+)_2$, $-C(=NR^+)-N(R^+)-OR^+$, $-C(R^\circ)=N-OR^+$, $-P(O)(R^+)_2$, $-P(O)(OR^+)_2$, $-O-P(O)-OR^+$, and $-P(O)(NR^+)-N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R^\circ$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: $=O$, $=S$, $=C(R^*)_2$, $=N-N(R^*)_2$, $=N-OR^*$, $=N-NHC(O)R^*$, $=N-NHCO_2R^\circ$, $=N-NHSO_2R^\circ$ or $=N-R^*$ where $R^\circ$ is defined above, and each $R^*$ is independently selected from hydrogen or an optionally substituted $C_{1-6}$ aliphatic group.

In addition to the substituents defined above and herein, optional substituents on the nitrogen of a non-aromatic heterocyclic ring also include and are generally selected from $-R^+$, $-N(R^+)_2$, $-C(O)R^+$, $-C(O)OR^+$, $-C(O)C(O)R^+$, $-C(O)CH_2C(O)R^+$, $-S(O)_2R^+$, $-S(O)_2N(R^+)_2$, $-C(S)N(R^+)_2$, $-C(=NH)-N(R^+)_2$, or $-N(R^+)S(O)_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of $R^+$ (or any other variable similarly defined in the specification and claims herein), are taken together with their intervening atom(s) include, but are not limited to the following: a) two independent occurrences of $R^+$ (or any other variable similarly defined in the specification or claims herein) that are bound to the same atom and are taken together with that atom to form a ring, for example, $N(R^+)_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of

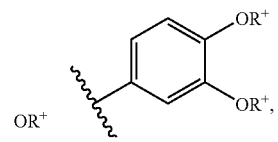

these two occurrences of $R^+$ are taken together with the oxygen atoms to which they are bound to form a fused 6-membered oxygen containing ring:

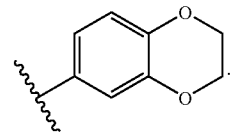 [SMILES: *c1ccc2c(c1)OCCO2]

It will be appreciated that a variety of other rings (e.g., spiro and bridged rings) can be formed when two independent occurrences of $R^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In certain embodiments, for compounds of general formula I, one or more substituents are selected from:
(a) X is O;
(b) $R^1$ is CN;
(c) $R^2$ is an optionally substituted 6-10-membered aryl, or 5-10-membered heteroaryl having 1-5 heteroatoms independently selected from nitrogen, oxygen, or sulfur;
(d) $R^3$ is selected from $V_1$—$R^{3c}$ or —$V_1$-$T_1$-$R^{3b}$;
(e) n is 0-2; or
(f) $R^4$ is —$R^{4a}$.

In some embodiments, $R^3$ is selected from —CON($R^{3a}$)($R^{3c}$), —N$R^{3a}$C(O)N($R^{3a}$)($R^{3c}$), —COO$R^{3c}$; —CON($R^{3a}$)-$T^1$-$R^{3b}$, —N$R^{3a}$C(O)N($R^{3a}$)($R^{3c}$)-$T^1$-$R^{3b}$, or —COO$R^{3c}$-$T^1$-$R^{3b}$, where $T^1$ is optionally substituted $C_1$-$C_4$alkylene optionally interrupted by one occurrence of —O—, —NHC(O)—, —C(O)NH—, or —NH—.

In other embodiments, $R^2$ is optionally substituted with 1-4 independent occurrences of $R^7$, wherein $R^7$ is —$R^{7a}$, -$T_3$-$R^{7d}$, or $V_3$-$T_3$-$R^{7d}$, and:
each occurrence of $R^{7a}$ is independently halogen, —CN, —NO$_2$, —$R^{7c}$, —N($R^{7b}$)$_2$, —O$R^{7b}$, —S$R^{7c}$, —S(O)$_2$$R^{7c}$, —C(O)$R^{7b}$, —C(O)O$R^{7b}$, C(O)N($R^{7b}$)$_2$, S(O)$_2$N($R^{7b}$)$_2$, OC(O)N($R^{7b}$)$_2$, —N($R^{7e}$)C(O)$R^{7b}$, —N($R^{7e}$)SO$_2$$R^{7c}$, —N($R^{7e}$)C(O)O$R^{7b}$, —N($R^{7e}$)C(O)N($R^{7b}$)$_2$, or —N($R^{7e}$)SO$_2$N($R^{7b}$)$_2$, or two occurrences of $R^{7b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{7b}$ is independently hydrogen or an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{7c}$ is independently an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{7d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{7e}$ is independently hydrogen or an optionally substituted $C_{1-6}$aliphatic group;

each occurrence of $V_3$ is independently —N($R^{7e}$)—, —O$^-$, —S—, —S(O)—, —S(O)$_2$—, —C(O)—, —C(O)O—, —C(O)N($R^{7e}$)—, —S(O)$_2$N($R^{7e}$), —OC(O)N($R^{7e}$)—, —N($R^{7e}$)C(O)—, —N($R^{7e}$)SO$_2$—, —N($R^{7e}$)C(O)O—, —N$R^{7e}$C(O)N($R^{7e}$)—, —N($R^{7e}$)SO$_2$N($R^{7e}$)—, —OC(O)—, or —C(O)N($R^{7e}$)—O—; and $T_3$ is an optionally substituted $C_1$-$C_6$alkylene chain wherein the alkylene chain optionally is interrupted by —N($R^{7a}$)—, —O—, —S—, —S(O)—, —S(O)$_2$—, —C(O)—, —C(O)O—, —C(O)N($R^{7a}$)—, —S(O)$_2$N($R^{7a}$)—, —OC(O)N($R^{7a}$)—, —N($R^{7a}$)C(O)—, —N($R^{7a}$)SO$_2$—, —N($R^{7a}$)C(O)O—, —N$R^{7a}$C(O)N($R^{7a}$)—, —N($R^{7a}$)S(O)$_2$N($R^{7a}$)—, —OC(O)—, or —C(O)N($R^{7a}$)—O— or wherein $T_3$ or a portion thereof optionally forms part of an optionally substituted 3-7 membered cycloaliphatic or heterocyclyl ring.

In still other embodiments of the invention, for compounds of general formula I, X is O and $R^1$, is CN and the compound is represented by formula I-A:

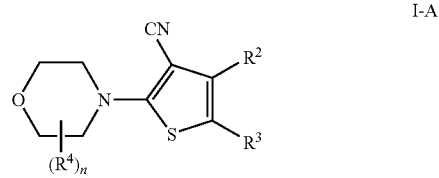

I-A where $R^2$, $R^3$, $R^4$ and n are as described generally above and in classes and subclasses described above and herein.

In some embodiments, for compounds of formula I-A:
$R^2$ is an optionally substituted 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

R³ is selected from V₁—R³ᶜ or —V¹-T¹-R³ᵇ;
n is 0-2; and
R⁴ is —R⁴ᵃ.

In other embodiments, for compounds of formula I-A:

R² is an optionally substituted 6-10-membered aryl, or a 5-10-membered heteroaryl ring having 1-5 heteroatoms independently selected from nitrogen, oxygen, or sulfur; wherein R² is optionally substituted with 1-4 independent occurrences of R⁷, wherein R⁷ is —R⁷ᵃ, -T₃-R⁷ᵈ, or —V₃-T₃-R⁷ᵈ, and:

each occurrence of R⁷ᵃ is independently halogen, —CN, —NO₂, —R⁷ᶜ, —N(R⁷ᵇ)₂, —OR⁷ᵇ, —SR⁷ᶜ, —S(O)₂R⁷ᶜ, —C(O)R⁷ᵇ, C(O)OR⁷ᵇ, —C(O)N(R⁷ᵇ)₂, —S(O)₂N(R⁷ᵇ)₂, —OC(O)N(R⁷ᵇ)₂, —N(R⁷ᵉ)C(O)R⁷ᵇ, —N(R⁷ᵉ)SO₂R⁷ᶜ, N(R⁷ᵉ)C(O)OR⁷ᵇ, —N(R⁷ᵉ)C(O)N(R⁷ᵇ)₂, or —N(R⁷ᵉ)SO₂N(R⁷ᵇ)₂;

each occurrence of R⁷ᵇ is independently hydrogen or an optionally substituted group selected from C₁-C₆aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or two occurrences of R⁷ᵇ, taken together with a nitrogen atom to which they are bound, form an optionally substituted 4-7-membered heterocyclyl ring having 0-1 additional heteroatoms selected from nitrogen, oxygen, or sulfur;

each occurrence of R⁷ᶜ is independently an optionally substituted group selected from C₁-C₆aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl independently selected from nitrogen, oxygen, or sulfur;

each occurrence of R⁷ᵈ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R⁷ᵉ is independently hydrogen or an optionally substituted C₁-₆aliphatic group;

each occurrence of V₃ is independently —N(R⁷ᵉ)—, —O—, —S—, —S(O)—, —S(O)₂—, —C(O)—, —C(O)O—, —C(O)N(R⁷ᵉ), —S(O)₂N(R⁷ᵉ), —OC(O)N(R⁷ᵉ)—, —N(R⁷ᵉ)C(O)—, —N(R⁷ᵉ)SO₂—, —N(R⁷ᵉ)C(O)O—, —NR⁷ᵉC(O)N(R⁷ᵉ)—, —N(R⁷ᵉ)SO₂N(R⁷ᵉ)—, —OC(O)—, or —C(O)N(R⁷ᵉ)—O—; and T₃ is an optionally substituted C₁-C₆alkylene chain wherein the alkylene chain optionally is interrupted by —N(R⁷ᵃ)—, —O—, —S—, —S(O)—, —S(O)₂—, —C(O)—, —C(O)O—, —C(O)N(R⁷ᵃ)—, —S(O)₂N(R⁷ᵃ)—, —OC(O)N(R⁷ᵃ)—, —N(R⁷ᵃ)C(O)—, —N(R⁷ᵃ)SO₂—, —N(R⁷ᵃ)C(O)O—, —NR⁷ᵃC(O)N(R⁷ᵃ)—, —N(R⁷ᵃ)S(O)₂N(R⁷ᵃ)—, —OC(O)—, or —C(O)N(R⁷ᵃ)—O— or wherein T₃ or a portion thereof optionally forms part of an optionally substituted 3-7 membered cycloaliphatic or heterocyclyl ring; R³ is selected from —CON(R³ᵃ)(R³ᶜ), —NR³ᵃC(O)N(R³ᵃ)(R³ᶜ), COOR³ᶜ, —CON(R³ᵃ)-T¹-R³ᵇ, —NR³ᵃC(O)N(R³ᵃ)(R³ᶜ)-T¹-R³ᵇ, or —COOR³ᶜ-T¹-R³ᵇ, wherein T¹ is optionally substituted C₁-C₄alkylene optionally interrupted by one occurrence of —O—, —NHC(O)—, —C(O)NH—, or —NH—, R³ᵃ, is hydrogen or an optionally substituted C₁-₆aliphatic group, R³ᵇ is hydrogen, halogen, OR³ᵃ, or an optionally substituted group selected from 6-10-membered aryl, or 5-10-membered heteroaryl having 1-5 heteroatoms independently selected from nitrogen, oxygen, or sulfur, and R³ᶜ is hydrogen, C₁-₆aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and n is 0-2.

In still other embodiments, for compounds of formula I-A:

R² is a phenyl group substituted with 1-3 independent occurrences of halogen, —CN, —NO₂, —R⁷ᶜ, —N(R⁷ᵇ)₂, —OR⁷ᵇ, —SR⁷ᶜ, —S(O)₂R⁷ᶜ, —C(O)R⁷ᵇ, —C(O)OR⁷ᵇ, —C(O)N(R⁷ᵇ)₂, —S(O)₂N(R⁷ᵇ)₂, —OC(O)N(R⁷ᵇ)₂, —N(R⁷ᵉ)C(O)R⁷ᵇ, —N(R⁷ᵉ)SO₂R⁷ᶜ, —N(R⁷ᵉ)C(O)OR⁷ᵇ, —N(R⁷ᵉ)C(O)N(R⁷ᵇ)₂, or —N(R⁷ᵉ)SO₂N(R⁷ᵇ)₂;

R³ is selected from —CON(R³ᵃ)(R³ᶜ), —NR³ᵃC(O)N(R³ᵃ)(R³ᶜ), or —COOR³ᶜ, wherein R³ᵃ is hydrogen or an optionally substituted C₁-₆aliphatic group and R³ᵃ is hydrogen or an optionally substituted C₁-₆aliphatic group; and n is 0.

In yet other embodiments, for compounds of formula I-A:

R² is a phenyl group substituted with 1-3 independent occurrences of halo, C₁-₃alkyl, CN, C₁-₃haloalkyl, —OC₁-₃alkyl, —OC₁-₃haloalkyl, —NHC(O)C₁-₃alkyl, —NHC(O)NHC₁-₃alkyl, NHS(O)₂C₁-₃alkyl, or —COH.

Table 1 below depicts certain exemplary compounds of formula I:

TABLE 1

Exemplary Compounds of formula I:

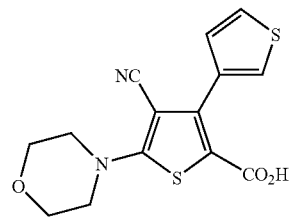

1

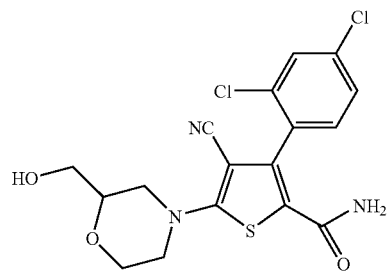

2

TABLE 1-continued
Exemplary Compounds of formula I:
3
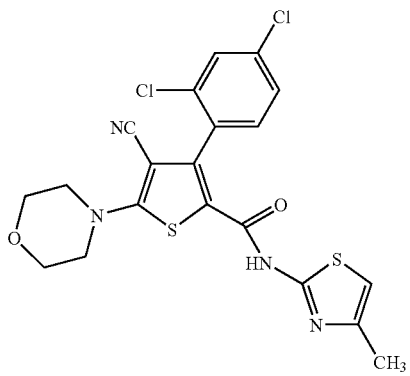
4
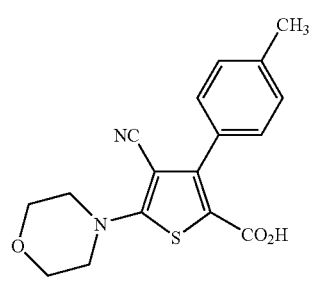
5
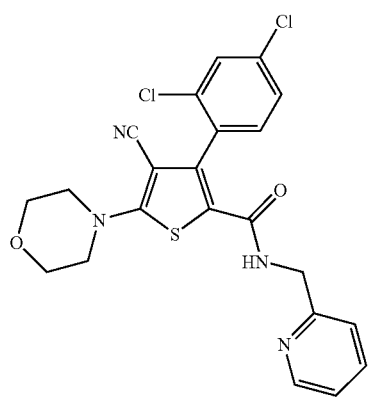
6
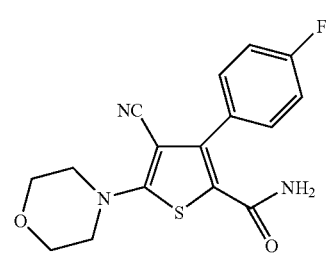
TABLE 1-continued
Exemplary Compounds of formula I:
7
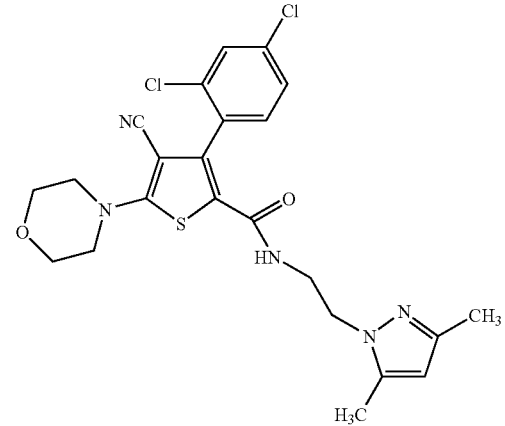
8
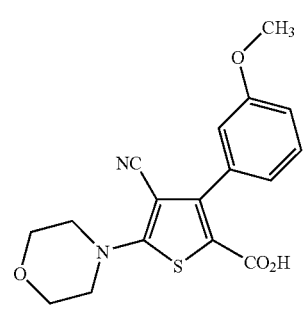
9
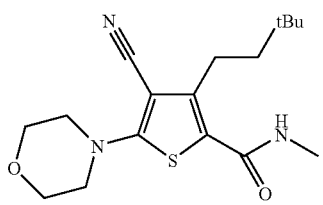 [SMILES: CNC(=O)c1sc(N2CCOCC2)c(C#N)c1CCC(C)(C)C]
10
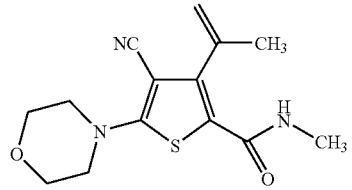
11
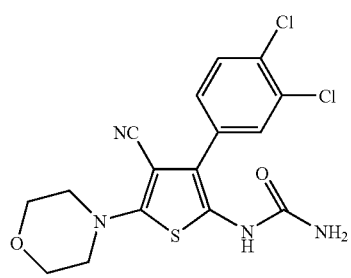

TABLE 1-continued
Exemplary Compounds of formula I:
12
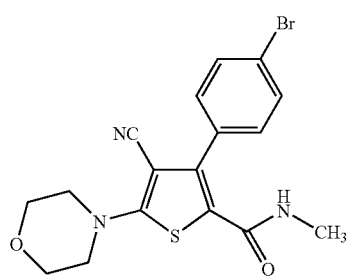
13
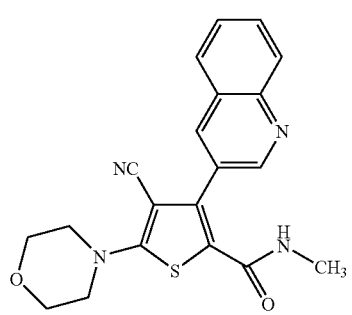
14
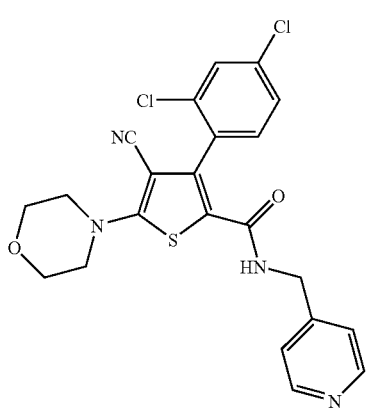
15
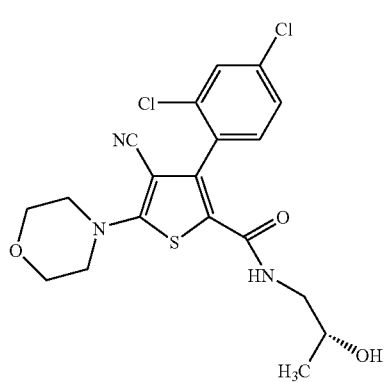
TABLE 1-continued
Exemplary Compounds of formula I:
16
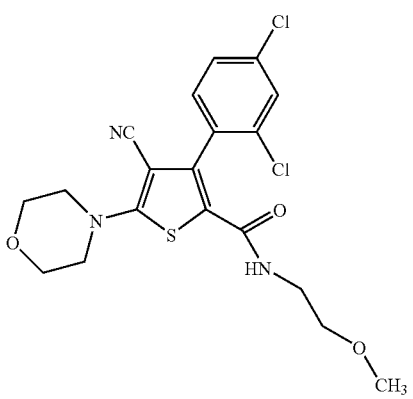
17
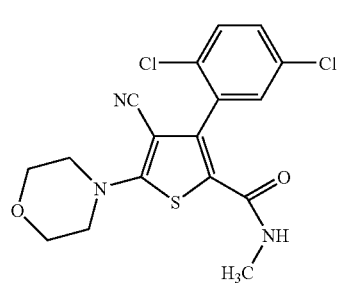
18
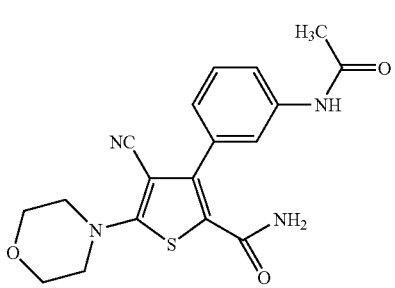
19
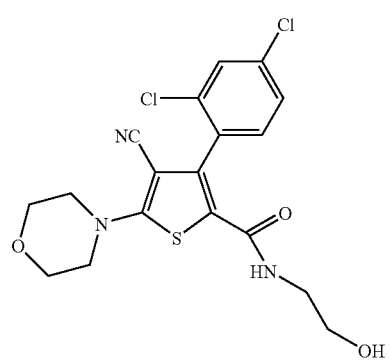

TABLE 1-continued
Exemplary Compounds of formula I:
20
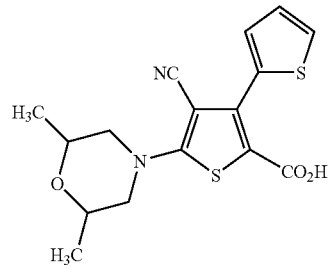
21
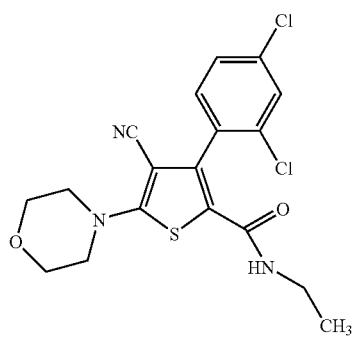
22
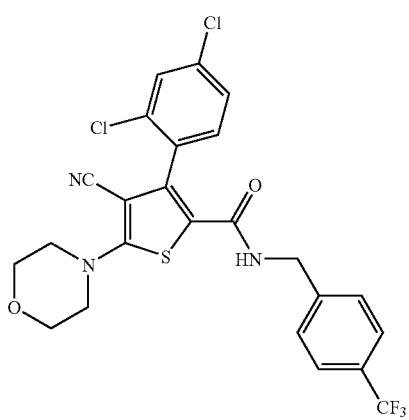
23
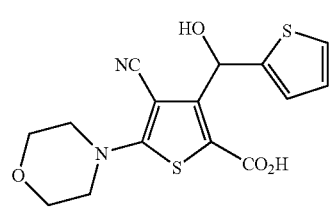
TABLE 1-continued
Exemplary Compounds of formula I:
24
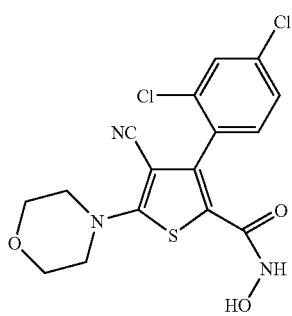
25
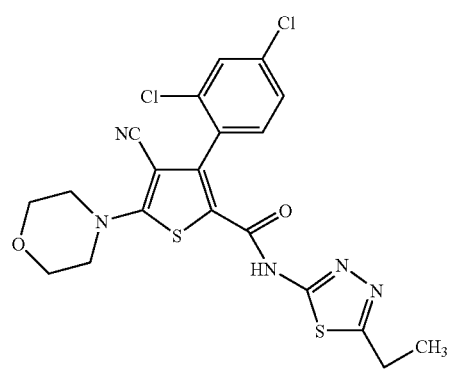
27
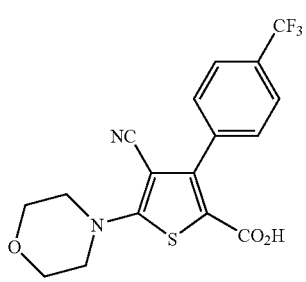
28
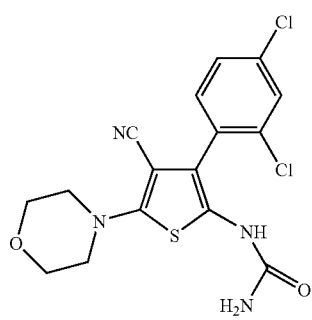

TABLE 1-continued
Exemplary Compounds of formula I:
29
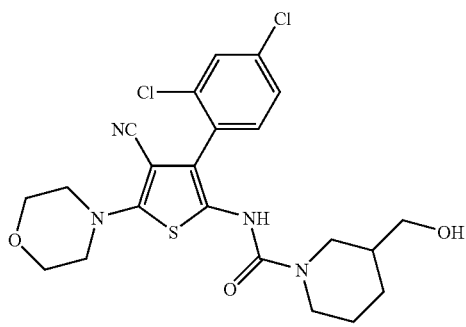
30
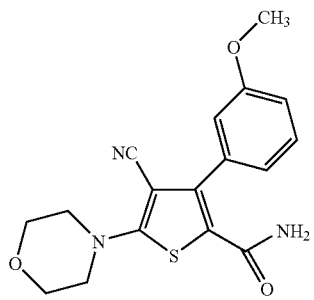
31
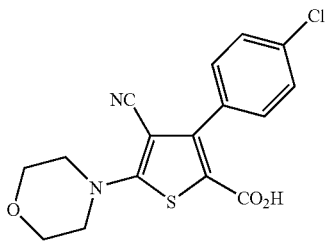
TABLE 1-continued
Exemplary Compounds of formula I:
32
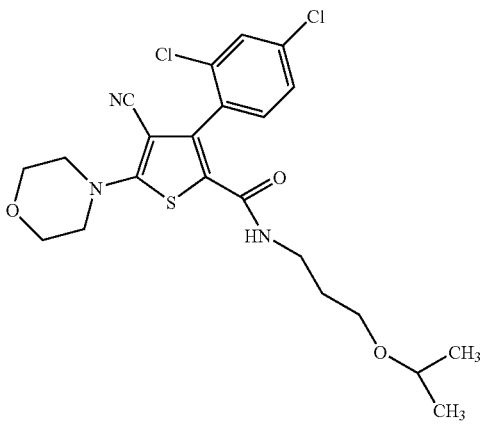
33
34
35
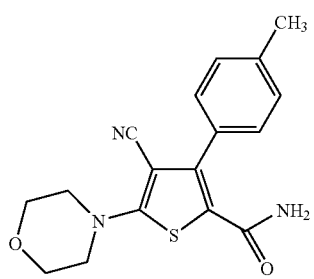

TABLE 1-continued
Exemplary Compounds of formula I:
36
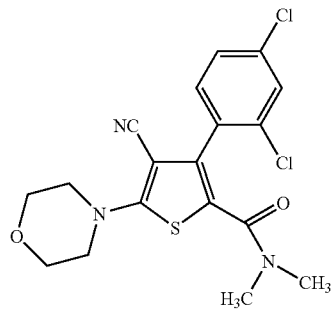
37
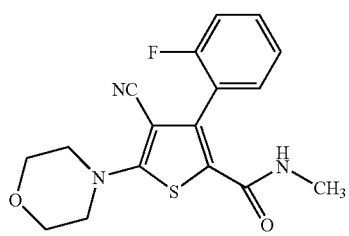
38
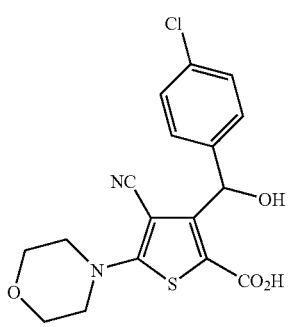
39
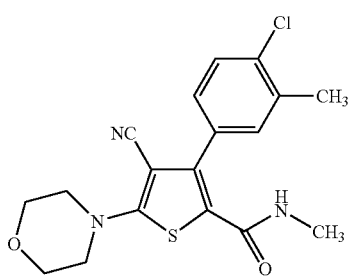
40
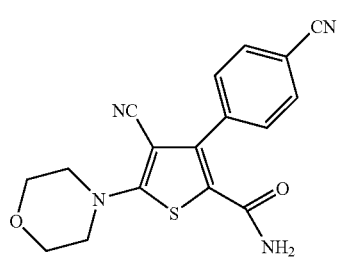
TABLE 1-continued
Exemplary Compounds of formula I:
41
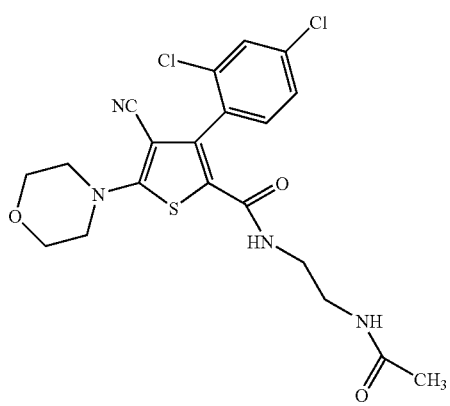
42
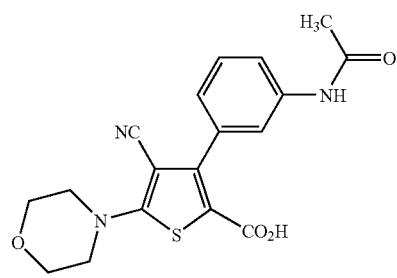
43
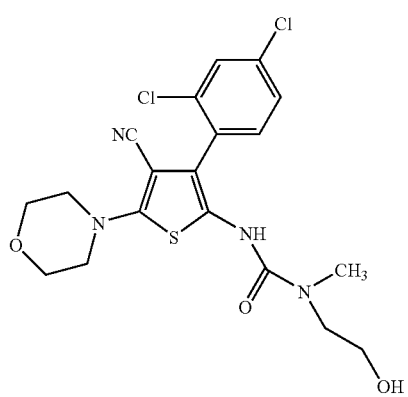
44
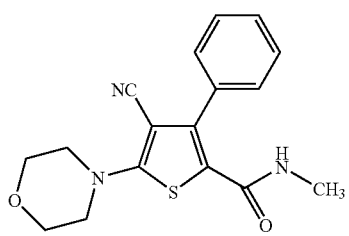

TABLE 1-continued
Exemplary Compounds of formula I:
45
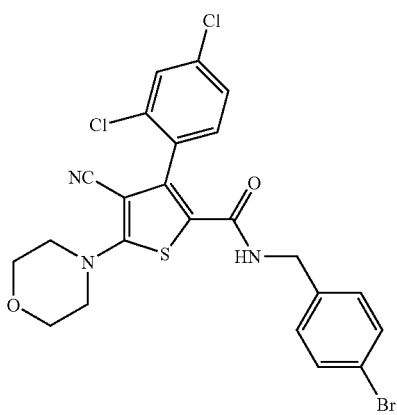
46
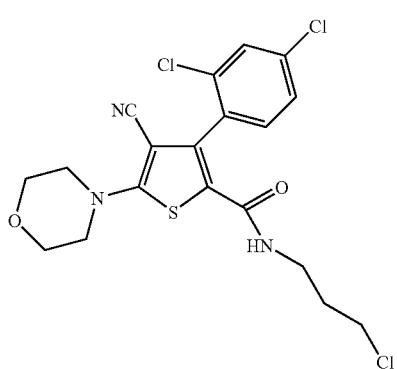
47
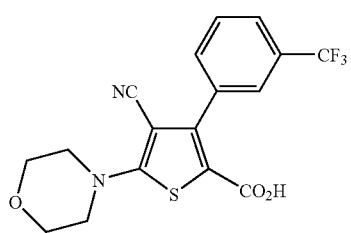
48
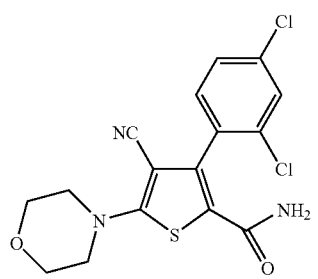
TABLE 1-continued
Exemplary Compounds of formula I:
49
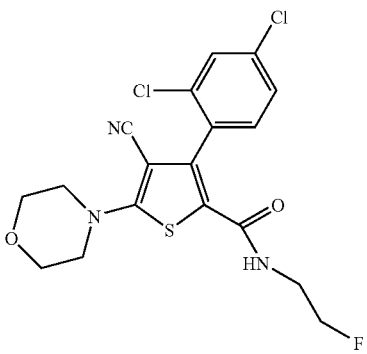
50
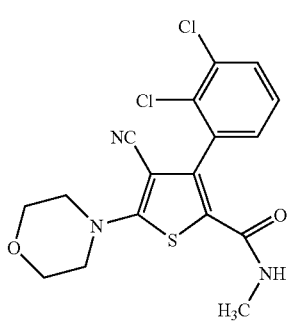
51
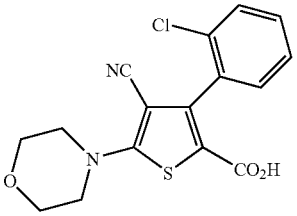
52
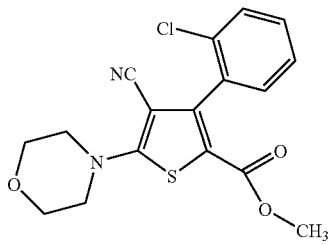
53
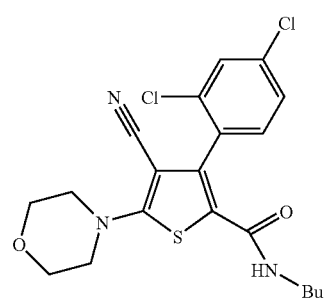

TABLE 1-continued
Exemplary Compounds of formula I:
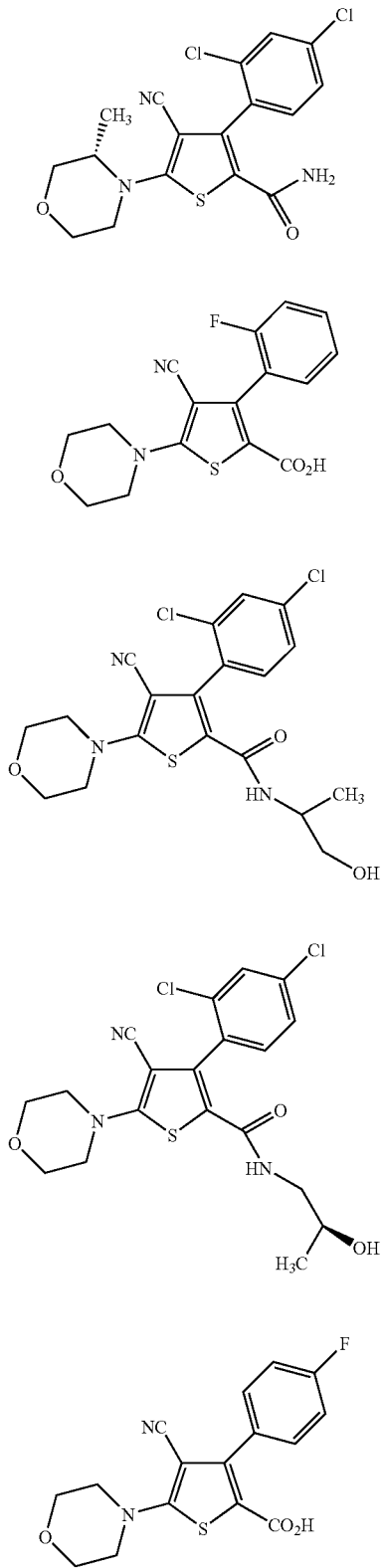
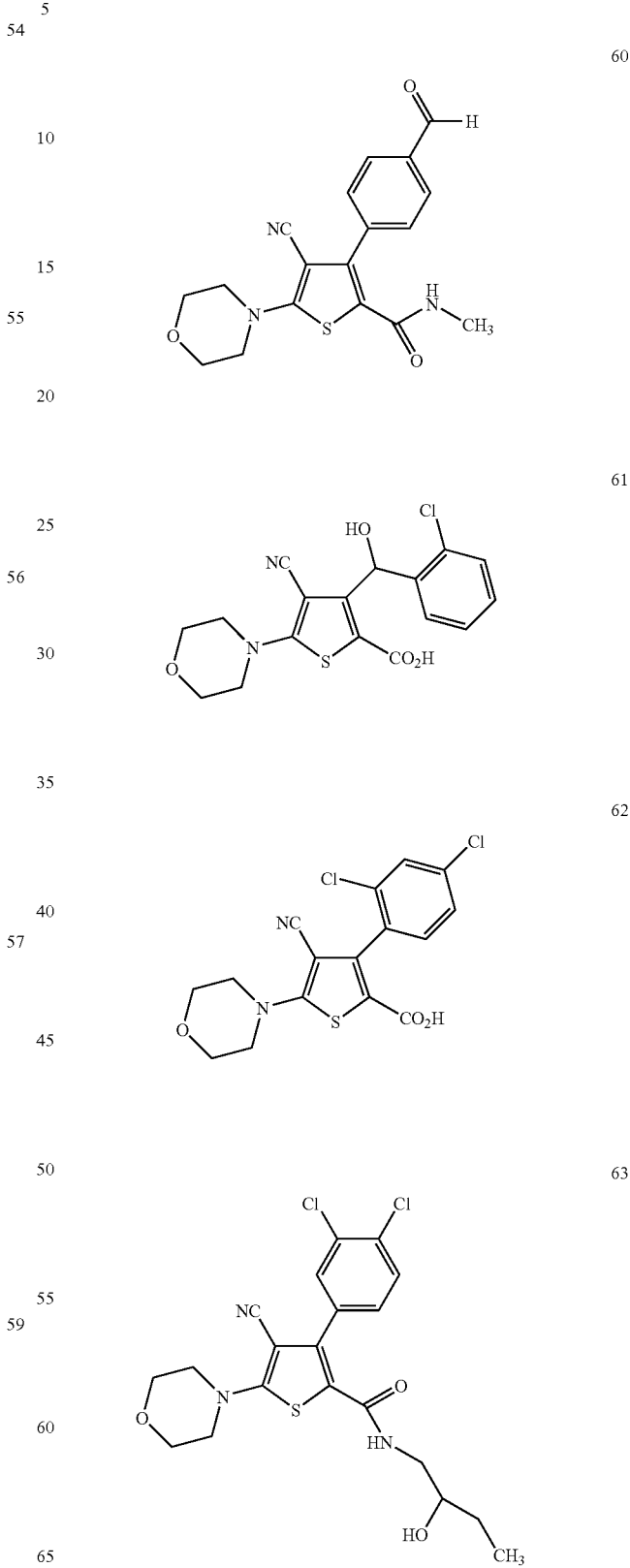

TABLE 1-continued
Exemplary Compounds of formula I:
64
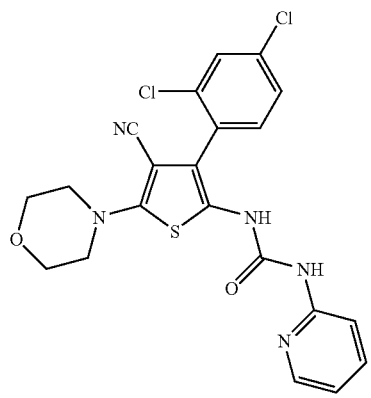
65
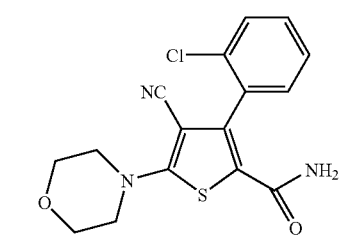
66
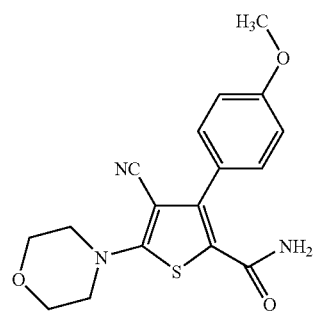
67
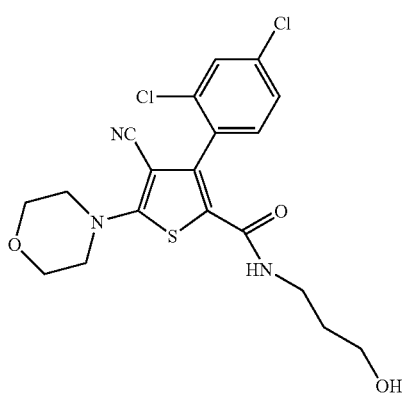
TABLE 1-continued
Exemplary Compounds of formula I:
68
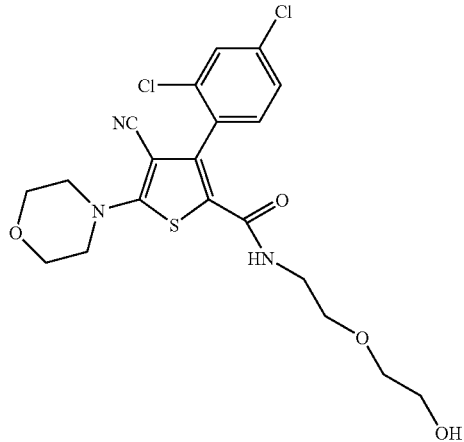
69
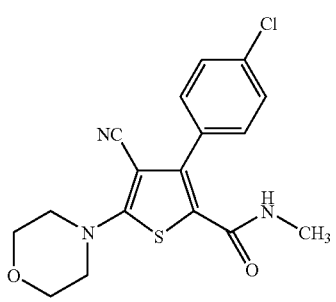
70
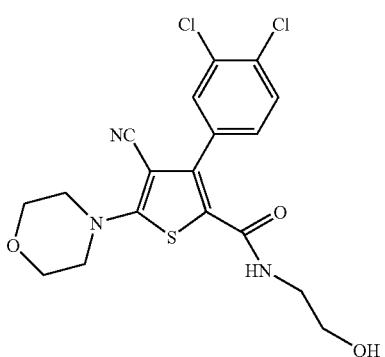
71
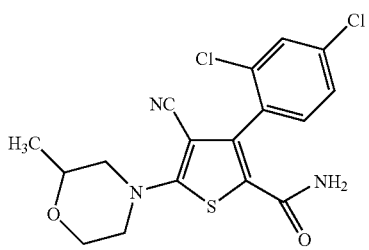

TABLE 1-continued
Exemplary Compounds of formula I:
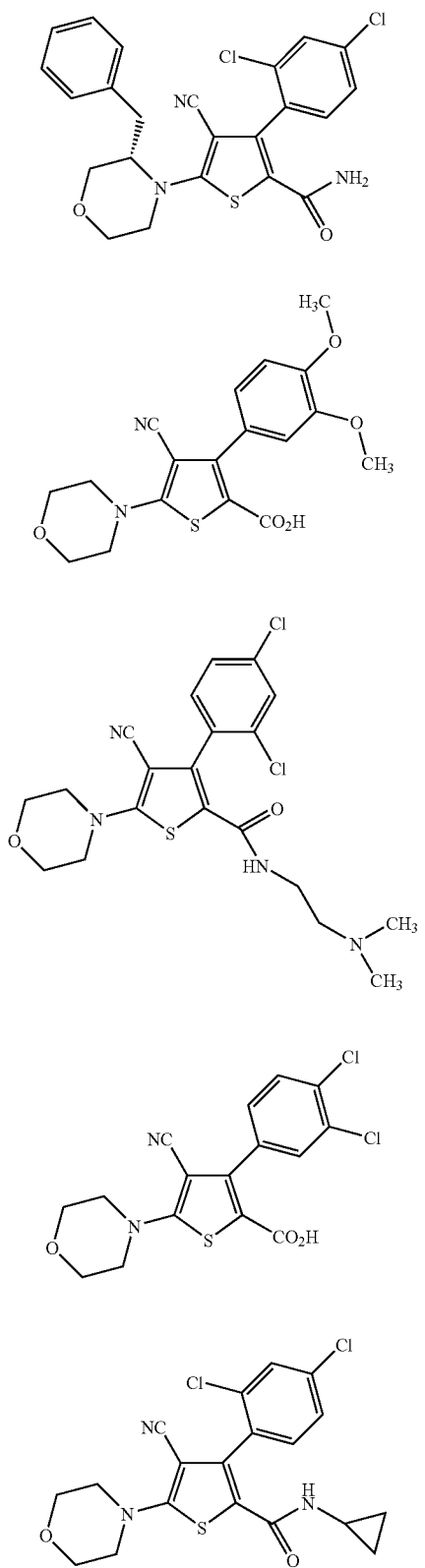
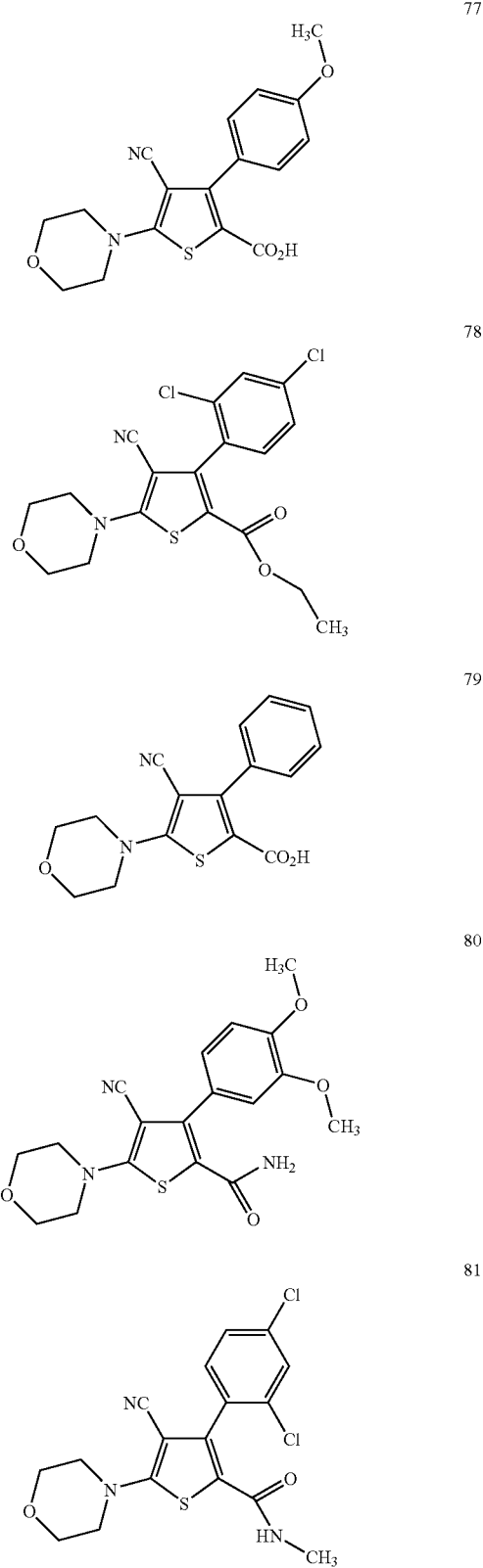

TABLE 1-continued

Exemplary Compounds of formula I:

82
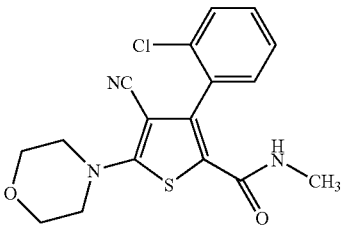

83
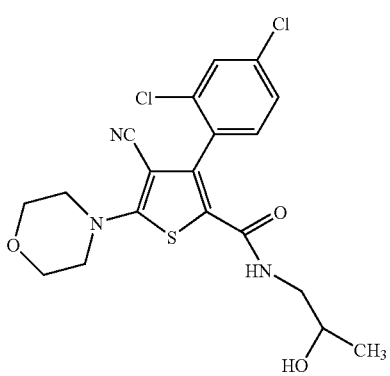

84
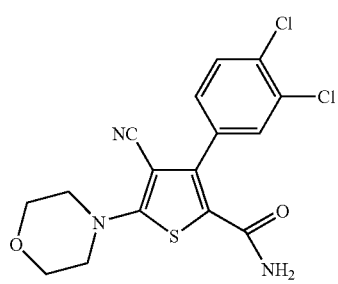

85
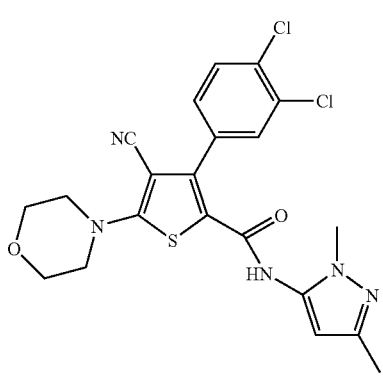

TABLE 1-continued

Exemplary Compounds of formula I:

86
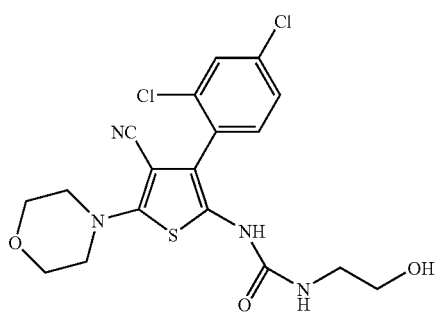

87
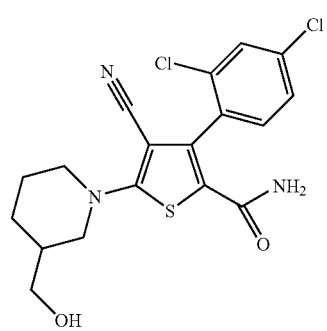 [SMILES: N#Cc1c(N2CCCC(CO)C2)sc(C(N)=O)c1-c1ccc(Cl)cc1Cl]

88
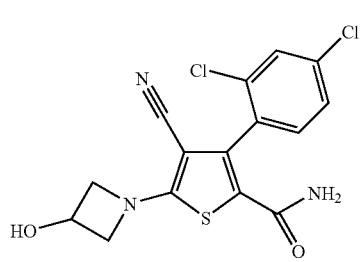 [SMILES: N#Cc1c(N2CC(O)C2)sc(C(N)=O)c1-c1ccc(Cl)cc1Cl]

89
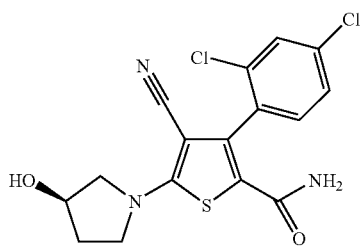 [SMILES: N#Cc1c(N2CC[C@@H](O)C2)sc(C(N)=O)c1-c1ccc(Cl)cc1Cl]

4 General Synthetic Methods and Intermediates:

The compounds of the present invention can be prepared by methods known to one of ordinary skill in the art and/or by reference to the schemes shown below and the synthetic examples that follow. Exemplary synthetic routes are set forth in Schemes 1-8 below, and in the Examples.

Scheme 1: General route for the synthesis of 3-substituted 4-cyano-5-morpholin-4-ylthiophene-2-carboxamides

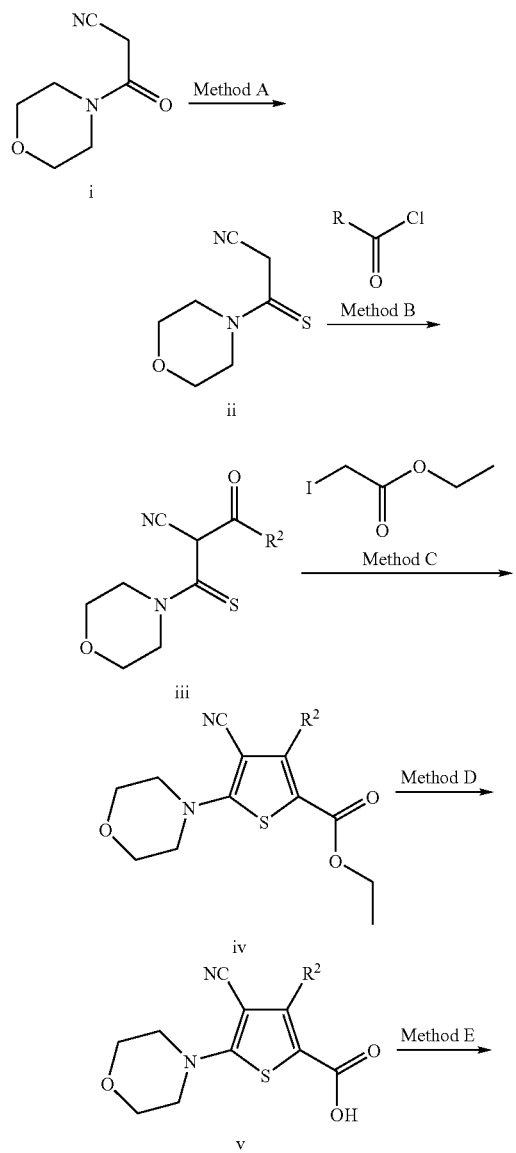

base, such as NaOH in aqueous conditions using cosolvents, such as THF and MeOH to afford carboxylic acids v (Method D). Amides vi can be obtained by coupling of compounds v with ammonia using a suitable coupling reagent, such as EDCI and HOBT in DCM (Method E).

Scheme 2: General route for the synthesis of 3-substituted N-[4-cyano-5-morpholin-4-yl-thienyl]ureas

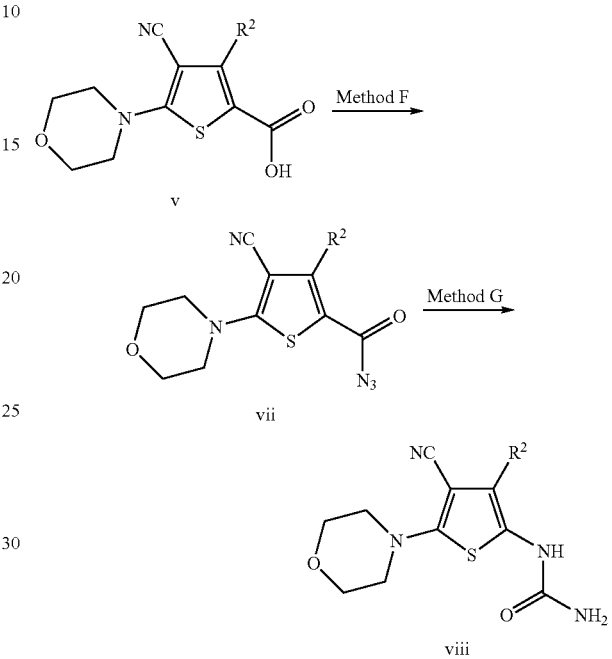

Scheme 2 above shows a general route for preparing compounds of formula (viii). As shown in Scheme 2, conversion of acids v to azides vii can be achieved using an appropriate azide source, such as DPPA in the presence of a suitable base, such as TEA in THF (Method F). Treatment of azides vii with ammonia in dioxane under elevated temperature affords ureas of formula viii (Method G).

Schem 3: Alternate route for the synthesis of 3-substituted 4-cyano-5-morpholin-4-ylthiophene-2-carboxamides

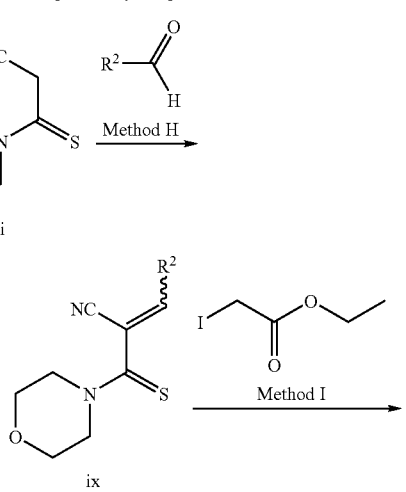

Scheme 1 above shows a general route for preparing compounds of formula (vi). As shown in Scheme 1, conversion of amide i to thioamide ii can be accomplished using a suitable reagent, such as Lawesson's reagent, in THF (Method A). Thioamide ii can be coupled with acyl chlorides in the presence of an appropriate base, such as DIPEA, in ACN (Method B) to afford compounds of formula iii, that can be subsequently coupled with a suitable α-haloacetate ester, such as iodoethylacetate or bromoethylacetate in a one-pot process using microwave irradiation to afford substituted thiophenes iv (Method C). Esters iv can be hydrolyzed using a suitable

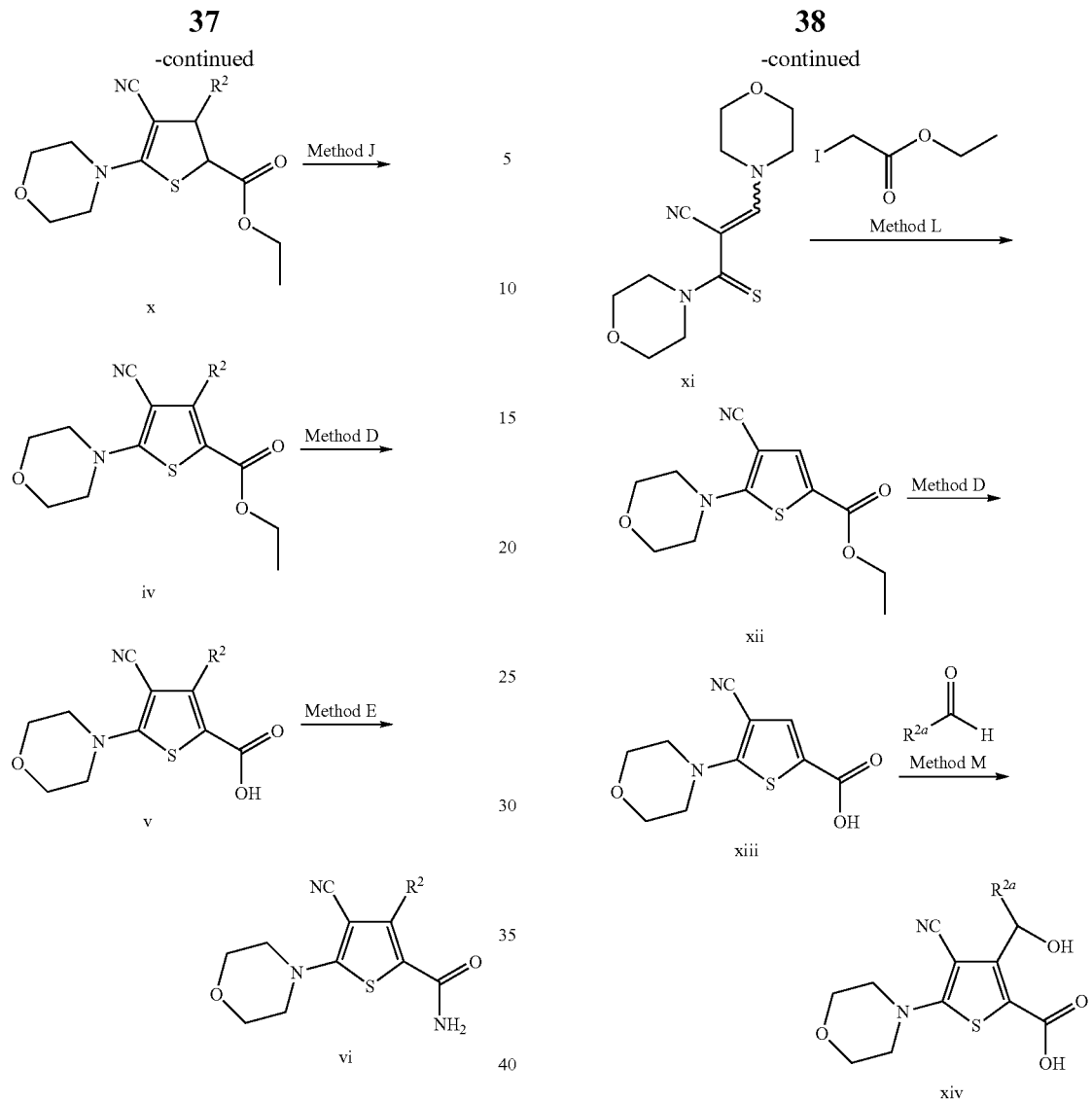

Scheme 3 above shows an alternate route for preparing compounds of formula (vi). As shown in Scheme 3, thioamide ii is treated with an aldehyde in the presence of a suitable base, such as piperidine in ethanol at elevated temperature to afford ix (Method H), which is treated with ethyl iodoacetate and an appropriate base, such as DIPEA in ACN under microvawe irradiation to give dihydrothiophenes x (Method I). Oxidation of x with a suitable reagent, such as DDQ in toluene at elevated temperature gives thiophenes iv (Method J), that can afford amides vi using methods D and E.

Scheme 4 above shows a general route for preparing compounds of formula (xiv). As shown in Scheme 4, thioamide ii is treated with morpholine in the presence of triethylorthoformate under microvawe irradiation to afford xi (Method K). Subsequent reaction of xi with ethyl iodoacetate gives thiophene xii (method L), which is hydrolyzed as reported in Method L to give xiii. Treatment xiii with a suitable lithiation reagent, such as n-BuLi in THF at low temperature followed by reaction with an aldehyde affords compounds of formula xiv (Method M).

Scheme 4: General route for the synthesis of 3-substituted thiophene-2-carboxylic acids

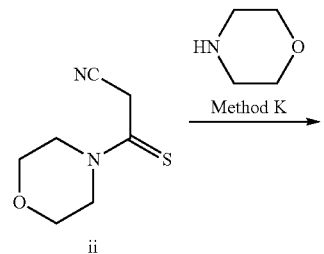

Scheme 5: General route for the synthesis of 3-substituted N-Methyl 4-cyano-5-morpholin-4-ylthiophene-2-carboxamides

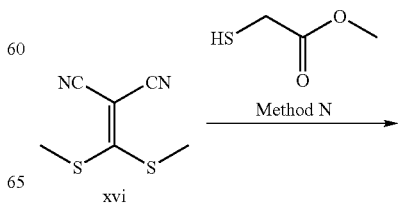

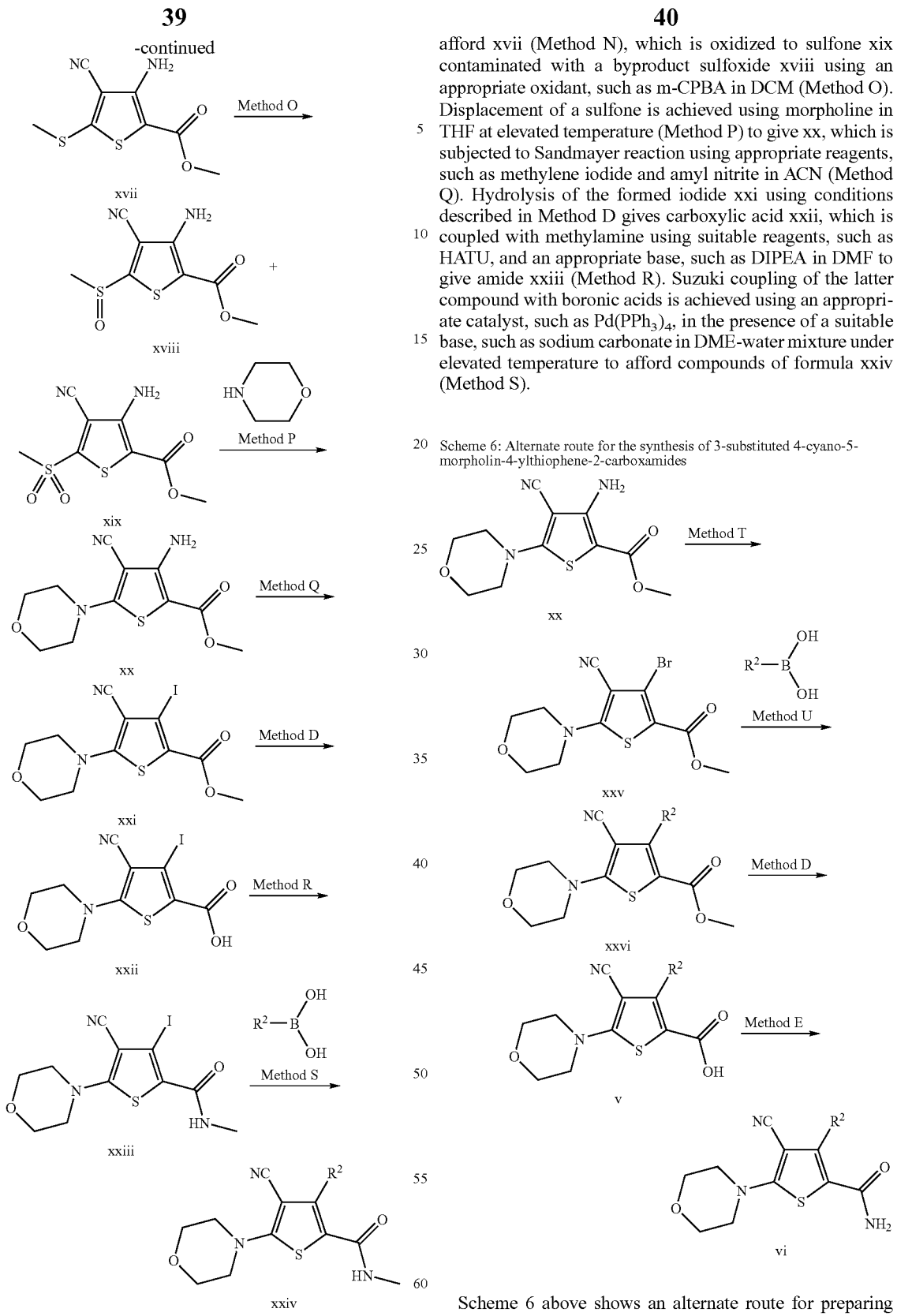

afford xvii (Method N), which is oxidized to sulfone xix contaminated with a byproduct sulfoxide xviii using an appropriate oxidant, such as m-CPBA in DCM (Method O). Displacement of a sulfone is achieved using morpholine in THF at elevated temperature (Method P) to give xx, which is subjected to Sandmayer reaction using appropriate reagents, such as methylene iodide and amyl nitrite in ACN (Method Q). Hydrolysis of the formed iodide xxi using conditions described in Method D gives carboxylic acid xxii, which is coupled with methylamine using suitable reagents, such as HATU, and an appropriate base, such as DIPEA in DMF to give amide xxiii (Method R). Suzuki coupling of the latter compound with boronic acids is achieved using an appropriate catalyst, such as Pd(PPh$_3$)$_4$, in the presence of a suitable base, such as sodium carbonate in DME-water mixture under elevated temperature to afford compounds of formula xxiv (Method S).

Scheme 6: Alternate route for the synthesis of 3-substituted 4-cyano-5-morpholin-4-ylthiophene-2-carboxamides Scheme 5 above shows a general route for preparing compounds of formula (xxiv). As shown in Scheme 5, xvi is treated with methyl thioacetate in the presence of a suitable base, such as TEA in MeOH under elevated temperature to Scheme 6 above shows an alternate route for preparing compounds of formula (vi). As shown in Scheme 6, amine xx is subjected to Sandmayer reaction using appropriate conditions, such as tert-butyl nitrite and CuBr in ACN to afford bromide xxv (Method T), which is coupled with boronic acids using Suzuki conditions, such as Pd(PPh$_3$)$_4$, in the presence of a suitable base, such as potassium carbonate in DME- EtOH mixture under microvawe irradiation to afford compounds of formula xxvi (Method U), that are transformed to amides vi via acids v as described in methods D and E.

Scheme 7: Alternate route for the synthesis of 3-substituted 4-cyano-5-morpholin-4-ylthiophene-2-carboxamides

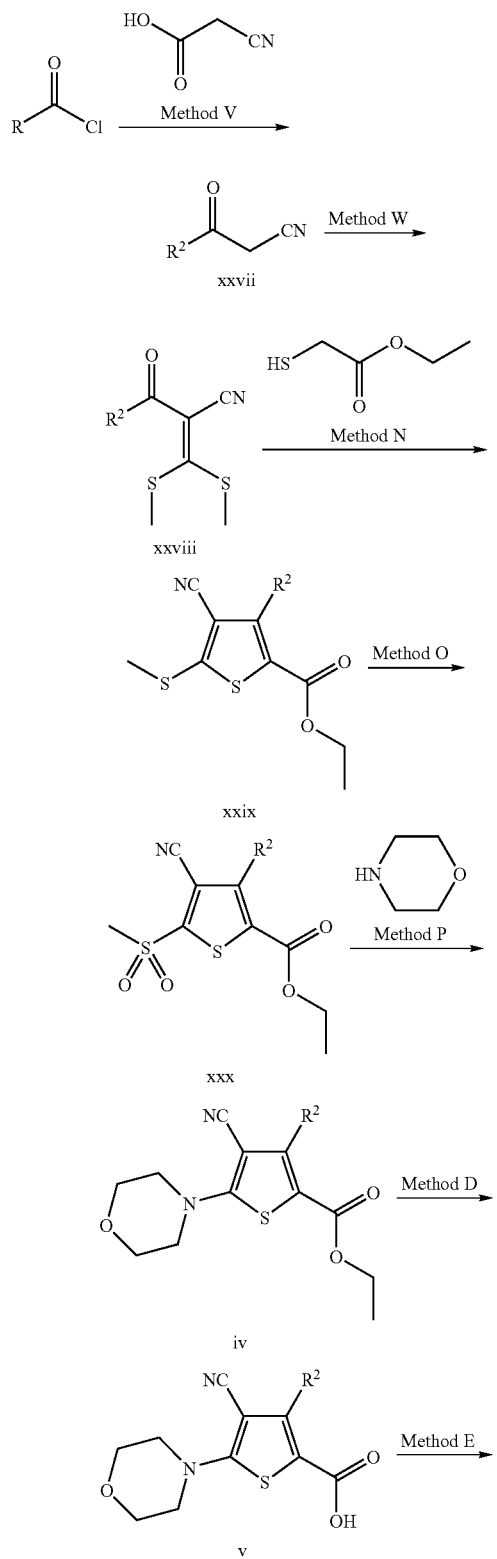

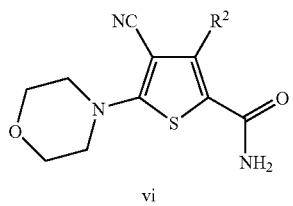

Scheme 7 above shows an alternate route for preparing compounds of formula (vi). As shown in Scheme 7, acyl chlorides are coupled with cyanoacetic acid in the presence of a suitable base, such as n-BuLi in THF at low temperature to afford nitrites xxvii (Method V), that are subjected to reaction with carbon disulfide using a suitable base, such as sodium hydride in DMSO, followed by alkylation with an appropriate reagent, such as MeI to give compounds of formula xxviii (Method W). Treatment of xxviii with ethyl thioacetate, as described in Method N, followed by oxidation, as described in Method 0 gives sulfone xxx. Displacement of sulfone xxx with morpholine as described in Method P gives compounds of formula iv, that are transformed into amides vi using methods D and E.

Scheme 8: General route for the synthesis of N-substituted 4-cyano-3-(aryl)-5-morpholin-4-ylthiophene-2-carboxamides

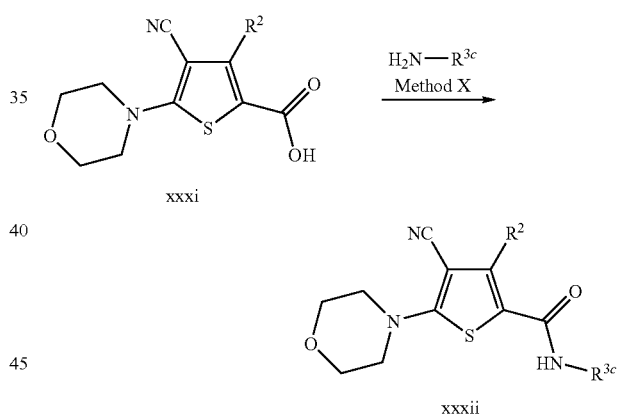

Scheme 8 above shows a general route for preparing compounds of formula (xx-xii). As shown in Scheme 8, carboxylic acid xxxi can be coupled with amines using suitable conditions, such as HBTU, NMO in DMF to afford substituted amides of formula xxxii (Method X).

Scheme 9: Alternative route for the synthesis of N-substituted 4-cyano-3-(aryl)-5-morpholin-4-ylthiophene-2-carboxamides

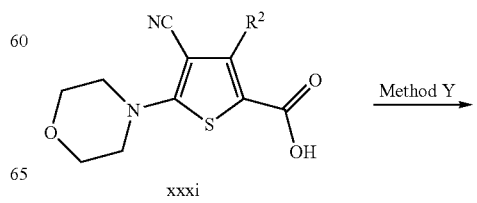

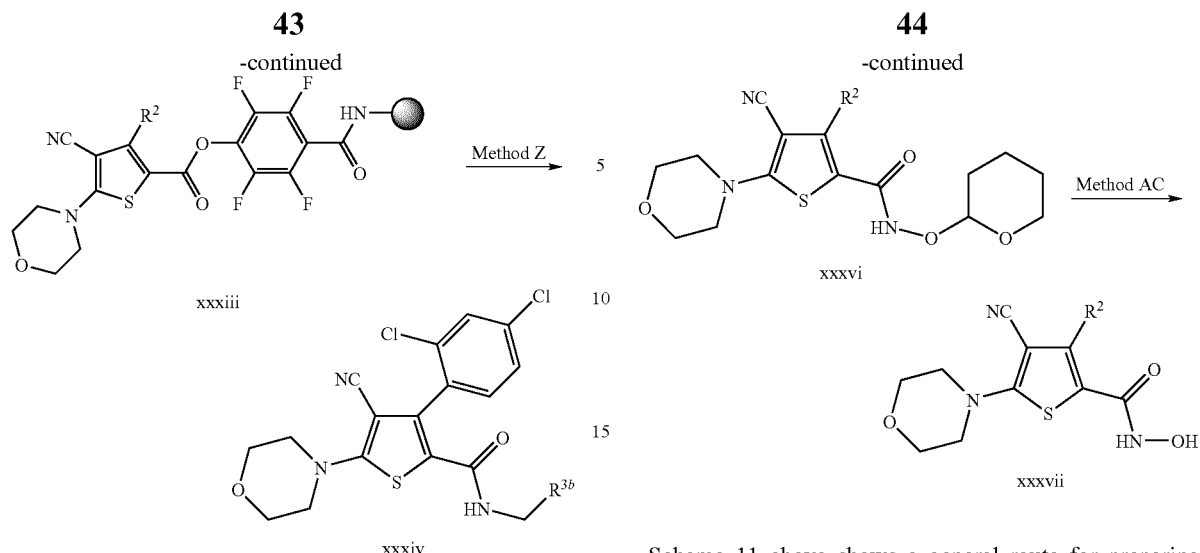

Scheme 9 above shows an alternative route for preparing compounds of formula (xxxiv). Carboxylic acid xxxi forms resin bound activated ester xxxiii (Method Y), that can be coupled with substituted benzylamines to afford substituted amides of formula xxxiv (Method Z).

Scheme 10: General route for the synthesis of N-substituted 4-cyano-3-(aryl)-5-morpholin-4-yl-2-thienyl ureas

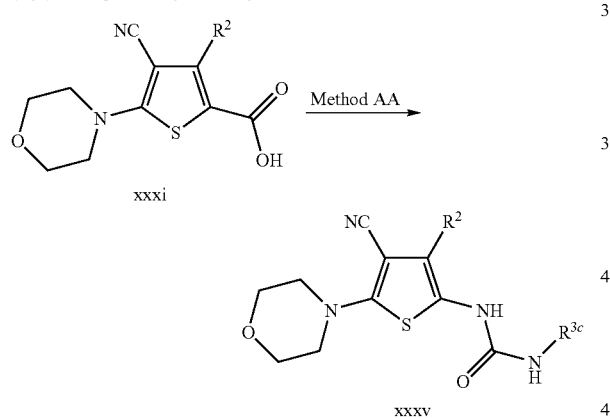

Scheme 10 above shows a general route for preparing compounds of formula (xxxv). As shown in Scheme 10, carboxylic acid xxxi can be treated with DPPA, or other suitable reagent in toluene under elevated temperature to form an intermediate isocyanate and subsequently treat with amines in the presence of suitable base, such as TEA to afford ureas of formula xxxv (Method AA).

Scheme 11: General route for the synthesis of 4-Cyano-3-aryl-N-hydroxy-5-morpholin-4-yl-thiophene-2-carboxamides

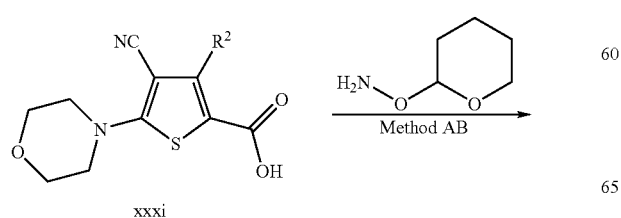

Scheme 11 above shows a general route for preparing compounds of formula (xxvvii). As shown in Scheme 11, carboxylic acid xxxi can be coupled with O-(Tetrahydropyran-2-yl)hydroxylamine using suitable conditions, such as HATU, iPr$_2$NEt in DMF to afford substituted hydroxylamines of formula xxxvi (Method B), that can be deprotected using an appropriate reagent, such as TFA in DCM to afford hydroxamic acids of formula xxxvii (Method AC).

Scheme 12: Alternative route for the synthesis of substituted 4-cyano-3-aryl-5-(morpholine-4-yl)thiophene-2-carboxamides

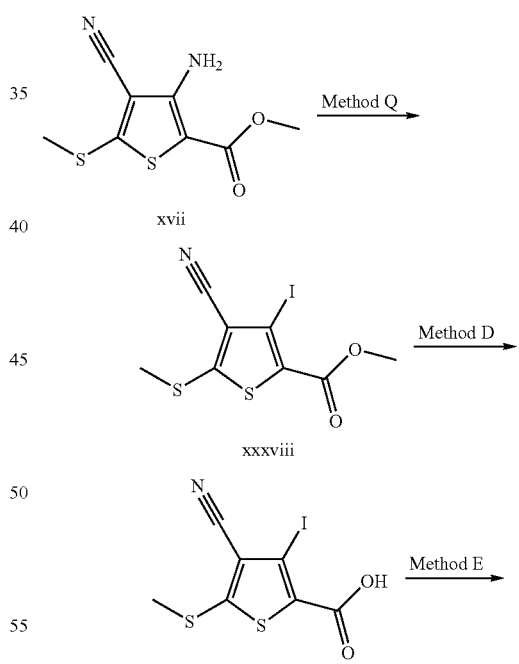

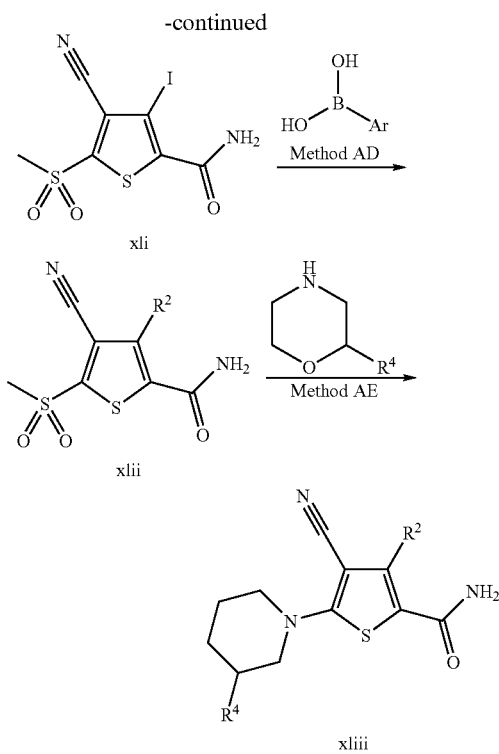

Scheme 12 above shows a general route for preparing compounds of formula (xliii). As shown in Scheme 12, amine xvii is treated with isoamyl nitrite, or other suitable reagent in acetonitrile followed by a halogen source, such as methylene iodide to afford iodothiophene xxxviii (Method Q). Hydrolysis of the ester can be achieved using a suitable base, such as sodium hydroxide in aqueous conditions, to give carboxylic acid xxxix (Method D). Formation of amide xl is done using an appropriate coupling reagent, such as EDCI and HOBT in DCM followed by treatment with aqueous ammonia (Method E). Thioether xl can be oxidized to sulfone xli using a suitable oxidant, such as mCPBA in DCM (Method O). The latter compound is subjected to Suzuki coupling conditions with an appropriate combination of aryl boronic acid, Pd source, such as Pd(dba)$_2$, ligand, such as dpePhos, and a base, such as potassium phosphate in DME/DMA solvent mixture under microwave irradiation to afford advanced intermediate of formula xlii (Method AD). Treatment of sulfones xlii with neat substituted morpholines under elevated temperature affords amides of formula xliii (Method AE).

4. Uses, Formulation and Administration

As discussed above, the present invention provides compounds that are useful as inhibitors of PI3K enzymes, and thus the present compounds are useful for treating proliferative, inflammatory, or cardiovascular disorders such as tumor and/or cancerous cell growth mediated by PI3K. In particular, the compounds are useful in the treatment of cancers in a subject, including, but not limited to, lung and bronchus, prostate, breast, pancreas, colon and recum, thyroid, liver and intrahepatic bile duct, hepatocellular, gastric, glioma/glioblastoma, endometrial, melanoma, kidney, and renal pelvis, urinary bladder, utering corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, melanoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PI3K.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithini, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PI3K. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/ or salts thereof are used in combination with pharmaceutically acceptable carriers to treat disorders, symptoms and diseases where PI3K kinase plays a role.

EXPERIMENTAL PROCEDURES

I. Preparation of Exemplary Compounds

Definitions

AcOH acetic acid
ACN acetonitrile
ATP adenosine triphosphate
BCA bicinchoninic acid
BSA bovine serum albumin
BOC tert-butoxycarbonyl
M-CPBA m-chloroperbenzoic acid
DCE dichloroethane
DCM dichloromethane
DDQ 2,3-dichloro-5,6-dicyano-1,4-benzoquinone
DIPEA diisopropylethyl amine
DMEM Dulbecco's Modified Eagle's Medium
DMF N,N-dimethylformamide
DMSO dimethylsulfoxide
DPPA diphenylphosphoryl azide
DTT dithiothreitol
dppf diphenylphosphinoferrocene
EDCI N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
h hours
HATU N,N,N',N'-tetramethyl-o-(7-azabenzotriazole-1-yl) uronium hexafluorophosphate
HBTU o-benzotriazol-1-yl-N,N, N',N'-tetramethyluronium hexafluorophosphate
HEPES N-(2-Hydroxyethyl)piperazine-N'-(2-ethanesulfonic acid)
HOBT 1-hydroxybenztriazole hydrate
HRMS high resolution mass spectrum
LAH lithium aluminum hydride
LCMS liquid chromatography mass spectrum
m/z mass to charge
Me methyl
MeOH methanol
min minutes
MS mass spectrum
MTT methylthiazoletetrazolium
MWI microwave irradiation PBS phosphate buffered saline
PKA cAMP-dependent protein kinase rt room temperature
TEA triethylamine
TFFA trifluoroacetic anhydride
THF tetrahydrofuran
TMB 3,3',5,5'-Tetramethylbenzidine
WST (4-[3-(4-iodophenyl)-2-(4-nitrophenyl)-2H-5-tetrazolio]-1,3-benzene disulfonate sodium salt)
Analytical LC-MS Methods
LCMS Conditions Spectra were run on a Phenominex Luna 5 µm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

Example 1

Synthesis of 4-cyano-3-(2,4-dichlorophenyl)-5-morpholin-4-ylthiophene-2-carboxamide (48)

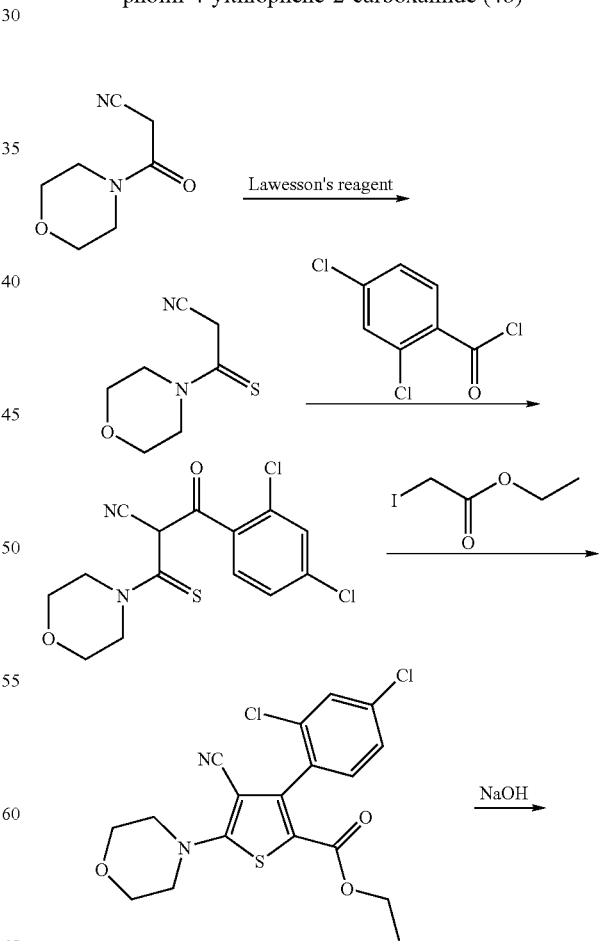

78

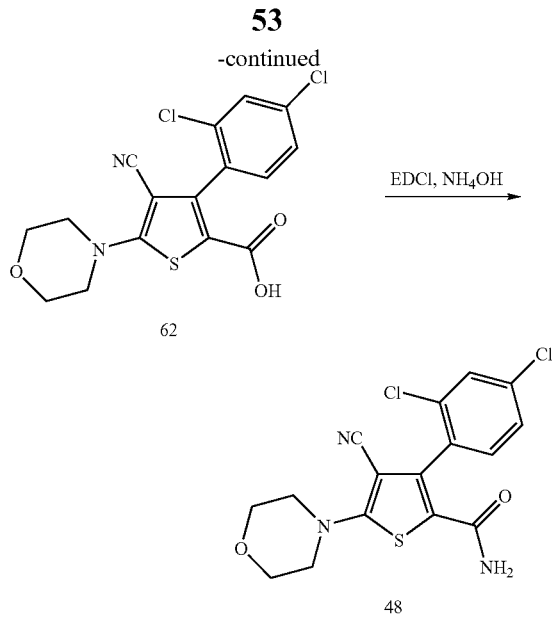

4-cyano-3-(2,4-dichlorophenyl)-5-morpholin-4-ylthiophene-2-carboxylic acid (62) (0.034 g, 62%). LCMS: (FA) ES+ 382.9. $^1$H NMR (400 MHz, d$_6$-DMSO) δ: 7.75 (d, 1H), 7.50 (dd, 1H), 7.39 (d, 1H), 3.74-79 (m, 4H) and 3.55-61 (m, 4H).

Step 5: 4-cyano-3-(2,4-dichlorophenyl)-5-morpholin-4-ylthiophene-2-carboxamide (48)

4-Cyano-3-(2,4-dichlorophenyl)-5-morpholin-4-ylthiophene-2-carboxylic acid (0.050 g, 0.13 mmol), HOBT (0.037 g, 0.274 mmol) and EDCI (50 mg, 0.261 mmol) were suspended in DCM (6.5 mL). After 30 min the reagents dissolved. To the resulting solution was added concentrated aqueous ammonia (0.26 mL, 6.5 mmol) and the solution was allowed to stir vigorously at rt overnight. The reaction mixture was concentrated and the residue was diluted with 1N HCl and extracted with EtOAc. The organic solutions were combined, washed with sat NaHCO$_3$ and brine, dried over MgSO$_4$ filtered and concentrated to give a brown solid. The solid was triturated with hexanes and cold EtOAc to give 4-cyano-3-(2,4-dichlorophenyl)-5-morpholin-4-ylthiophene-2-carboxamide (48) (0.024 g, 49%). LCMS: (AA) ES+ 382, ES– 380. $^1$H NMR (400 MHz, d$_6$-DMSO) δ: 7.78 (s, 1H), 7.54 (d, 2H), 7.43 (d, 2H), 3.77-3.79 (m, 4H) and 3.52-3.55 (m, 4H).

Compounds in the following table were prepared from the appropriate starting materials in a method analogous to that of Example 1:

| | |
|---|---|
| 34 | LCMS: (AA) ES+ 349.1. |
| 52 | LCMS: (AA) ES+ 363.0. |
| 51 | LCMS: (FA) ES+ 349.2. |
| 81 | LCMS: (AA) ES+ 394. |
| 36 | LCMS: (FA) ES+ 410. |
| 21 | LCMS: (AA) ES+ 408. |
| 74 | LCMS: (AA) ES+ 451. |
| 16 | LCMS: (AA) ES+ 440. |
| 55 | LCMS: (FA) ES+ 333.1. |
| 59 | LCMS: (FA) ES+ 333.6. |
| 6 | LCMS: (AA) ES+ 332.1. |
| 27 | LCMS: (FA) ES+ 383.2. |
| 79 | LCMS: (FA) ES+ 315.1. |
| 54 | LCMS: (FA) ES+ 396. |
| 72 | LCMS: (FA) ES+ 472. |

Example 2

Synthesis of N-[4-cyano-3-(2,4-dichlorophenyl)-5-morpholin-4-yl-2-thienyl]urea (28)

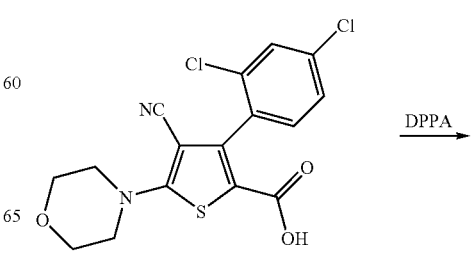

Example 3

Synthesis of 4-cyano-3-(4-methoxyphenyl)-5-morpholin-4-ylthiophene-2-carboxamide (66)

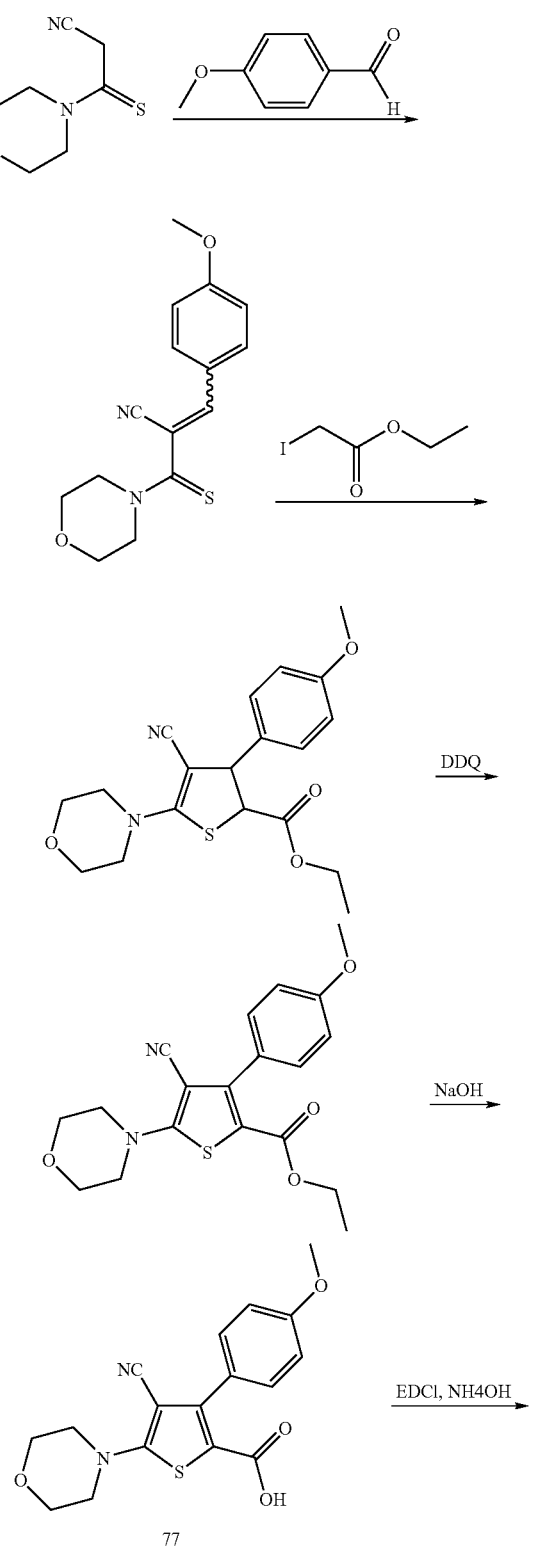

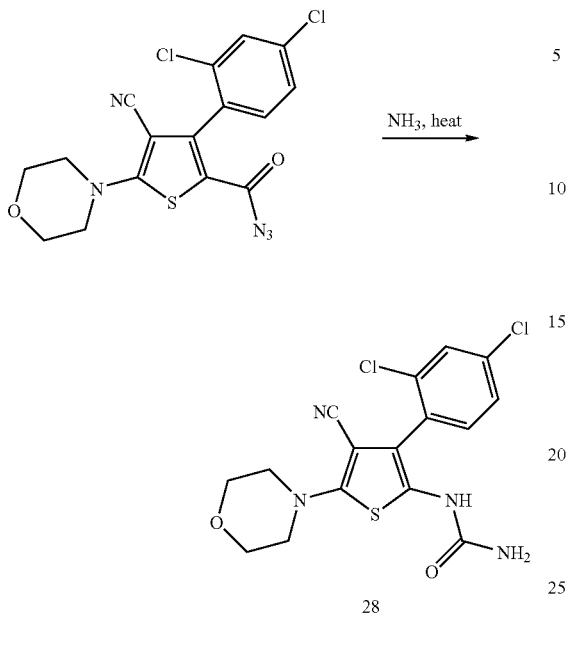

Step 1: 4-cyano-3-(2,4-dichlorophenyl)-5-morpholin-4-ylthiophene-2-carbonyl azide To a solution of 4-cyano-3-(2,4-dichlorophenyl)-5-morpholin-4-ylthiophene-2-carboxylic acid (0.38 g, 0.99 mmol) and TEA (0.414 mL, 2.97 mmol) in anhydrous THF (15 mL) was added diphenylphosphoryl azide (0.341 mL, 1.58 mmol) in one portion, under nitrogen. The reaction mixture was allowed to stir at rt overnight, and was concentrated. The residue was purified by column chromatography to give 4-cyano-3-(2,4-dichlorophenyl)-5-morpholin-4-ylthiophene-2-carbonyl azide (0.318 g, 79%).

Step 2: N-[4-cyano-3-(2,4-dichlorophenyl)-5-morpholin-4-yl-2-thienyl]urea (28)

A mixture of 4-cyano-3-(2,4-dichlorophenyl)-5-morpholin-4-ylthiophene-2-carbonyl azide (0.050 g, 0.122 mmol) and a 0.5 M solution of ammonia in dioxane (2.45 mL, 1.22 mmol) were heated at 70° C. for 2 h under nitrogen. The mixture was concentrated and the residue was purified by column chromatography to give N-[4-cyano-3-(2,4-dichlorophenyl)-5-morpholin-4-yl-2-thienyl]urea (28) (0.035 g, 73%). LCMS: (FA) ES+ 397, ES− 395. $^1$H NMR (400 MHz, $d_6$-DMSO) δ: 8.48 (s, 1H), 7.81 (s, 1H), 7.55 (d, 10H), 7.41 (d, 1H), 6.18 (s, 2H) and 3.73-3.75 (m, 4H).

Compounds in the following table were prepared from the appropriate starting materials in a method analogous to that of Example 2:

| | |
|---|---|
| 11 | LCMS: (FA) ES+ 397.2 ES− 395.2. |
| 64 | LCMS: (FA) ES+ 474.4 |

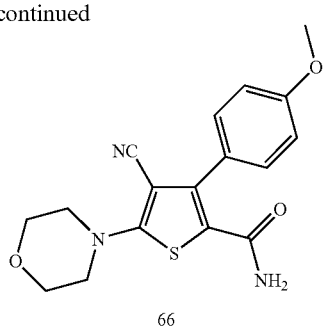

66

Step 1: 3-(4-methoxyphenyl)-2-(morpholin-4-ylcarbonothioyl)acrylonitrile

A solution of 3-morpholin-4-yl-3-thioxopropanenitrile (0.122 g, 0.72 mmol) and p-anisaldehyde (0.1 mL, 0.86 mmol) in 10% piperidine/ethanol (5.5 mL) was allowed to stir at 50° C. under nitrogen for 3.5 h. The reaction mixture was concentrated and the residue was diluted with 10% citric acid solution and extracted with EtOAc. The organic solutions were combined, washed with sat NaHCO$_3$ and brine, dried over MgSO$_4$, filtered and concentrated to give 3-(4-methoxyphenyl)-2-(morpholin-4-ylcarbonothioyl)acrylonitrile. The crude product was a mixture of stereoisomers and was used directly in the next step. LCMS: (AA) ES+ 289.

Step 2: ethyl 4-cyano-3-(4-methoxyphenyl)-5-morpholin-4-yl-2,3-dihydrothiophene-2-carboxylate A mixture of 3-(4-methoxyphenyl)-2-(morpholin-4-ylcarbonothioyl)acrylonitrile (from step 1), ethyl iodoacetate (0.25 mL, 2.1 mmol) and DIPEA (0.5 mL, 2.9 mmol) was dissolved in ACN (2 mL) and subjected to MWI at 150° C. for 10 min. The mixture was allowed to cool and was concentrated. The residue was diluted with 5% sodium bisulfite solution and extracted with EtOAc. The organic solutions were combined, washed with sat NaHCO$_3$ and brine, dried over MgSO$_4$, filtered and concentrated. The residue was purified by column chromatography to give ethyl 4-cyano-3-(4-methoxyphenyl)-5-morpholin-4-yl-2,3-dihydrothiophene-2-carboxylate (0.168 g, 63% over two steps). LCMS: (AA) ES+ 375, ES− 373.

Step 3: ethyl 4-cyano-3-(4-methoxyphenyl)-5-morpholin-4-ylthiophene-2-carboxylate To a solution of ethyl 4-cyano-3-(4-methoxyphenyl)-5-morpholin-4-yl-2,3-dihydrothiophene-2-carboxylate (0.168 g, 0.45 mmol) in toluene (5 mL) was added 2,3-dichloro-5,6-dicyano-1,4-benzoquinone (0.102 g, 0.45 mmol). The mixture was allowed to stir at 90° C. for 90 min and allowed to cool before filtration through Celite, eluting with toluene. The filtrate was concentrated and the residue was purified by column chromatography. The resulting orange solid was recrystallized from ethyl acetate/40-60 petroleum ether to give ethyl 4-cyano-3-(4-methoxyphenyl)-5-morpholin-4-ylthiophene-2-carboxylate (0.11 g, 66%). LCMS: (FA) ES+ 373. $^1$H NMR (400 MHz, d$_6$-DMSO) δ: 7.28-7.31 (m, 2H), 6.96-7.00 (m, 2H), 4.06 (q, 2H), 3.81 (s, 3H), 3.76-3.79 (m, 4H), 3.59-3.61 (m, 4H) and 1.08 (t, 3H).

Step 4: 4-cyano-3-(4-methoxyphenyl)-5-morpholin-4-ylthiophene-2-carboxylic acid (77)

To a suspension of ethyl 4-cyano-3-(4-methoxyphenyl)-5-morpholin-4-ylthiophene-2-carboxylate (0.077 g, 0.21 mmol) in THF/MeOH/water (1:1:1) (6 mL) was added sodium hydroxide (0.2 g, 5 mmol). The reaction mixture was allowed to stir at 50° C. for 6 h and was concentrated. The residue was acidified to pH 1-2 with 1N HCl and was extracted with EtOAc. The organic solutions were combined, washed with brine, dried over MgSO$_4$, filtered and concentrated to give 4-cyano-3-(4-methoxyphenyl)-5-morpholin-4-ylthiophene-2-carboxylic acid (77) (0.061 g, 86%). LCMS: (FA) ES+ 345. $^1$H NMR (400 MHz, d$_6$-DMSO) δ: 7.27-7.31 (m, 2H), 6.95-6.99 (m, 2H), 3.80 (s, 3H), 3.76-3.78 (m, 4H) and 3.56-3.58 (m, 4H).

Step 5: 4-cyano-3-(4-methoxyphenyl)-5-morpholin-4-ylthiophene-2-carboxamide (66)

4-Cyano-3-(4-methoxyphenyl)-5-morpholin-4-ylthiophene-2-carboxylic acid (0.035 g, 0.10 mmol), HOBT (0.028 g, 0.18 mmol) and EDCI (38 mg, 0.20 mmol) were suspended in DCM (5 mL). After 50 min the reagents dissolved. To the resulting solution was added concentrated aqueous ammonia (0.2 mL, 5 mmol) and the solution was allowed to stir vigorously at rt for 2 h. The reaction mixture was concentrated and the residue was diluted with 1N HCl and extracted with EtOAc. The organic solutions were combined, washed with sat NaHCO$_3$ and brine, dried over MgSO$_4$ filtered and concentrated to give 4-cyano-3-(4-methoxyphenyl)-5-morpholin-4-ylthiophene-2-carboxamide (66) (0.028 g, 80%). LCMS: (AA) ES+ 344. $^1$H NMR (400 MHz, d$_6$-DMSO) δ: 7.32-7.35 (m, 2H), 7.06-7.09 (m, 2H), 3.82 (s, 3H), 3.76-3.78 (m, 4H) and 3.52-3.54 (m, 4H).

Compounds in the following table were prepared from the appropriate starting materials in a method analogous to that of Example 3:

| | |
|---|---|
| 73 | LCMS: (FA) ES+ 375. |
| 80 | LCMS: (FA) ES+ 374. |
| 8 | LCMS: (FA) ES+ 345. |
| 33 | LCMS: (FA) ES+ 343. |
| 20 | LCMS: (AA) ES+ 349. |

Example 4

Synthesis of 3-[(2-chlorophenyl)(hydroxy)methyl]-4-cyano-5-morpholin-4-ylthiophene-2-carboxylic acid (61)

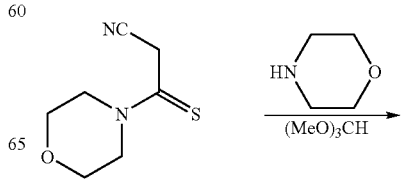

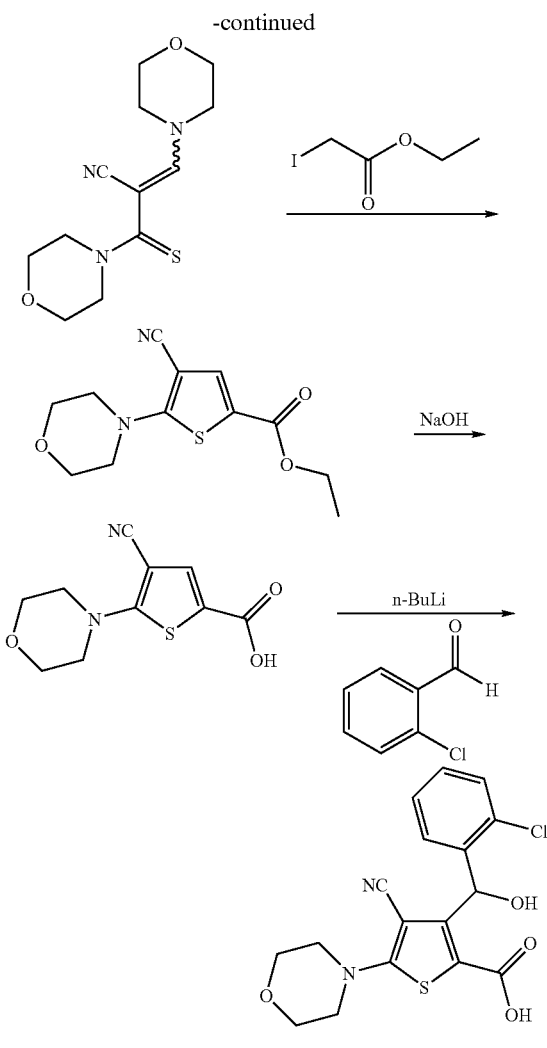

61

Step 1: 3-morpholin-4-yl-2-(morpholin-4-ylcarbonothioyl)acrylonitrile

To a solution of 3-morpholin-4-yl-3-thioxopropanenitrile (0.1 g, 0.59 mmol) in triethylorthoformate (0.245 mL, 1.48 mmol) was added morpholine (0.064 mL, 0.73 mmol). The reaction mixture was subjected to MWI at 150° C. for 10 min. The reaction mixture was concentrated to small volume until the product precipitated. The precipitate was filtered off, washed with MeOH and isohexane to give 3-morpholin-4-yl-2-(morpholin-4-ylcarbonothioyl)acrylonitrile (0.13 g, 83%). LCMS: (AA) ES+ 268.2. $^1$H NMR (400 MHz, d$_6$-DMSO) δ: 3.96 m, 4H) and 3.67-3.78 (m, 12H).

Step 2: ethyl 4-cyano-5-morpholin-4-ylthiophene-2-carboxylate

A mixture of 3-morpholin-4-yl-2-(morpholin-4-ylcarbonothioyl)acrylonitrile (0.07 g, 0.26 mmol), ethyl iodoacetate (0.034 mL, 0.29 mmol) and DIPEA (0.091 mL, 0.52 mmol) in ACN (0.55 mL) was subjected to MWI at 120° C. for 10 min. The crystals formed upon cooling were filtered, washed with cold MeOH and diethyl ether to give ethyl 4-cyano-5-morpholin-4-ylthiophene-2-carboxylate (0.06 g, 87%). LCMS: (AA) ES+ 267.1. $^1$H NMR (400 MHz, CDCl$_3$) δ: 7.62 s, 1H), 4.30 (q, 2H), 3.85-3.87 (m, 4H), 3.58-3.60 (m, 4H) and 1.34 (t, 3H).

Step 3: 4-cyano-5-morpholin-4-ylthiophene-2-carboxylic acid

To a solution of ethyl 4-cyano-5-morpholin-4-ylthiophene-2-carboxylate (0.06 g, 0.23 mmol) in THF/MeOH/water (3:1:1) (5 mL) was added sodium hydroxide (0.095 g, 2.3 mmol). The reaction mixture was allowed to stir at rt for 20 h and was concentrated. The residue was acidified to pH 1-2 with 1N HCl and was extracted with EtOAc. The organic solutions were combined, washed with brine, dried over MgSO$_4$, filtered and concentrated to give 4-cyano-5-morpholin-4-ylthiophene-2-carboxylic acid (0.048 g, 88%). LCMS: (FA) ES+ 239.1. $^1$H NMR (400 MHz, d$_6$-DMSO) δ:7.67 s, 1H), 3.72-3.75 (m, 4H) and 3.52-3.55 (m, 4H).

Step 4: 3-[(2-chlorophenyl)(hydroxy)methyl]-4-cyano-5-morpholin-4-ylthiophene-2-carboxylic acid (61)

A solution of 4-cyano-5-morpholin-4-ylthiophene-2-carboxylic acid (0.1 g, 0.42 mmol) in anhydrous THF (1.5 mL) was cooled down to −70° C. To this cooled solution was added a 2.5 M solution of n-butyl lithium in hexanes (0.672 mL, 1.68 mmol) dropwise under nitrogen. The resulting solution was stirred at −70° C. for 2 h and 2-chlorobenzaldehyde (0.142 mL, 1.26 mmol) was added. The reaction mixture was stirred at −70° C. for a further 2 h and was quenched with water. The mixture was concentrated to a small volume and the aqueous residue was washed with EtOAc. The aqueous solution was separated, acidified with 1N HCl and extracted with EtOAc. The organic solutions were combined, washed with brine, dried over MgSO$_4$, filtered and concentrated. The crude material was purified by column chromatography to give 3-[(2-chlorophenyl)(hydroxy)methyl]-4-cyano-5-morpholin-4-ylthiophene-2-carboxylic acid (61) (0.03 g, 19%). LCMS: (FA) ES+ 319.0. $^1$H NMR (400 MHz, d$_6$-DMSO) δ: 7.39-7.41 m, 1H), 7.31-7.33 (m, 1H), 7.23-7.27 (m, 2H), 6.19 (s, 1H), 5.74 (s, 1H), 3.70-3.72 m, 4H) and 3.38-3.40 (m, 4H).

Compounds in the following table were prepared from the appropriate starting materials in a method analogous to that of Example 4:

| 23 | LCMS: (FA) ES− 349. |
| 38 | LCMS: (FA) ES+ 377. |

Example 5

Synthesis of 3-(4-chlorophenyl)-4-cyano-N-methyl-5-morpholin-4-ylthiophene-2-carboxamide (69)

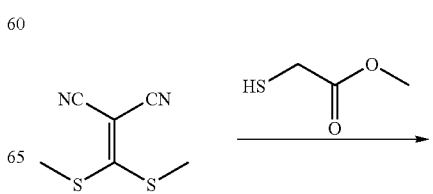

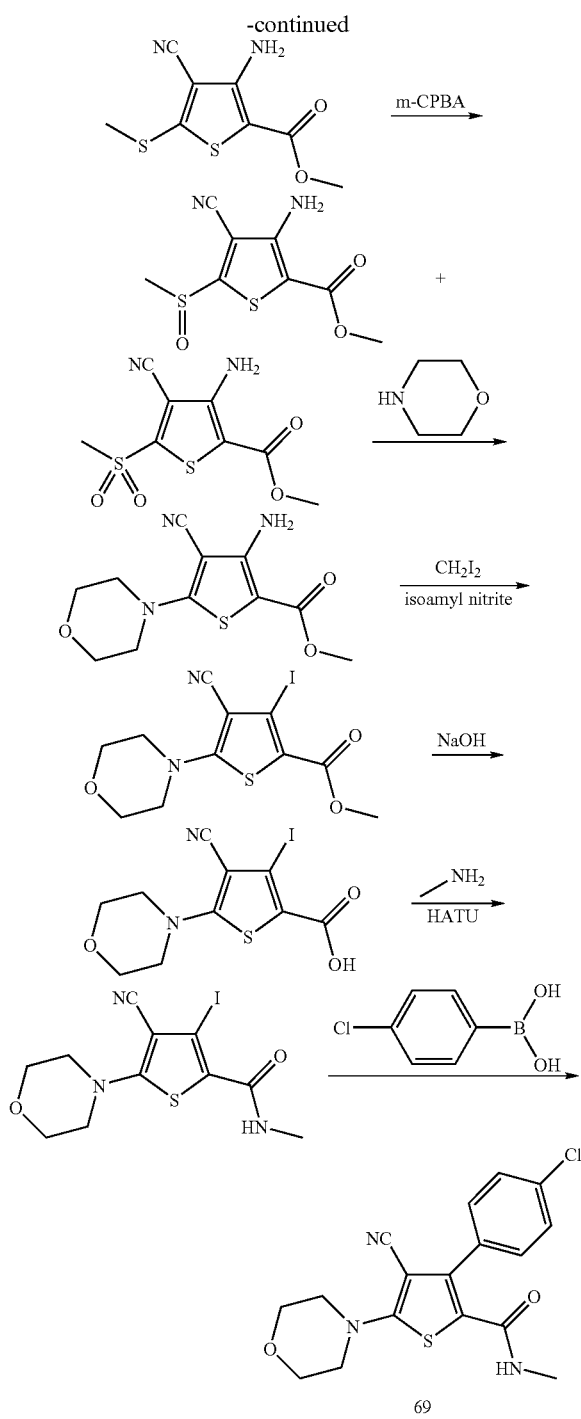

99%). LCMS: (AA) ES+ 229.2. $^1$H NMR (400 MHz, d$_6$-DMSO) δ: 3.74 s, 3H) and 2.70 (s, 3H).

Step 2: methyl 3-amino-4-cyano-5-(methylsulfinyl) thiophene-2-carboxylate and methyl 3-amino-4-cyano-5-(methylsulfonyl)thiophene-2-carboxylate A suspension of methyl 3-amino-4-cyano-5-(methylsulfanyl)thiophene-2-carboxylate (40 g, 180 mmol) and m-CPBA (120 g, 700 mmol) in DCM (450 mL) was allowed to stir at reflux for 1 h. The reaction mixture was allowed to cool to rt and the precipitate was filtered, washed with DCM, with sat NaHCO$_3$, with water and was dried in vaccuo to give a mixture of methyl 3-amino-4-cyano-5-(methylsulfinyl) thiophene-2-carboxylate and methyl 3-amino-4-cyano-5-(methylsulfonyl)thiophene-2-carboxylate (35 g) which was carried through to the next step. LCMS: (FA) ES+ 245.1 (peak 1) and 261.0 (peak 2). $^1$H NMR (400 MHz, d$_6$-DMSO) δ: 7.05 (s, 2H), 6.95 (s, 2H), 3.79 (s, 3H), 3.75 (s, 3H), 3.45 (s, 3H) and 3.03 (s, 3H).

Step 3: methyl 3-amino-4-cyano-5-morpholin-4-ylthiophene-2-carboxylate

A mixture of methyl 3-amino-4-cyano-5-(methylsulfinyl) thiophene-2-carboxylate/methyl 3-amino-4-cyano-5-(methylsulfonyl)thiophene-2-carboxylate (35 g, 134 mmol) and morpholine (70.4 mL) in THF (350 mL) was allowed to stir at reflux for 3 h. The reaction mixture was allowed to cool overnight and was concentrated to yield an oil which was triturated with diethyl ether. A precipitate formed and was filtered, washed with sat NaHCO$_3$ and water to give methyl 3-amino-4-cyano-5-morpholin-4-ylthiophene-2-carboxylate (35.7 g, 99%). LCMS: (AA) ES+ 268.0. $^1$H NMR (400 MHz, d$_6$-DMSO) δ: 6.65 (s, 2H), 3.69-3.81 (m, 4H), 3.70 (s, 3H) and 3.50-3.62 (m, 4H).

Step 4: methyl 4-cyano-3-iodo-5-morpholin-4-ylthiophene-2-carboxylate

To a solution of methyl 3-amino-4-cyano-5-morpholin-4-ylthiophene-2-carboxylate (3.4 g, 12.6 mmol) in ACN (110 mL) was added diiodomethane (10.5 mL, 130.2 mmol) and amyl nitrite (1.1 mL, 77.7 mmol). The reaction mixture was allowed to stir at 80° C. for 4 days and was concentrated. The residue was purified by column chromatography to give methyl 4-cyano-3-iodo-5-morpholin-4-ylthiophene-2-carboxylate (2.2 g, 46%). LCMS: (FA) ES+ 379.0. $^1$H NMR (400 MHz, d$_6$-DMSO) δ: 3.76 (s, 3H), 3.72-3.75 (m, 4H) and 3.56-3.61 (m, 4H).

Step 5: 4-cyano-3-iodo-5-morpholin-4-ylthiophene-2-carboxylic acid

To a solution of methyl 4-cyano-3-iodo-5-morpholin-4-ylthiophene-2-carboxylate (1.5 g, 40.1 mmol) in THF (110 mL) was added a 1.0 M solution of sodium hydroxide in water (50 mL). The reaction mixture was allowed to stir at rt overnight and was then allowed to settle. The two layers were separated and the aqueous solution was washed with EtOAc and acidified with 1 N HCl. A precipitate formed and was filtered to give 4-cyano-3-iodo-5-morpholin-4-ylthiophene-2-carboxylic acid (1.2 g, 82%). LCMS: (FA) ES+ 365.0, ES− 363.1. $^1$H NMR (400 MHz, d$_6$-DMSO) δ: 3.71-3.78 (m, 4H) and 3.51-3.58 (m, 4H).

Step 1: methyl 3-amino-4-cyano-5-(methylsulfanyl) thiophene-2-carboxylate

A mixture of [bis(methylsulfanyl)methylene]malononitrile (40 g, 230 mmol), methylthioglycolate (21 mL, 230 mmol) and TEA (24 mL, 173 mmol) in MeOH (600 mL) was allowed to stir at reflux for 2 h. The reaction mixture was allowed to cool overnight and the precipitate was filtered off, washed with cold MeOH (×3) to give methyl 3-amino-4-cyano-5-(methylsulfanyl)thiophene-2-carboxylate (52.4 g, Step 6: 4-cyano-3-iodo-N-methyl-5-morpholin-4-ylthiophene-2-carboxamide To a solution of 4-cyano-3-iodo-5-morpholin-4-ylthiophene-2-carboxylic acid (7.1 g, 19.4 mmol) in DMF (195 mL) were added HATU (8.9 g, 23.4 mmol) and DIPEA (4.1 mL, 23.3 mmol). The reaction mixture was allowed to stir at rt for 1 h and a 2.0 M solution of methylamine in THF (19.4 mL, 38.8 mmol) was added. The reaction mixture was allowed to stir at rt for 30 min and water was added. A precipitate formed and was filtered and dried to give 4-cyano-3-iodo-N-methyl-5-morpholin-4-ylthiophene-2-carboxamide (6.4 g, 87%). LCMS: (FA) ES+ 378.0, ES− 376.1. $^1$H NMR (400 MHz, $d_6$-DMSO) δ: 7.92 (m, 1H), 3.72-3.76 (m, 4H), 3.47-3.51 (m, 4H) and 2.73 (d, 3H).

Step 7: 3-(4-chlorophenyl)-4-cyano-N-methyl-5-morpholin-4-ylthiophene-2-carboxamide (69)

A mixture of 4-cyano-3-iodo-N-methyl-5-morpholin-4-ylthiophene-2-carboxamide (0.055 g, 0.14 mmol), 4-chlorophenylboronic acid (0.046 g, 0.29 mmol), tetrakis(triphenylphosphine)palladium(0) (0.017 g, 0.014 mmol) and sodium carbonate (0.046 g, 0.44 mmol) in 1,2-dimethoxyethane (0.71 mL) and water (0.37 mL) was allowed to stir at 80° C. overnight. The reaction mixture was quenched with water and extracted with EtOAc. The organic solutions were combined, washed with brine, dried over $MgSO_4$, filtered and concentrated. The crude material was purified by column chromatography to give 3-(4-chlorophenyl)-4-cyano-N-methyl-5-morpholin-4-ylthiophene-2-carboxamide (69) (0.030 g, 57%).

LCMS: (FA) ES+ 362.2, ES− 360.2. $^1$H NMR (300 MHz, $d_6$-DMSO) δ: 7.52 (d, 2H), 7.36 (d, 2H), 3.74-3.79 (m, 4H), 3.48-3.53 (m, 4H) and 2.54 (d, 3H).

Compounds in the following table were prepared from the appropriate starting materials in a method analogous to that of Example 5:

| | |
|---|---|
| 40 | LCMS: (FA) ES+ 339.2. |
| 13 | LCMS: (FA) ES+ 379.2, ES− 377.1. |
| 44 | LCMS: (FA) ES+ 328.2, ES− 326.2. |
| 12 | LCMS: (FA) ES− 406.1. |
| 10 | LCMS: (FA) ES+ 292.3. |
| 39 | LCMS: (FA) ES+ 376.1, ES− 374.2. |
| 37 | LCMS: (FA) ES+ 346.2. |
| 60 | LCMS: (FA) ES+ 356.3, ES− 354.2. |
| 82 | LCMS: (FA) ES+ 362.2, ES− 360.3. |
| 17 | LCMS: (FA) ES+ 396.1, ES− 394.2. |
| 50 | LCMS: (FA) ES+ 396.2, ES− 394.3. |
| 9 | LCMS: (FA) ES+ 336.3, ES− 334.4. |

Example 6

Synthesis of 4-cyano-3-(4-methylphenyl)-5-morpholin-4-ylthiophene-2-carboxamide (35)

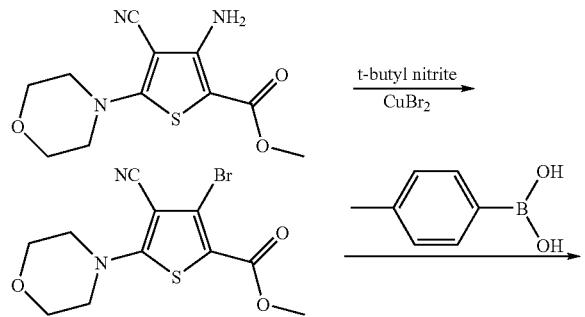

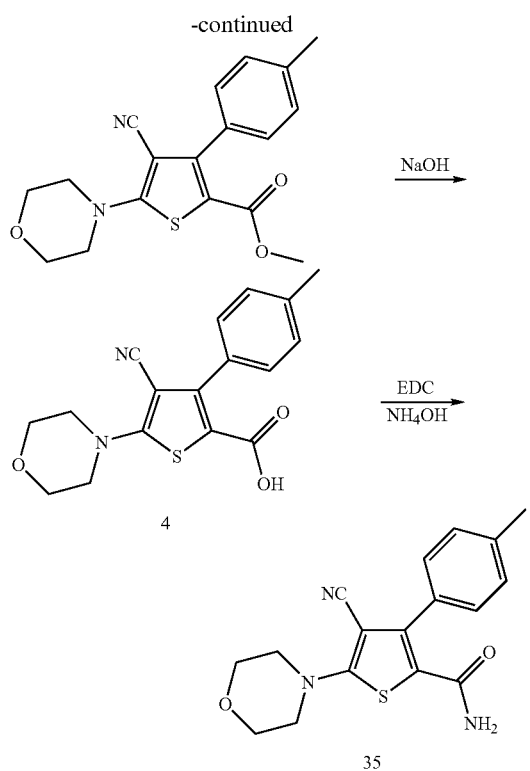

Step 1: methyl 3-bromo-4-cyano-5-morpholin-4-ylthiophene-2-carboxylate

A solution of methyl 3-amino-4-cyano-5-morpholin-4-ylthiophene-2-carboxylate (2.0 g, 7.5 mmol) in anhydrous ACN (30 mL) was cooled to 0° C. To this cooled solution was added tert-butyl nitrite (1.3 mL, 11.3 mmol). The mixture was allowed to stir at 0° C. for 10 min, then a solution of copper (II) bromide (2.0 g, 9.0 mmol) in ACN (10 mL) was added at 0° C. The resulting black solution was allowed to stir at rt for 2 h and was acidified with 2N HCl until complete discoloration. The mixture was neutralised with 2N NaOH, concentrated to a small volume and the aqueous solution was extracted with EtOAc. The organic solutions were combined, washed with water and brine, dried over $MgSO_4$, filtered and concentrated. The residue was purified by column chromatography and triturated with MeOH to give methyl 3-bromo-4-cyano-5-morpholin-4-ylthiophene-2-carboxylate (1.16 g, 47%). LCMS: (AA) ES+ 331.9.

Step 2: methyl 4-cyano-3-(4-methylphenyl)-5-morpholin-4-ylthiophene-2-carboxylate A mixture of methyl 3-bromo-4-cyano-5-morpholin-4-ylthiophene-2-carboxylate (0.040 g, 0.12 mmol), p-tolylboronic acid (0.020 g, 0.14 mmol), tetrakis(triphenylphosphine)palladium(0) (0.004 g, 0.004), 2M aqueous $K_2CO_3$ solution (0.120 mL, 0.24 mmol) in 1,2-dimethoxyethane/EtOH (8/2) (2 mL) was subjected to MWI at 110° C. for 10 min. The reaction mixture was concentrated; the residue was diluted with water and extracted with DCM. The organic solutions were combined, washed with brine, dried over $MgSO_4$, filtered and concentrated. The crude product was purified by column chromatography and triturated with cold MeOH to give methyl 4-cyano-3-(4-methylphenyl)-5-morpholin-4-ylthiophene-2-carboxylate (0.030 g, 83%). LCMS: (AA)

ES+ 343.1. $^1$H NMR (400 MHz, CDCl$_3$) δ: 7.24-7.27 (m, 4H), 3.87-3.89 (m, 4H), 3.69 (s, 3H), 3.60-3.62 (m, 4H) and 2.39 (s, 3H).

Step 3: 4-cyano-3-(4-methylphenyl)-5-morpholin-4-ylthiophene-2-carboxylic acid (4)

To a solution of 4 methyl 4-cyano-3-(4-methylphenyl)-5-morpholin-4-ylthiophene-2-carboxylate (0.060 g, 0.18 mmol) in THF/MeOH/water (2/1/1) (3 mL) was added sodium hydroxide (0.072 g, 1.8 mmol). The reaction mixture was allowed to stir at 50° C. for 3 h and was concentrated. The residue was acidified with 2N HCl and extracted with EtOAc. The organic solutions were combined, washed with brine, dried over MgSO$_4$, filtered and concentrated. The crude product was triturated with diethyl ether and hexanes to give 4-cyano-3-(4-methylphenyl)-5-morpholin-4-ylthiophene-2-carboxylic acid (4) (0.055 g, 93%). LCMS: (FA) ES+ 329.0. $^1$H NMR (400 MHz, d$_6$-DMSO) δ: 7.20-7.23 (m, 4H), 3.76-3.79 (m, 4H), 3.56-3.59 (m, 4H) and 2.35 (s, 3H).

Step 4: 4-cyano-3-(4-methylphenyl)-5-morpholin-4-ylthiophene-2-carboxamide (35)

To a solution of 4-cyano-3-(4-methylphenyl)-5-morpholin-4-ylthiophene-2-carboxylic acid (0.030 g, 0.091 mmol), HOBT (0.024 g, 0.18 mmol) and EDCI (0.035 g, 0.18 mmol) in DCM (1 mL) was added concentrated aqueous ammonia (0.158 mL, 4.5 mmol). The reaction mixture was allowed to stir at rt for 3 h and was concentrated. The residue was diluted with 0.1N HCl and extracted with EtOAc. The organic solutions were combined, washed with sat NaHCO$_3$, brine, dried over MgSO$_4$, filtered and concentrated to give 4-cyano-3-(4-methylphenyl)-5-morpholin-4-ylthiophene-2-carboxamide (35) (0.024 g, 80%). LCMS: (AA) ES+ 328.2. $^1$H NMR (400 MHz, d$_6$-DMSO) δ: 7.45-7.47 (m, 2H), 7.40-7.42 (m, 2H), 3.88-3.90 (m, 4H), 3.64-3.66 (m, 4H) and 2.62 (s, 3H).

Compounds in the following table were prepared from the appropriate starting materials in a method analogous to that of Example 6:

| 1  | LCMS: (FA) ES+ 321.0. |
| 42 | LCMS: (FA) ES+ 372.0. |
| 18 | LCMS: (AA) ES+ 371.2. |
| 47 | LCMS: (FA) ES+ 383.1. |
| 65 | LCMS: (FA) ES+ 348.  |

Example 7

Synthesis of 4-cyano-3-(3,4-dichlorophenyl)-5-morpholin-4-ylthiophene-2-carboxamide (84)

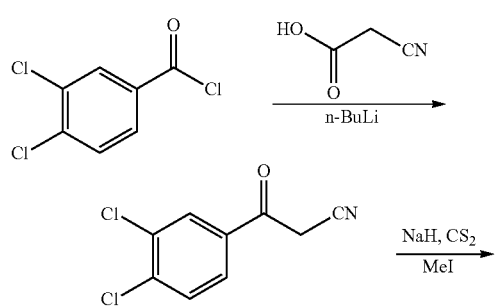

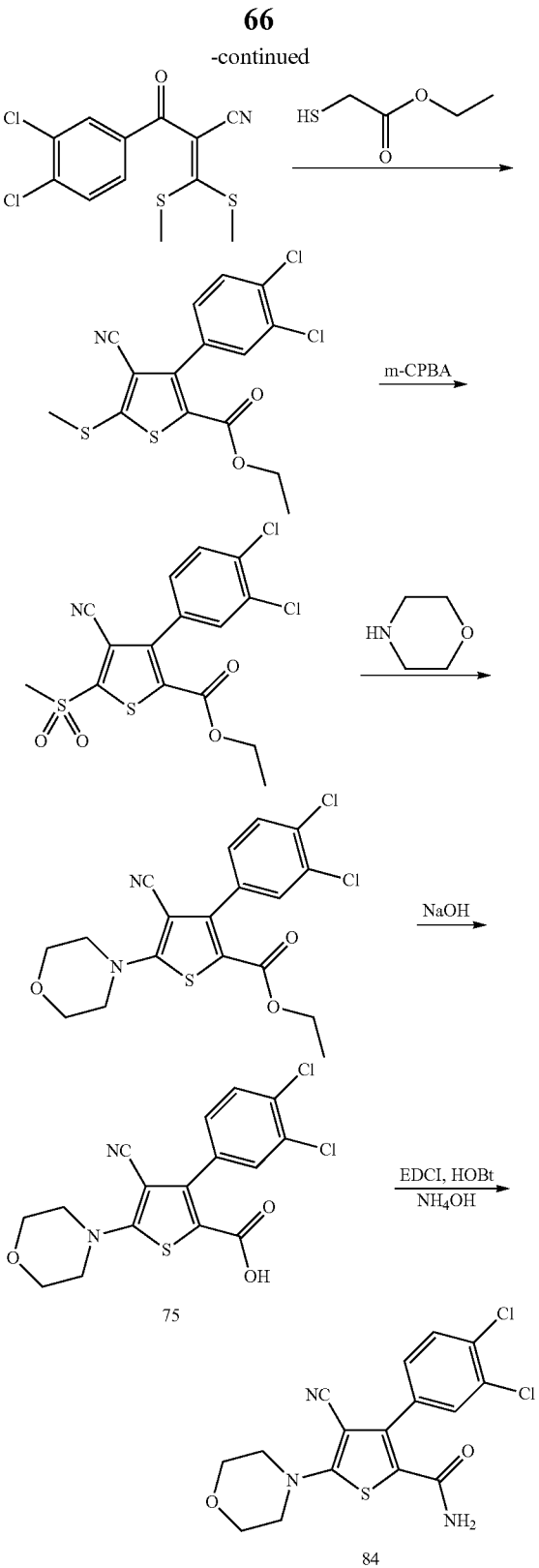

Step 1: 3-(3,4-dichlorophenyl)-3-oxopropanenitrile

To a solution of cyanoacetic acid (4.07 g, 47.8 mmol) in THF (240 mL) cooled to −78° C. under an atmosphere of argon was added 1.6 M n-butyllithium in hexane (59.8 mL). The reaction mixture was stirred for 10 min at −78° C. and was then allowed to warm to 0° C. The reaction mixture was recooled to −78° C. To the mixture was added dropwise 3,4-dichlorobenzoyl chloride (5.01 g, 23.9 mmol) in THF (30 mL). The reaction mixture was allowed to warm to rt. The reaction mixture was diluted with 1N HCl and extracted with EtOAc. The organic solutions were combined, washed with sat NaHCO$_3$, brine, dried over MgSO$_4$, filtered and concentrated. The crude product was purified by column chromatography to give 3-(3,4-dichlorophenyl)-3-oxopropanenitrile (3.9 g, 76%). LCMS: (FA) ES− 212.0. $^1$H NMR (400 MHz, CDCl$_3$) δ: 8.01 (d, 1H), 7.75 (dd, 1H), 7.63 (d, 1H) and 4.05 (s, 2H).

Step 2: 2-(3,4-dichlorobenzoyl)-3,3-bis(methylsulfanyl)acrylonitrile

To a solution of 3-(3,4-dichlorophenyl)-3-oxopropanenitrile (3.3 g, 15.4 mmol) and carbon disulfide (0.927 mL, 15.4 mmol) in DMSO (50 mL) under an atmosphere of argon at 15° C. was added sodium hydride (0.856 g, 033.9 mmol) with vigorous stirring. The reaction mixture was stirred at this temperature for 10 min and was allowed to warm to rt. To the reaction mixture was added methyl iodide (1.92 mL, 30.8 mmol) and the mixture was stirred at rt for 30 min. The reaction mixture was diluted with water and extracted with EtOAc. The organic solutions were combined, washed with brine, dried over MgSO$_4$, filtered and concentrated. The crude product was purified by column chromatography to give 2-(3,4-dichlorobenzoyl)-3,3-bis(methylsulfanyl)acrylonitrile (2.9 g, 59%). LCMS: (FA) ES-318.1. $^1$H NMR (400 MHz, CDCl$_3$) δ: 7.95 (d, 1H), 7.73 (dd, 1H), 7.56 (d, 1H), 2.82 (s, 3H) and 2.55 (s, 3H).

Step 3: ethyl 4-cyano-3-(3,4-dichlorophenyl)-5-(methylsulfanyl)thiophene-2-carboxylate To a stirred suspension of 2-(3,4-dichlorobenzoyl)-3,3-bis(methylsulfanyl)acrylonitrile (2.28 g, 7.16 mmol) in EtOH (31 mL) was added ethyl thioglycolate (0.864 mL, 7.88 mmol) and TEA (1.1 mL, 7.88 mmol). The reaction mixture was heated until reflux was achieved and was then allowed to cool. A solid formed. After sitting at rt overnight, the solid was filtered and washed with cold EtOH (100 mL) to give ethyl 4-cyano-3-(3,4-dichlorophenyl)-5-(methylsulfanyl)thiophene-2-carboxylate (2.38 g, 89%). $^1$H NMR (400 MHz, d$_6$-DMSO) δ: 7.82 (d, 1H), 7.75 (d, 1H), 7.47 (dd, 1H), 4.14 (q, 2H), 2.82 (s, 3H) and 1.11 (t, 3H).

Step 4: ethyl 4-cyano-3-(3,4-dichlorophenyl)-5-(methylsulfonyl)thiophene-2-carboxylate To a stirred slurry of ethyl 4-cyano-3-(3,4-dichlorophenyl)-5-(methylsulfanyl)thiophene-2-carboxylate (2.67 g, 7.17 mmol) in DCM (10 mL) at 0° C. was added slowly m-CPBA (4.95 g, 21.5 mmol). The reaction mixture was allowed to warm to rt and stirred for 20 h. The reaction mixture was diluted with DCM (25 mL) and washed sequentially with 10% NaHSO$_3$, water, sat NaHCO$_3$, and brine. The organic solution was dried over Na$_2$SO$_4$, filtered, and concentrated to give ethyl 4-cyano-3-(3,4-dichlorophenyl)-5-(methylsulfonyl)thiophene-2-carboxylate (1.8 g, 61%). $^1$H NMR (400 MHz, d$_6$-DMSO) δ: 7.90 (d, 1H), 7.81 (d, 1H), 7.55 (dd, 1H), 4.21 (q, 2H), 3.60 (s, 3H) and 1.14 (t, 3H).

Step 5: ethyl 4-cyano-3-(3,4-dichlorophenyl)-5-morpholin-4-ylthiophene-2-carboxylate A solution of ethyl 4-cyano-3-(3,4-dichlorophenyl)-5-(methylsulfonyl)thiophene-2-carboxylate (1.77 g, 4.38 mmol) and morpholine (1.91 mL, 21.9 mmol) in THF (40 mL) was stirred at rt under an atmosphere of argon for 3 days. A precipitate had formed and was filtered to give ethyl 4-cyano-3-(3,4-dichlorophenyl)-5-morpholin-4-ylthiophene-2-carboxylate (1.14 g, 63%). $^1$H NMR (400 MHz, d$_6$-DMSO) δ: 7.67-7.74 (m, 2H), 7.37 (dd, 1H), 4.06 (q, 2H), 3.74-3.78 (m, 4H), 3.59-3.63 (m, 4H) and 1.06 (t, 3H).

Step 6: 4-cyano-3-(3,4-dichlorophenyl)-5-morpholin-4-ylthiophene-2-carboxylic acid (75)

To a slurry of ethyl 4-cyano-3-(3,4-dichlorophenyl)-5-morpholin-4-ylthiophene-2-carboxylate (1.04 g, 2.53 mmol) in THF (20 mL) was added 1.0 M of sodium hydroxide in water (20 mL). The reaction mixture was stirred at 80° C. overnight and was concentrated. The residue was diluted with 1 N HCl and a precipitate formed. The precipitate was filtered and dried to give 4-cyano-3-(3,4-dichlorophenyl)-5-morpholin-4-ylthiophene-2-carboxylic acid (75) (0.88 g, 91%). LCMS: (FA) ES− 381.2. $^1$H NMR (400 MHz, d$_6$-DMSO) δ: 13.00 (s, 1H), 7.65-7.72 (m, 2H), 7.36 (d, 1H), 3.73-3.79 (m, 4H) and 3.55-3.61 (m, 4H).

Step 7: 4-cyano-3-(3,4-dichlorophenyl)-5-morpholin-4-ylthiophene-2-carboxamide (84)

To a suspension of 4-cyano-3-(3,4-dichlorophenyl)-5-morpholin-4-ylthiophene-2-carboxylic acid (0.198 g, 0.517 mmol) in DCM (5 mL) was added EDCI (0.198 g, 1.03 mmol) and HOBT (0.140 g, 1.03 mmol). The reaction mixture was stirred at rt for 30 min then ammonium hydroxide (1 mL, 20 mmol) was added. The reaction mixture was stirred for 4 h and was concentrated. The residue was diluted with water and extracted with EtOAc. The organic solutions were combined, washed with sat NaHCO$_3$, with brine, dried over MgSO$_4$, filtered and concentrated to give 4-cyano-3-(3,4-dichlorophenyl)-5-morpholin-4-ylthiophene-2-carboxamide (84) (0.195 g, 99%). LCMS: (FA) ES+ 382.2, ES− 380.1. $^1$H NMR (300 MHz, d$_6$-DMSO) δ: 7.73 (d, 1H), 7.64 (d, 1H), 7.36 (dd, 1H), 3.73-3.79 (m, 4H) and 3.49-3.54 (m, 4H).

Compounds in the following table were prepared from the appropriate starting materials in a method analogous to that of Example 7:

| 88 | LCMS: (FA) ES+ 368. |
|----|---------------------|
| 89 | LCMS: (FA) ES+ 382. |

Example 8

Synthesis of 4-cyano-3-(3,4-dichlorophenyl)-N-(1,3-dimethyl-1H-pyrazol-5-yl)-5-morpholin-4-ylthiophene-2-carboxamide (85)

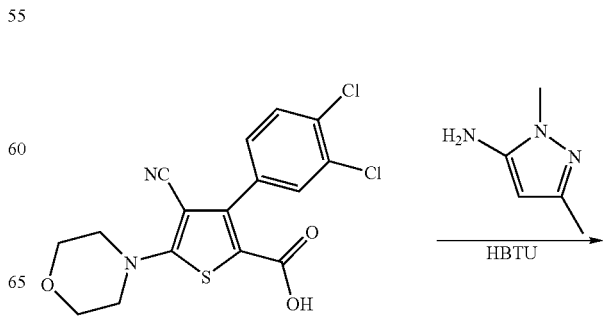

69
-continued

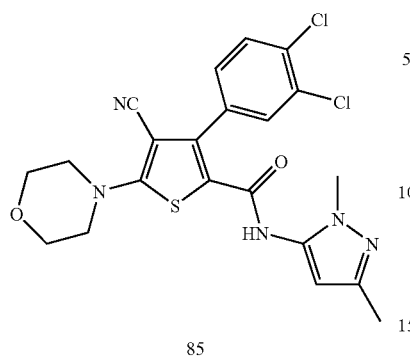

85

4-cyano-3-(3,4-dichlorophenyl)-5-morpholin-4-ylthiophene-2-carboxylic acid (0.030 g, 0.07 mmol), HBTU (0.080 g, 0.21 mmol), N-methyl morpholine (0.023 mL, 0.21 mmol) and DMF (1 mL) were added to a sealed reaction tube containing 1,3-dimethyl-1H-pyrazol-5-amine (0.023 g, 0.21 mmol). The reaction mixture was allowed to shake overnight and was concentrated. The residue was dissolved up in THF/chloroform (1:3) (4 mL) and washed with sat NaHCO$_3$ (2 mL). The organic solution was separated and concentrated. The crude product was dissolved in DMSO (1.5 mL) and was purified by reverse phase chromatography to give 4-cyano-3-(3,4-dichlorophenyl)-N-(1,3-dimethyl-1H-pyrazol-5-yl)-5-morpholin-4-ylthiophene-2-carboxamide (85) (0.003 g, 10%). LCMS: (FA) ES+ 476.4.

Compounds in the following table were prepared from the appropriate starting materials in a method analogous to that of Example 8:

| | |
|---|---|
| 70 | LCMS: (FA) ES+ 426.3. |
| 63 | LCMS: (FA) ES+ 454.4. |
| 31 | LCMS: (FA) ES+ 467.3. |
| 30 | LCMS: (FA) ES+ 440.3. |
| 56 | LCMS: (FA) ES+ 440.3. |
| 83 | LCMS: (FA) ES+ 440.3 |
| 19 | LCMS: (FA) ES+ 426.1. |
| 68 | LCMS: (FA) ES+ 470.4. |
| 3 | LCMS: (FA) ES+ 479.3. |
| 46 | LCMS: (FA) ES+ 458.3. |
| 76 | LCMS: (FA) ES+ 422.1. |
| 25 | LCMS: (FA) ES+ 494.3. |
| 32 | LCMS: (FA) ES+ 482.4. |
| 49 | LCMS: (FA) ES+ 428.2. |
| 14 | LCMS: (FA) ES+ 473.3. |
| 41 | LCMS: (FA) ES+ 467.3. |
| 67 | LCMS: (FA) ES+ 440.3. |
| 57 | LCMS: (FA) ES+ 440.2. |
| 53 | LCMS: (FA) ES+ 438.2. |
| 7 | LCMS: (FA) ES+ 504.4. |
| 15 | LCMS: (FA) ES+ 440.3. |
| 5 | LCMS: (FA) ES+ 473.3. |

70

Example 9

Synthesis of N-(4-bromobenzyl)-4-cyano-3-(2,4-dichlorophenyl)-5-morpholin-4-ylthiophene-2-carboxamide (45)

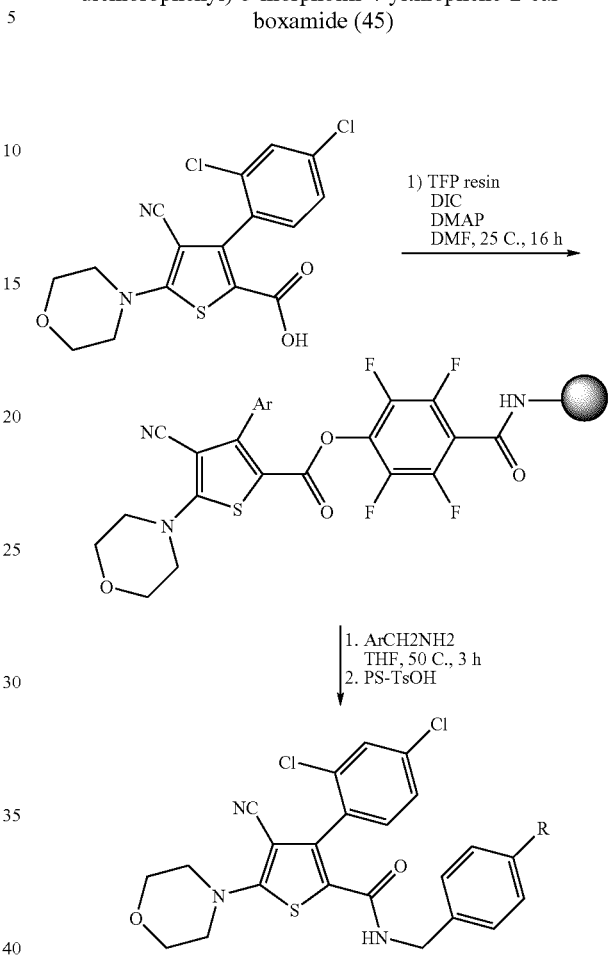

Tetrafluorophenol resin (TFP) of loading 130 mmol/g (100 mg, 130 umol) was allowed to swell in dry DMF (1.2 mL) and treated with 4-cyano-3-(2,4-dichlorophenyl)-5-morpholin-4-ylthiophene-2-carboxylic acid (0.125 g, 0.325 mmol), DIC (33 mg, 41 mg, 0.325 mmol) and DMAP (40 mg, 0.325 mmol). The suspension was agitated for 24 h at ambient temperature then filtered and washed with DMF (3×3 mL) and DCM (3×3 mL) and dried under vacuo. IR 2212, 1744 cm$^{-1}$.

The resin was divided into two equal aliquots which were swelled in anhydrous THF and treated with 1 equiv (0.06 mmol) of the appropriate benzylic amine and allowed to react at 60° C. for 3 h. After cooling, the THF solution was decanted from the resin and filtered over a 500 mg cartridge of polymer supported tosic acid that had been washed with methanol. The cartridge was then washed with DCM, MeOH and EtOAc and the filtrates evaporated to give pure product free from primary amine starting material; 45 (16 mg, 45%). LCMS: (FA) ES+ 550, 552.

Compound 22 was prepared from the appropriate starting materials in a method analogous to that of Example 9:

| | |
|---|---|
| 22 | LCMS: (FA) ES+ 540 |

Example 10

Synthesis of N-[4-cyano-3-(2,4-dichlorophenyl)-5-morpholin-4-yl-2-thienyl]-N-(2-hydroxyethyl)urea (86)

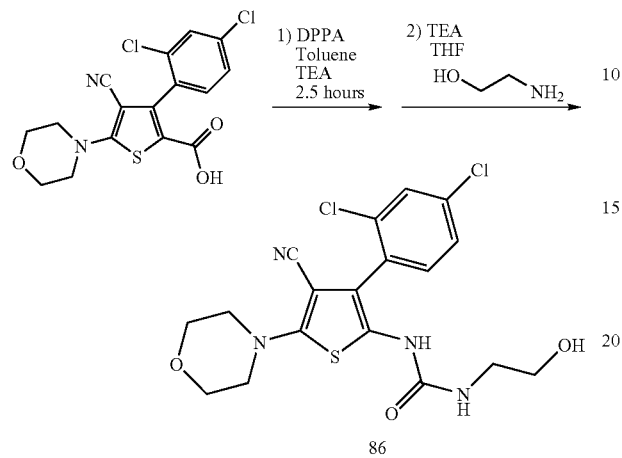

86

4-cyano-3-(2,4-dichlorophenyl)-5-morpholin-4-ylthiophene-2-carboxylic acid (0.030 g, 0.08 mmol) was weighed out into a microwave tube that was then sealed. Toluene (1 ml), TEA (0.014 mL, 0.100 mmol) and diphenylphosphoryl azide (0.020 mL, 0.091 mmol) were added to the tube. The reaction mixture was shaken at room temperature for 30 minutes, and then heated to 80° C. for 2 hours. 2-aminoethanol (0.0061 ml, 0.1 mmol) and anhydrous THF (1 mL) and TEA (0.014 mL, 0.100 mmol) were pre-mixed and then added to the reaction mixture. The reaction was heated at 80° C. for a further 60 minutes, then allowed to cool to RT and shaken overnight. The solvent was evaporated in a Genevac HT12 and the residue was purified on the Agilent 100 series LC/MSD (FA) to give N-[4-cyano-3-(2,4-dichlorophenyl)-5-morpholin-4-yl-2-thienyl]-N-(2-hydroxyethyl)urea (86). LCMS: (FA) ES+ 441.3.

Compounds in the following table were prepared from the appropriate starting materials in a method analogous to that of Example 10:

| | |
|---|---|
| 29 | LCMS: (FA) ES+ 495.4. |
| 43 | LCMS: (FA) ES+ 455.3. |

Example 11

Synthesis of 4-Cyano-3-(2,4-dichlorophenyl)-N-hydroxy-5-morpholin-4-yl-thiophene-2-carboxamide (24)

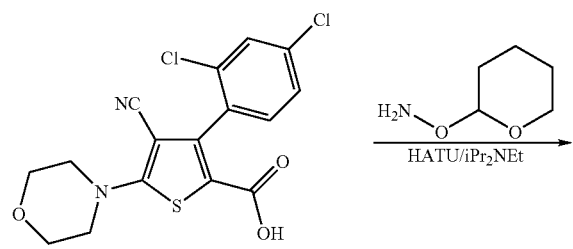

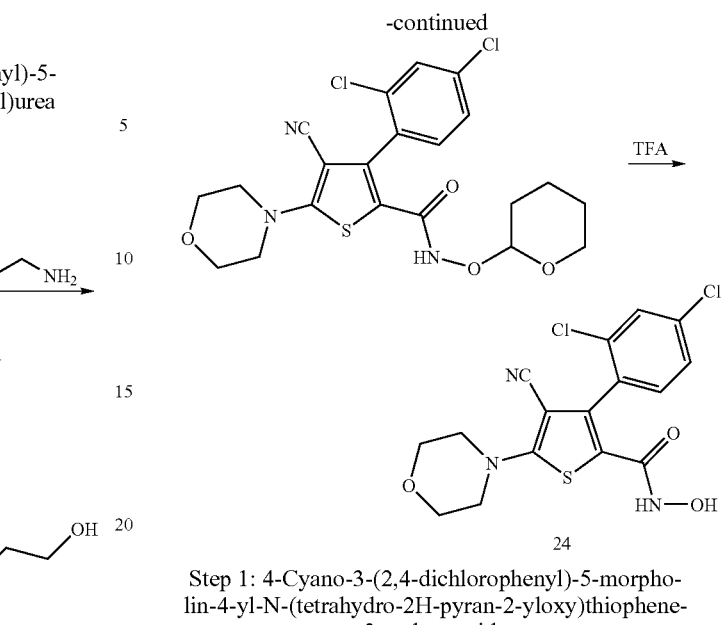

24

Step 1: 4-Cyano-3-(2,4-dichlorophenyl)-5-morpholin-4-yl-N-(tetrahydro-2H-pyran-2-yloxy)thiophene-2-carboxamide 4-Cyano-3-(2,4-dichlorophenyl)-5-morpholin-4-ylthiophene-2-carboxylic acid (0.080 g, 0.21 mmol), HATU (0.095 g, 0.25 mmol), and diisopropylethylamine (0.073 mL, 0.42 mmol) were dissolved in DMF (2 mL) and stirred for 30 minutes. O-Tetrahydropyran-2-yl)hydroxylamine (0.049 g, 0.42 mmol) was added and the mixture was stirred at room temperature. After 30 minutes, LCMS showed complete conversion. Reaction was quenched by addition of water (5 mL) and the precipitate was filtered off, washed with water (2 mL) and hexane (5 mL) and dried to afford the title compound (0.055 g, 55%).

LCMS: (FA) ES+ 482.

Step 2: 4-Cyano-3-(2,4-dichlorophenyl)-N-hydroxy-5-morpholin-4-yl-thiophene-2-carboxamide (24)

4-Cyano-3-(2,4-dichlorophenyl)-5-morpholin-4-yl-N-(tetrahydro-2H-pyran-2-yloxy)thiophene-2-carboxamide (0.050 g, 0.10 mmol) was dissolved in DCM (3 mL) and TFA (0.24 mL, 3.11 mmol) was added. The solution was stirred at room temperature overnight. Solvent was evaporated and the residue was purified by column chromatography (silica gel, elution with DCM to 10% MeOH in DCM over 20 minutes) to give the title compound 24 (0.030 g, 67%). LCMS: (FA) ES+ 398.

Example 12

Synthesis of 4-cyano-3-(2,4-dichlorophenyl)-5-[2-(hydroxymethyl)morpholine-4-yl]thiophene-2-carboxamide (87)

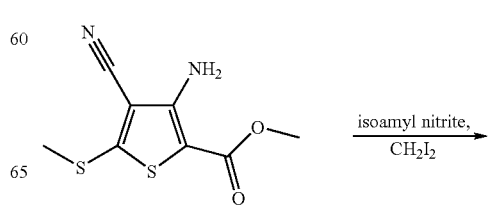

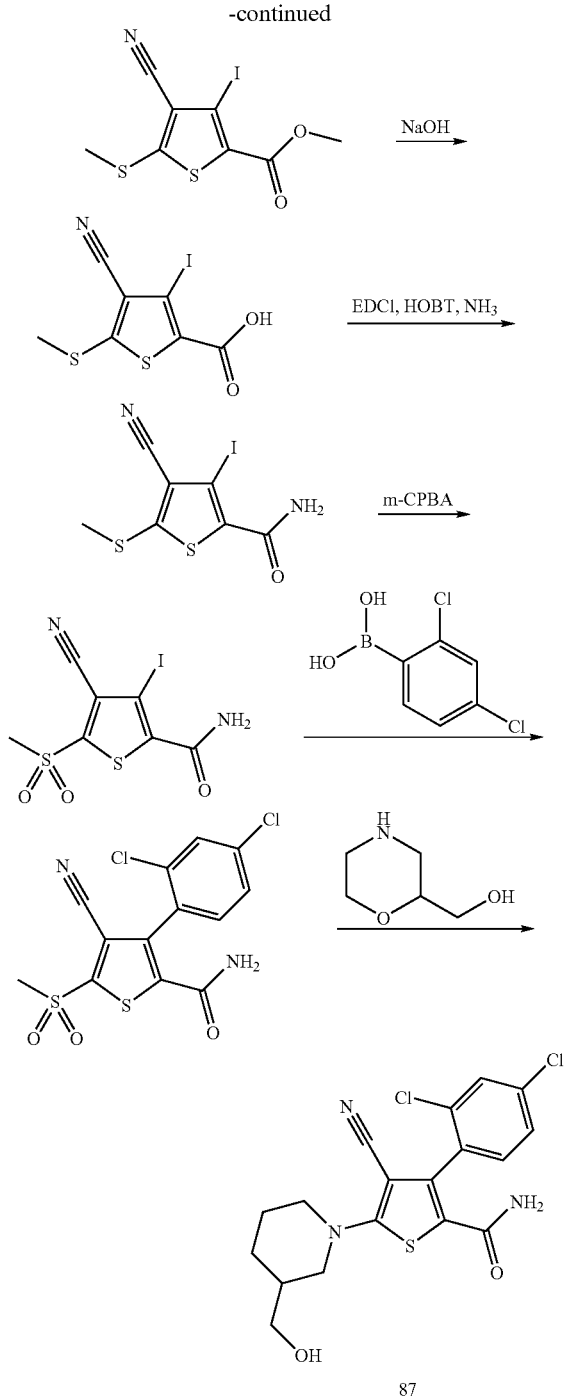

filtered and washed with a solution of 90% hexanes in acetonitrile (10 mL), 75% hexanes in diethyl ether (10 mL) and 100% hexanes (20 mL) to give methyl 4-cyano-3-iodo-5-(methylsulfanyl)thiophene-2-carboxylate (3.4 g, 57%) as a light orange solid. $^1$H NMR (400 MHz, CDCl$_3$) δ: 3.91 (s, 3H), 2.70 (s, 3H)

Step 2: 4-cyano-3-iodo-5-(methylsulfanyl)thiophene-2-carboxylic acid

To a solution of methyl 4-cyano-3-iodo-5-(methylsulfanyl) thiophene-2-carboxylate (3.40 g, 10 mmol) in tetrahydrofuran (80 mL) and water (16 mL) was added a solution of 1.00M sodium hydroxide in water (30 mL). The solution was allowed to stir overnight. The reaction was quenched with a solution of 1N hydrogen chloride in water (50 mL) and diluted with water (400 mL). The resultant precipitate was filtered, washed with water (2×100 mL) and dried in a vacuum oven to give 4-cyano-3-iodo-5-(methylsulfanyl) thiophene-2-carboxylic acid (2.6 g, 79%) as a white solid. LCMS: (FA) ES+ 326.

$^1$H NMR (400 MHz, d$_6$-DMSO) δ: 14.1-13.8 (bs, 1H), 2.75 (s, 3H).

Step 3: 4-cyano-3-iodo-5-(methylsulfanyl)thiophene-2-carboxamide

To a suspension of 4-cyano-3-iodo-5-(methylsulfanyl) thiophene-2-carboxylic acid (2.85 g, 7.93 mmol) in methylene chloride (30 mL), were added N-(3-dimethylaminopropyl)-N'-ethylcarbodiimide hydrochloride (3.28 g, 17.1 mmol) and 1-hydroxybenzotriazole (2.27 g, 16.8 mmol). The reaction mixture was stirred at room temperature for two hours and ammonium hydroxide (15.4 mL) was added and the biphasic mixture was stirred at room temperature for two hours. Water (100 mL), methanol (50 mL), methylene chloride (200 mL) was added. The organic layer was removed. The aqueous layer was extracted five times with a solution of 20% methanol in methylene chloride (100 mL). The combined organic extracts were dried over anhydrous magnesium sulfate, filtered and concentrated to the title compound as dark red oil (1.47 g, 57%). LCMS: (FA) ES+ 325.

Step 4: 4-cyano-3-iodo-5-(methylsulfonyl) thiophene-2-carboxamide

To a solution of 4-cyano-3-iodo-5-(methylsulfanyl) thiophene-2-carboxamide (1.46 g, 4.50 mmol) was dissolved in methylene chloride (60 mL), tetrahydrofuran (20 mL), N,N-dimethylformamide (20 mL), m-chloroperbenzoic acid (5.05 g, 22.5 mmol) was added and the mixture was stirred at room temperature overnight. The methylene chloride was removed in vacuo. The remaining residue was diluted with ethyl acetate (200 mL) and washed three times with a solution of 1.00M sodium hydroxide in water (50 mL). The organic phase was removed and the aqueous phase was extracted five times with ethyl acetate (100 mL). The combined organic extracts were washed twice with a solution of 1.00M sodium hydroxide in water (50 mL). The organic extracts were concentrated in vacuo. The residue was suspended in water (100 mL) and a precipitate formed. The precipitate was filtered, washed with water (40 mL), hexanes (100 mL), and dried in a vacuum oven to give the title compound as a white solid (1.00 g, 62%). LCMS: (FA) ES+ 357. $^1$H NMR (400 MHz, d$_6$-DMSO) δ: 8.16 (s, 2H), 3.56 (s, 3H).

Step 1: Methyl 4-cyano-3-iodo-5-(methylsulfanyl) thiophene-2-carboxylate

To a suspension of methyl 3-amino-4-cyano-5-(methylthio)thiophene-2-carboxylate (4.0 g, 17.5 mmol) in acetonitrile (20 mL) was added diiodomethane (4.94 mL, 61.3 mmol). The reaction mixture was heated at 38° C. Isoamyl nitrate (5.13 g, 43.8 mmol) was added dropwise over five minutes. After the addition of amyl nitrate, the reaction mixture was allowed to cool to room temperature and stirred for two hours. The reaction mixture was cooled in an ice bath and hexanes (20 mL) were added. The resultant precipitate was

Step 5: 4-cyano-3-(2,4-dichlorophenyl)-5-(methylsulfonyl)thiophene-2-carboxamide 4-cyano-3-iodo-5-(methylsulfonyl)thiophene-2-carboxamide (0.500 g, 1.40 mmol), bis(dibenzylideneacetone)palladium (0.040 g, 0.0700 mmol), bis(2-diphenylphosphinophenyl)ether (0.057 g, 0.100 mmol), and potassium phosphate (0.596 g, 2.81 mmol) were suspended in 1,2-dimethoxyethane (10.0 mL) and N,N-dimethylacetamide (5 mL). The suspension was flushed with argon and the reaction mixture was irradiated in microwave at 150° C. (300 watts) for three hours. The reaction mixture was concentrated in vacuo and column chromatography was performed to yield the title compound (0.080 g, 14%) as beige foam. $^1$H NMR (400 MHz, d$_4$-methanol) δ: 7.71-7.69 (m, 1H), 7.52-7.50 (m, 2H), 3.46 (s, 3H).

Step 6: 4-cyano-3-(2,4-dichlorophenyl)-5-[2-(hydroxymethyl)morpholin-4-yl]thiophene-2-carboxamide (87)

4-cyano-3-(2,4-dichlorophenyl)-5-(methylsulfonyl)thiophene-2-carboxamide (0.013 g, 0.0346 mmol) was dissolved in 2-hydroxymethylmorpholine (0.300 g, 2.56 mmol) and the solution was heated at 60° C. overnight. The residue was concentrated in vacuo and column chromatography was performed and yielded the title compound 87 (0.010 g, 66%) as a white solid. LCMS: (FA) ES+ 412, 414, 416. $^1$H NMR (400 MHz, d$_4$-methanol) δ: 7.68 (s, 1H), 7.50 (d, 1H), 7.40 (d, 1H), 4.08-3.92 (m, 3H), 3.88-3.56 (m, 4H), 3.16-3.04 (m, 2H).

Compound 71 was prepared from the appropriate starting materials in a method analogous to that of Example 12:

| 71 | LCMS: (FA) ES+ 396 |
|---|---|

II. Biological Data

Example 1

PI3K Enzyme Assay

Expression and Purification of PI3K Enzyme

Active phosphatidylinositol 3' kinase (PI3K) enzyme was purified at Millennium Pharmaceuticals from SF9 insect cells (Invitrogen) co-infected with baculovirus containing amino-terminal His-tagged p110α and p85α expression constructs.

PI3K Enzyme Homogenous Time Resolved Fluorescence (HTRF®) Assay

The PI3K enzyme HTRF® assay makes use of an energy transfer complex comprised of biotin-PI(3,4,5)P$_3$, Europhium labeled anti-GST monoclonal antibody, a GST-tagged GRP1 pleckstrin homology (PH) domain, and Streptavidin-APC (allophycocyanin). Excitation of the Europium in the complex results in a stable time-resolved fluorescence resonance energy transfer (FRET) signal. Phosphatidylinositol 3,4,5 triphosphate (PI(3,4,5)P$_3$, the product of PI3K, disrupts the energy transfer complex by competing with biotin-PI(3,4,5)P$_3$ for binding to the GRP1 PH domain, resulting in a decreased fluorescent signal. Inhibitors of PI3K in the reaction prevent a decrease in the fluorescent signal.

PI3K enzyme (325 μM) was incubated with di-C8 PI(4,5)P$_2$ substrate (3.5 μM, CellSignals, Inc.) in assay buffer (50 mM HEPES pH 7.0, 5 mM DTT, 150 mM NaCl, 10 mM β-glycerophosphate, 5 mM MgCl$_2$, 0.25 mM sodium cholate, 0.001% CHAPS) containing 25 μM ATP and 0.5 μL of test compound (in 100% DMSO) at multiple concentrations in a final volume of 20.5 μL in 384 well plates for 30 min at 22-23° C. The reaction was terminated by adding 5 μL of detection buffer (50 mM HEPES pH 7.0, 5 mM DTT, 1 mM NaCl, 10% Tween-20) containing EDTA (90 mM) and biotin-PI(3,4,5)P$_3$ (150 nM, Echelon Bioscience) to each well. 5 μL of detection buffer containing GST-fused GRP1 PH domain protein (210 nM, Millennium Pharmaceuticals), anti-GST-Europium tagged cryptate antibody (2.25 nM, CisBio), Streptavidin-XL (90 nM, CisBio) and potassium fluoride (240 mM) were then added to each well and incubated for 1 hour. Fluorescent signal for each well was then measured on an LJL_Analyst (Molecular Devices). Concentration response curves were generated by calculating the fluorescent signal in test compound-treated samples relative to DMSO-treated (0% inhibition) and EDTA-treated (100% inhibition) controls, and concentrations producing 50% inhibition (IC$_{50}$ values) were determined from those curves.

Example 2

PI3K Cell Assays

Forkhead Redistribution Assay

Inhibition of PI3K in cells can be assessed using the Forkhead Redistribution Assay (BioImage). FoxolA fused to EGFP (FoxolA-EGFP) expressed in U2OS osteosarcoma cells localizes to the cytoplasm when the PI3K pathway is actively signaling. Inactivation of pathway signaling leads to a translocation of the protein from the cytoplasm to the nucleus. Therefore, pathway inhibition can be measured by quantifying the fluorescent intensity of FoxolA-EGFP within the nucleus.

U2OS cells constitutively expressing FoxolA-EGFP (6500 cells/well) were plated onto the inner 60 wells of 96 well dishes (BD Falcon OPTILUX black clear bottom) in 100 μL of cell culture media (DMEM (Invitrogen) containing 10% Fetal Bovine Serum (HyClone) and 1% Penicillin-Streptavidin (Invitrogen) and grown overnight in a humidified chamber at 37° C. The cell culture media was removed and the cells were rinsed with 100 μL of low serum media (DMEM containing 0.933% Fetal Bovine Serum and 1% Penicillin-Streptavadin) and incubated in 75 μL of low serum media for 1 hour in a humidified chamber at 37° C. Test compounds (25 μL) at multiple concentrations suspended in DMEM containing 1% Penicillin-Streptavadin were added to cells and incubated in a humidified chamber at 37° C. for 1 hour. The media was removed and the cells were fixed in 100 μL of 4% paraformaldehyde in phosphate buffered saline (PBS) for 10 min and then washed with 100 μL of PBS. DRAQ5 mix (100 μL, Alexis Biochemicals) diluted 1:5000 in PBS containing RNAase (1:10,000, Sigma) was added to cells for 30 minutes. The plates were then imaged (16 fields per well) using an Opera Imager (Evotec) and FoxolA-EGFP fluorescent intensity within the nucleus (DRAQ5-positive) was quantified using Acapella Software (Evotec). Concentration response curves were generated by calculating the nuclear fluorescent intensity of Foxo-IA EGFP in test compound-treated samples and concentrations producing 50% inhibition (IC$_{50}$ values) relative to the positive control were determined from those curves.

Example 3

Anti-Proliferation Assay

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of PI3K inhibitors.

Test compounds (4 μL in 100% DMSO) were diluted in 75 μL of Hanks Buffered Saline Solution (Invitrogen). The diluted test compounds (8 μL) were then added to 384-well TC-treated Black/Clear plates (Falcon). HCT-116 cells (American Type Culture Collection) maintained in McCoy's 5a modified media (Invitrogen) containing 10% Fetal Bovine Serum and 1% Penicillin-Streptavadin were added at 1000 cells per well. H460 cells (American Type Culture Collection) maintained in RPMI 1640 containing 10% Fetal Bovine Serum and 1% Penicillin-Streptavadin were added at 1500 cells per well. The cells were then incubated with compound in a humidified chamber at 37° C. for 72 hours. The plates were then removed from the cell culture chambers and allowed to equilibrate to room temperature for 30 min. All but 25 μL of cell culture media was removed from each well, and 25 μl of ATPlite reagent (Perkin Elmer) was added to each well. Luminescence was measured within 5 minutes of adding the ATPlite reagent on a LEADSeeker Luminescence Counter (GE Healthcare Life Sciences). Concentration response curves were generated by calculating the luminescence decrease in test compound-treated samples relative to DMSO-treated controls, and growth inhibition ($IC_{50}$) values were determined from those curves.

As detailed above, compounds of the invention inhibit PI3K. In certain embodiments, compounds of the invention have an IC50<5.0 μM. In other embodiments, compounds of the invention have an IC50<1.0 μM. In still other embodiments, compounds of the invention have an IC50<0.1 μM.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:
1. A compound of formula I:

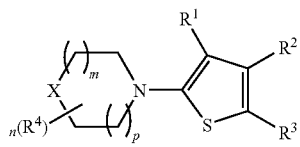

or a pharmaceutically acceptable salt thereof, wherein:
$R^1$ is H, —CN, —COOR$^{1a}$, or —CON(R$^{1a}$)$_2$,
  wherein each occurrence of $R^{1a}$ is independently hydrogen or optionally substituted $C_{1-4}$aliphatic;
$R^2$ is —Z—$R^6$, or —$R^6$, wherein:
  Z is selected from an optionally substituted $C_{1-3}$ alkylene chain, —O—, —S—, —S(O)—, —S(O)$_2$—, —C(O)—, —CO$_2$—, —C(O)NR$^{2a}$—, —N(R$^{2a}$)C(O)—, —N(R$^{2a}$)CO$_2$—, —S(O)$_2$NR$^{2a}$—, —N(R$^{2a}$)S(O)$_2$—, —OC(O)N(R$^{2a}$)—, —N(R$^{2a}$)C(O)NR$^{2a}$—, —N(R$^{2a}$)S(O)$_2$N(R$^{2a}$)—, or —OC(O)—,
  $R^{2a}$ is hydrogen or an optionally substituted $C_{1-4}$ aliphatic, and
  $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur,
$R^3$ is —V$_1$—R$^{3c}$, -T$_1$-R$^{3b}$, or —V$_1$-T$_1$-R$^{3b}$ wherein:
  V$_1$ is —C(O)—, —NR$^{3a}$—, —CO$_2$—, —C(O)NR$^{3a}$—, C(O)NR$^{3a}$O—, —NR$^{3a}$C(O)NR$^{3a}$—, —NR$^{3a}$S(O)$_2$—, or —NR$^{3a}$S(O)$_2$NR$^{3a}$—;
  each occurrence of $R^{3a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  T$_1$ is an optionally substituted $C_1$-$C_6$ alkylene chain wherein the alkylene chain optionally is interrupted by —N(R$^{3a}$)—, —O—, —S—, —S(O)—, —S(O)$_2$—, —C(O)—, —C(O)O—, —C(O)N (R$^{3a}$)—, —S(O)$_2$N(R$^{3a}$)—, —OC(O)N(R$^{3a}$)—, —N(R$^{3a}$)C(O)—, —N(R$^{3a}$)SO$_2$—, —N(R$^{3a}$)C(O) O—, —NR$^{3a}$ C(O)N(R$^{3a}$)—, —N(R$^{3a}$)S(O)$_2$N (R$^{3a}$)—, —OC(O)—, or —C(O)N(R$^{3a}$)—O— or wherein T$_1$ forms part of an optionally substituted 3-7 membered cycloaliphatic or heterocyclyl ring;
  each occurrence of $R^{3c}$ is independently hydrogen, halogen, —CN, —NO$_2$, —N(R$^{3a}$)$_2$, —OR$^{3a}$, —SR$^{3a}$, —S(O)$_2$R$^{3a}$, —C(O)R$^{3a}$, —C(O)OR$^{3a}$, —C(O)N (R$^{3a}$)$_2$, —S(O)$_2$N(R$^{3a}$)$_2$, —OC(O)N(R$^{3a}$)$_2$, —N(R$^{3a}$)C(O)R$^{3a}$, —N(R$^{3a}$)SO$_2$R$^{3a}$, —N(R$^{3a}$)C(O) OR$^{3a}$, —N(R$^{3a}$)C(O)N(R$^{3a}$)$_2$, or —N(R$^{3a}$)SO$_2$N (R$^{3a}$)$_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{3c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or
  $R^{3a}$ and $R^{3c}$ taken together with a nitrogen atom to which they are bound form an optionally substituted 4-7-membered heterocyclyl ring having 0-1 additional heteroatoms independently selected from nitrogen, oxygen, or sulfur;
each occurrence of $R^4$ is independently —R$^{4a}$, -T$_2$-R$^{4d}$, or —V$_2$-T$_2$-R$^{4d}$, wherein:
  each occurrence of $R^{4a}$, as valency and stability permit, is independently fluorine, =O, =S, —CN, —NO$_2$, —R$^{4c}$, —N(R$^{4b}$)$_2$, —OR$^{4b}$, —SR$^{4c}$, —S(O)$_2$R$^{4c}$, —C(O)R$^{4b}$, —C(O)OR$^{4b}$, —C(O)N(R$^{4b}$)$_2$, —S(O)$_2$ N(R$^{4b}$)$_2$, —OC(O)N(R$^{4b}$)$_2$, —N(R$^{4e}$)C(O)R$^{4b}$, —N(R$^{4e}$)SO$_2$R$^{4c}$, —N(R$^{4e}$)C(O)OR$^{4b}$, —N(R$^{4e}$)C (O)N(R$^{4b}$)$_2$, or —N(R$^{4e}$)SO$_2$N(R$^{4b}$)$_2$, or two occurrences of $R^{4b}$, taken together with a nitrogen atom to which they are bound, form an optionally substituted 4-7-membered heterocyclyl ring having 0-1 additional heteroatoms selected from nitrogen, oxygen, or sulfur;
  each occurrence of $R^{4b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4e}$ is independently hydrogen or an optionally substituted $C_{1-6}$ aliphatic group;

each occurrence of $V_2$ is independently —N($R^{4e}$)—, —O—, —S—, —S(O)—, —S(O)$_2$—, —C(O)—, —C(O)O—, —C(O)N($R^{4e}$)—, —S(O)$_2$N($R^{4e}$)—, —OC(O)N($R^{4e}$)—, —N($R^{4e}$)C(O)—, —N($R^{4e}$)SO$_2$—, —N($R^{4e}$)C(O)O—, —NR$^{4e}$C(O)N($R^{4e}$)—, —N($R^{4e}$)SO$_2$N($R^{4e}$)—, —OC(O)—, or —C(O)N($R^{4e}$)—O—; and $T_2$ is an optionally substituted $C_1$-$C_6$ alkylene chain wherein the alkylene chain optionally is interrupted by —N($R^{4a}$)—, —O—, —S—, —S(O)—, —S(O)$_2$—, —C(O)—, —C(O)O—, —C(O)N($R^{4a}$)—, —S(O)$_2$N($R^{4a}$)—, —OC(O)N($R^{4a}$)—, —N($R^{4a}$)C(O)—, —N($R^{4a}$)SO$_2$—, —N($R^{4a}$)C(O)O—, —NR$^{4a}$C(O)N($R^{4a}$)—, —N($R^{4a}$)S(O)$_2$N($R^{4a}$)—, —OC(O)—, or —C(O)N($R^{4a}$)—O— or wherein $T_2$ or a portion thereof optionally forms part of an optionally substituted 3-7 membered cycloaliphatic or heterocyclyl ring;

n is 0-6;
m is 0, 1, or 2;
p is 0, 1, or 2; and
X is O, S, C(O), S(O), S(O)$_2$, —CHF, —CF$_2$, or —CHOH,
provided that:
(a) when $R^1$ is H, then $R^2$ is an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen or sulfur; and
(b) a compound of formula I is other than:
(i) 2-thiophenecarboxylic acid, 3-(4-chlorophenyl)-4-cyano-5-(4-morpholinyl)-;
(ii) 2-thiophenecarboxylic acid, 3-(4-chlorophenyl)-4-cyano-5-(4-morpholinyl)-, methyl ester;
(iii) 3-thiophenecarbonitrile, 5-benzoyl-4-(methylamino)-2-(4-morpholinyl)-;
(iv) Acetamide, N-[2-benzoyl-4-cyano-5-(4-morpholinyl)-3-thienyl]-2-iodo-;
(v) Acetamide, N-[2-benzoyl-4-cyano-5-(4-morpholinyl)-3-thienyl]-2-chloro-;
(vi) Acetamide, N-[2-benzoyl-4-cyano-5-(4-morpholinyl)-3-thienyl]-2-chloro-N-methyl-; or
(vii) 2-Propenoid acid, 3-[3-(4-chlorophenyl)-5-(4-morpholinyl)-2-thienyl]-, methyl ester.

2. The compound of claim 1, wherein one or more substituents are selected from:
(a) X is O;
(b) $R^1$ is CN;
(c) $R^2$ is an optionally substituted 6-10-membered aryl, or 5-10-membered heteroaryl having 1-5 heteroatoms independently selected from nitrogen, oxygen, or sulfur;
(d) $R^3$ is selected from $V_1$—$R^{3c}$ or —$V_1$-$T_1$-$R^{3b}$;
(e) n is 0-2; or
(f) $R^4$ is —$R^{4a}$.

3. The compound of claim 2, wherein $R^3$ is selected from —CON($R^{3a}$)($R^{3c}$), —NR$^{3a}$C(O)N($R^{3a}$)($R^{3c}$), —COOR$^{3c}$; —CON($R^{3a}$)-T$^1$-R$^{3b}$, —NR$^{3a}$C(O)N($R^{3a}$)($R^{3c}$)-T$^1$-R$^{3b}$, or —COOR$^{3c}$-T$^1$-R$^{3b}$, where T$^1$ is optionally substituted $C_1$-$C_4$ alkylene optionally interrupted by one occurrence of —O—, —NHC(O)—, —C(O)NH—, or —NH—.

4. The compound of claim 1, wherein $R^2$ is optionally substituted with 1-4 independent occurrences of $R^7$, wherein $R^7$ is —$R^{7a}$, -T$_3$-R$^{7d}$, or —V$_3$-T$_3$-R$^{7d}$, and:

each occurrence of $R^{7a}$ is independently halogen, —CN, —NO$_2$, —R$^{7c}$, —N(R$^{7b}$)$_2$, —OR$^{7b}$, —SR$^{7c}$, —S(O)$_2$R$^{7c}$, —C(O)R$^{7b}$, —C(O)OR$^{7b}$, —C(O)N(R$^{7b}$)$_2$, —S(O)$_2$ N(R$^{7b}$)$_2$, —OC(O)N(R$^{7b}$)$_2$, —N(R$^{7e}$)C(O)R$^{7b}$, —N(R$^{7e}$)SO$_2$R$^{7c}$, —N(R$^{7e}$)C(O)OR$^{7b}$, —N(R$^{7e}$)C(O)N(R$^{7b}$)$_2$, or —N(R$^{7e}$)SO$_2$N(R$^{7b}$)$_2$, or two occurrences of R$^{7b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{7b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{7c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{7d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{7e}$ is independently hydrogen or an optionally substituted $C_{1-6}$ aliphatic group;

each occurrence of $V_3$ is independently —N(R$^{7e}$)—, —O—, —S—, —S(O)—, —S(O)$_2$—, —C(O)—, —C(O)O—, —C(O)N(R$^{7e}$)—, —S(O)$_2$N(R$^{7e}$)—, —OC(O)N(R$^{7e}$)—, —N(R$^{7e}$)C(O)—, —N(R$^{7e}$)SO$_2$—, —N(R$^{7e}$)C(O)O—, —NR$^{7e}$C(O)N(R$^{7e}$)—, —N(R$^{7e}$)SO$_2$N(R$^{7e}$)—, —OC(O)—, or —C(O)N(R$^{7e}$)—O—; and $T_3$ is an optionally substituted $C_1$-$C_6$ alkylene chain wherein the alkylene chain optionally is interrupted by —N(R$^{7a}$)—, —O—, —S—, —S(O)—, —S(O)$_2$—, —C(O)—, —C(O)O—, —C(O)N(R$^{7a}$)—, —S(O)$_2$N(R$^{7a}$)—, —OC(O)N(R$^{7a}$)—, —N(R$^{7a}$)C(O)—, —N(R$^{7a}$)SO$_2$—, —N(R$^{7a}$)C(O)O—, —NR$^{7a}$ C(O)N(R$^{7a}$)—, —N(R$^{7a}$)S(O)$_2$N(R$^{7a}$)—, —OC(O)—, or —C(O)N(R$^{7a}$)—O— or wherein T$_3$ or a portion thereof optionally forms part of an optionally substituted 3-7 membered cycloaliphatic or heterocyclyl ring.

5. The compound of claim 1, wherein X is O and R$^2$ is CN and the compound is represented by formula I-A:

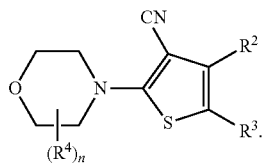

I-A

6. The compound of claim 5, wherein:
R$^2$ is an optionally substituted 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
R$^3$ is selected from V$_1$—R$^{3c}$ or —V$^1$-T$^1$-R$^{3b}$;
n is 0-2; and
R$^4$ is —R$^{4a}$.

7. The compound of claim 6, wherein:
R$^2$ is an optionally substituted 6-10-membered aryl, or a 5-10-membered heteroaryl ring having 1-5 heteroatoms independently selected from nitrogen, oxygen, or sulfur; wherein R$^2$ is optionally substituted with 1-4 independent occurrences of R$^7$, wherein R$^7$ is —R$^{7a}$, -T$_3$-R$^{7d}$, or —V$_3$-T$_3$-R$^{7d}$, and:
each occurrence of R$^{7a}$ is independently halogen, —CN, —NO$_2$, —R$^{7c}$, —N(R$^{7b}$)$_2$, —OR$^{7b}$, —SR$^{7c}$, —S(O)$_2$R$^{7c}$, —C(O)R$^{7b}$, —C(O)OR$^{7b}$, —C(O)N(R$^{7b}$)$_2$, —S(O)$_2$N(R$^{7b}$)$_2$, —OC(O)N(R$^{7b}$)$_2$, —N(R$^{7e}$)C(O)R$^{7b}$, —N(R$^{7e}$)SO$_2$R$^{7c}$, —N(R$^{7e}$)C(O)OR$^{7b}$, —N(R$^{7e}$)C(O)N(R$^{7b}$)$_2$, or —N(R$^{7e}$)SO$_2$N(R$^{7b}$)$_2$;
each occurrence of R$^{7b}$ is independently hydrogen or an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or two occurrences of R$^{7b}$, taken together with a nitrogen atom to which they are bound, form an optionally substituted 4-7-membered heterocyclyl ring having 0-1 additional heteroatoms selected from nitrogen, oxygen, or sulfur;
each occurrence of R$^{7c}$ is independently an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^{7d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10- membered heteroaryl having 1-5 heteroatoms independently selected from nitrogen, oxygen, or sulfur;
each occurrence of R$^{7e}$ is independently hydrogen or an optionally substituted C$_{1-6}$ aliphatic group;
each occurrence of V$_3$ is independently —N(R$^{7e}$)—, —O—, —S—, —S(O)—, —S(O)$_2$—, —C(O)—, —C(O)O—, —C(O)N(R$^{7e}$)—, —S(O)$_2$N(R$^{7e}$)—, —OC(O)N(R$^{7e}$)—, —N(R$^{7e}$)C(O)—, —N(R$^{7e}$)SO$_2$—, —N(R$^{7e}$)C(O)O—, —NR$^{7e}$C(O)N(R$^{7e}$)—, —N(R$^{7e}$)SO$_2$N(R$^{7e}$)—, —OC(O)—, or —C(O)N(R$^{7e}$)—O—; and
T$_3$ is an optionally substituted C$_1$-C$_6$ alkylene chain wherein the alkylene chain optionally is interrupted by —N(R$^{7a}$)—, —O—, —S—, —S(O)—, —S(O)$_2$—, —C(O)—, —C(O)O—, —C(O)N(R$^{7a}$)—, —S(O)$_2$N(R$^{7a}$)—, —OC(O)N(R$^{7a}$)—, —N(R$^{7a}$)C(O)—, —N(R$^{7a}$)SO$_2$—, —N(R$^{7a}$)C(O)O—, —NR$^{7a}$ C(O)N(R$^{7a}$)—, —N(R$^{7a}$)S(O)$_2$N(R$^{7a}$)—, —OC(O)—, or —C(O)N(R$^{7a}$)—O— or wherein T$_3$ or a portion thereof optionally forms part of an optionally substituted 3-7 membered cycloaliphatic or heterocyclyl ring;
R$^3$ is selected from —CON(R$^{3a}$)(R$^{3c}$), —NR$^{3a}$C(O)N(R$^{3a}$)(R$^{3c}$), —COOR$^{3c}$, —CON(R$^{3a}$)-T$^1$-R$^{3b}$, —NR$^{3a}$C(O)N(R$^{3a}$)(R$^{3c}$)-T$^1$-R$^{3b}$, or —COOR$^{3c}$-T$^1$-R$^{3b}$, wherein T$^1$ is optionally substituted C$_1$-C$_4$ alkylene optionally interrupted by one occurrence of —O—, —NHC(O)—, —C(O)NH—, or —NH—, R$^{3a}$ is hydrogen or an optionally substituted C$_{1-6}$ aliphatic group, R$^{3b}$ is hydrogen, halogen, OR$^{3a}$, or an optionally substituted group selected from 6-10-membered aryl, or 5-10-membered heteroaryl having 1-5 heteroatoms independently selected from nitrogen, oxygen, or sulfur, and R$^{3c}$ is hydrogen, C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and
n is 0-2.

8. The compound of claim 7, wherein:
R$^2$ is a phenyl group substituted with 1-3 independent occurrences of halogen, —CN, —NO$_2$, —R$^{7c}$, —N(R$^{7b}$)$_2$, —OR$^{7b}$, —SR$^{7c}$, —S(O)$_2$R$^{7c}$, —C(O)R$^{7b}$, —C(O)OR$^{7b}$, —C(O)N(R$^{7b}$)$_2$, —S(O)$_2$N(R$^{7b}$)$_2$, —OC(O)N(R$^{7b}$)$_2$, —N(R$^{7e}$)C(O)R$^{7b}$, —N(R$^{7e}$)SO$_2$R$^{7c}$, —N(R$^{7e}$)C(O)OR$^{7b}$, —N(R$^{7e}$)C(O)N(R$^{7b}$)$_2$, or —N(R$^{7e}$)SO$_2$N(R$^{7b}$)$_2$;
R$^3$ is selected from —CON(R$^{3a}$)(R$^{3c}$), —NR$^{3a}$C(O)N(R$^{3a}$)(R$^{3c}$), or —COOR$^{3c}$, wherein R$^{3a}$ is hydrogen or an optionally substituted C$_{1-6}$ aliphatic group and R$^{3c}$ is hydrogen or an optionally substituted C$_{1-6}$ aliphatic group; and,
n is 0.

9. The compound of claim 8, wherein:
R$^2$ is a phenyl group substituted with 1-3 independent occurrences of halo, C$_{1-3}$ alkyl, CN, C$_{1-3}$ haloalkyl, —OC$_{1-3}$ alkyl, —OC$_{1-3}$ halo alkyl, —NHC(O)C$_{1-3}$ alkyl, —NHC(O)NHC$_{1-3}$ alkyl, NHS(O)$_2$C$_{1-3}$ alkyl, or —COH.

10. The compound of claim 1, wherein the compound is selected from:

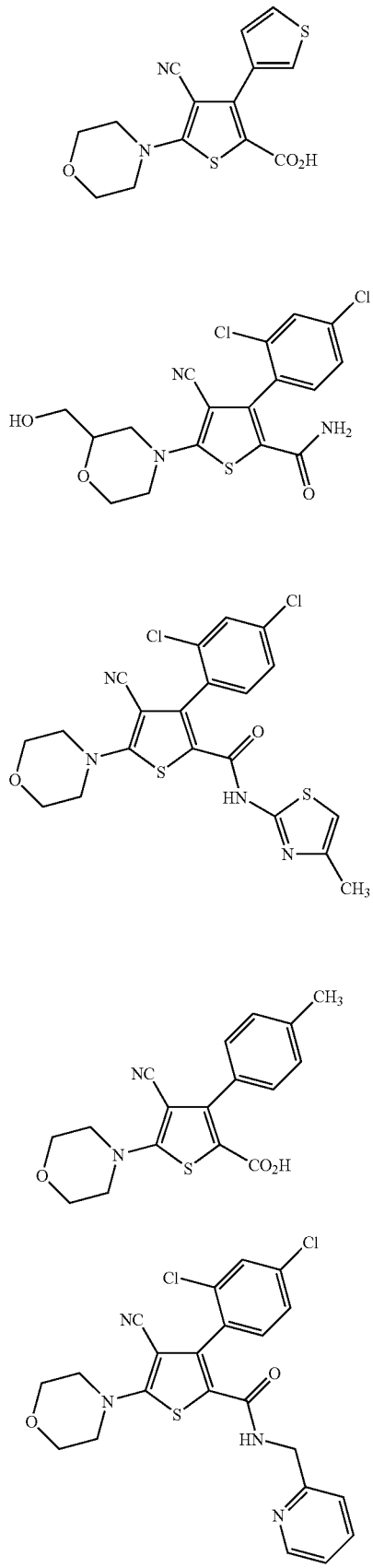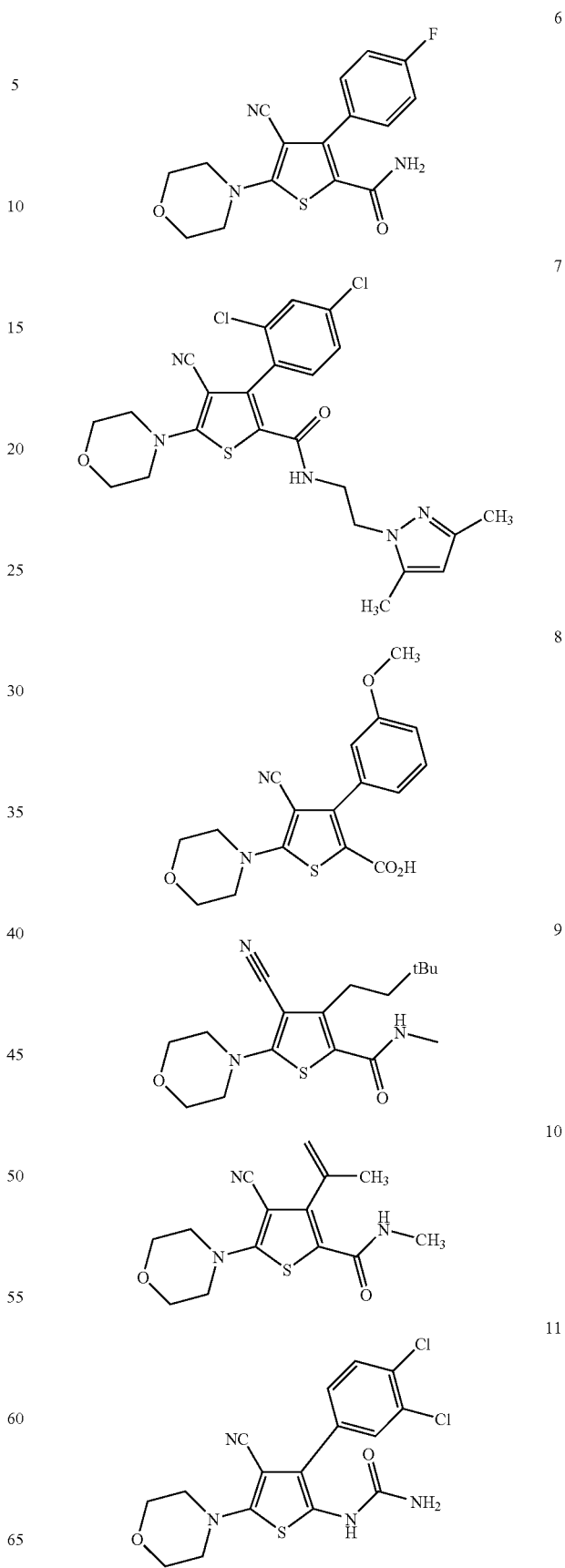

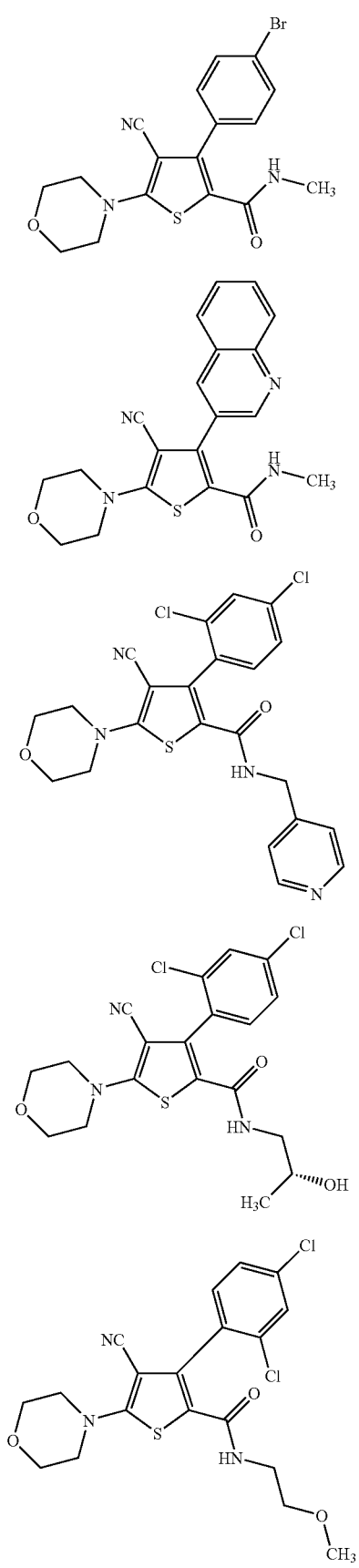
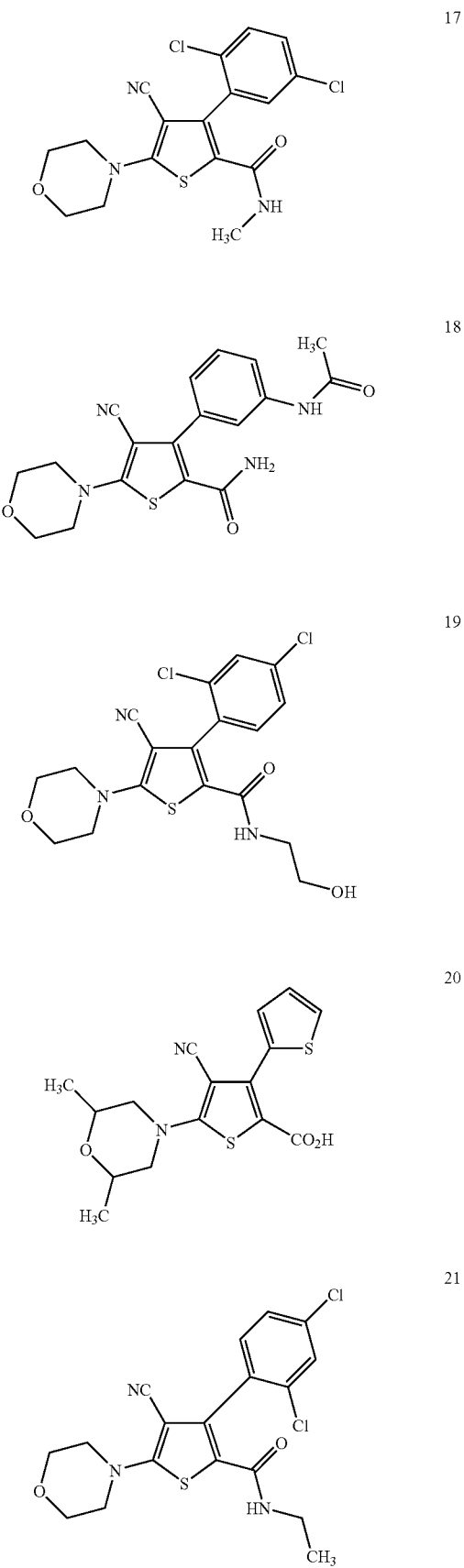

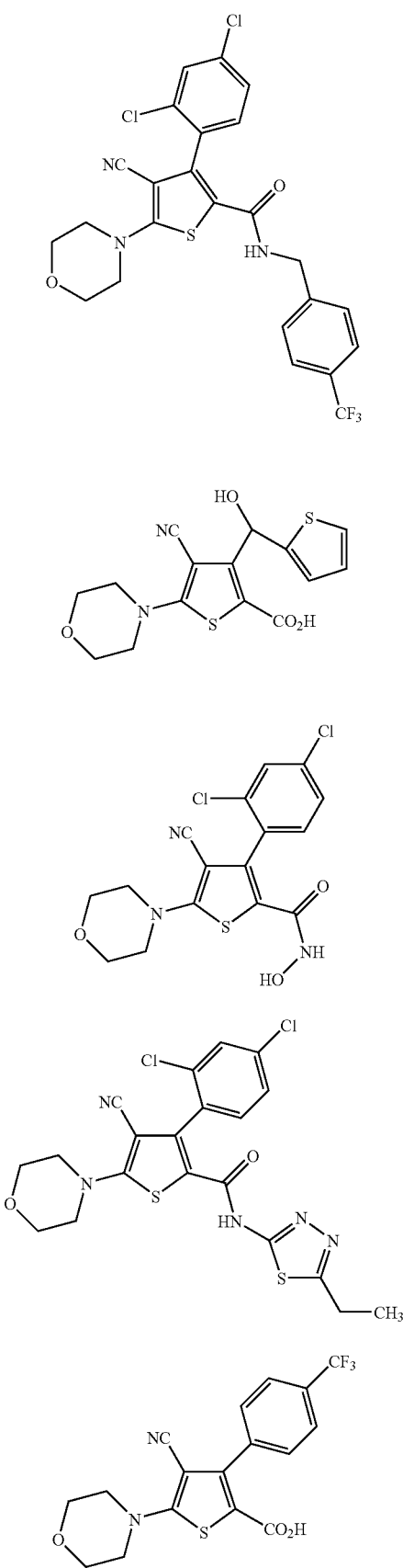
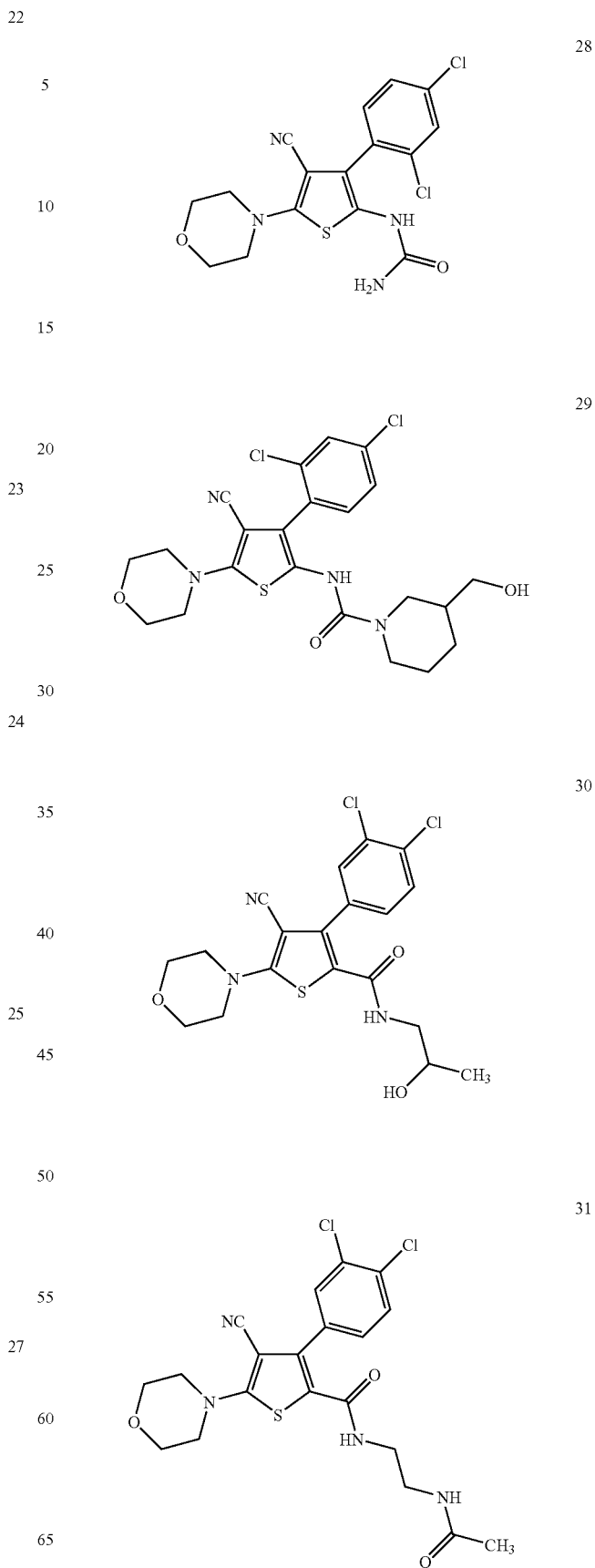

-continued
32
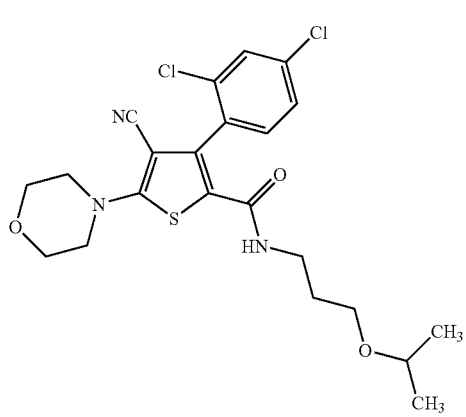
33
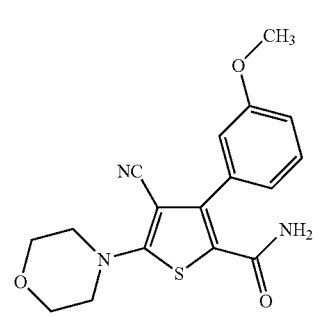
34
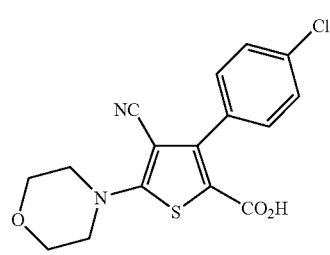
35
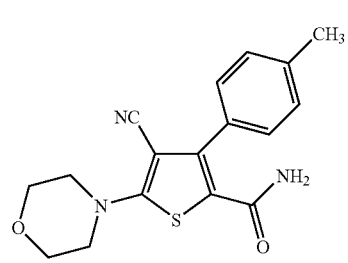
36
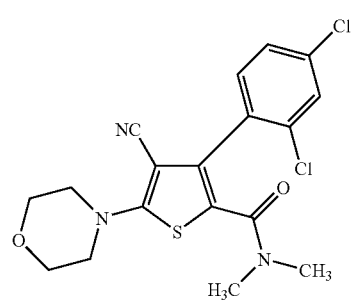
-continued
37
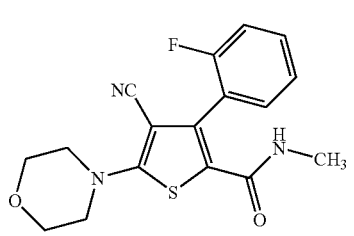
38
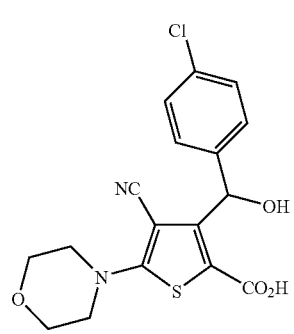
39
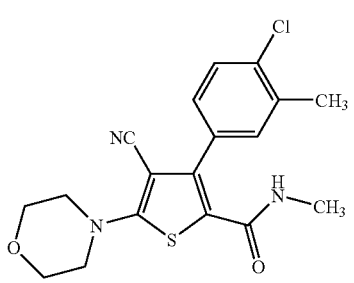
40
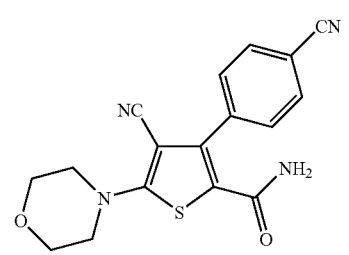
41
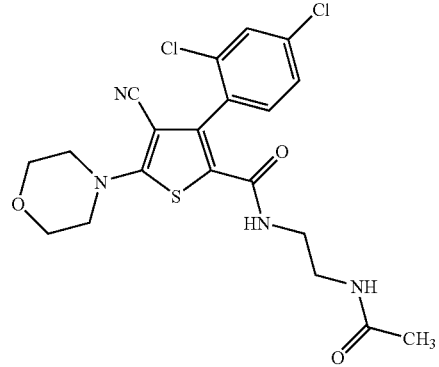

-continued

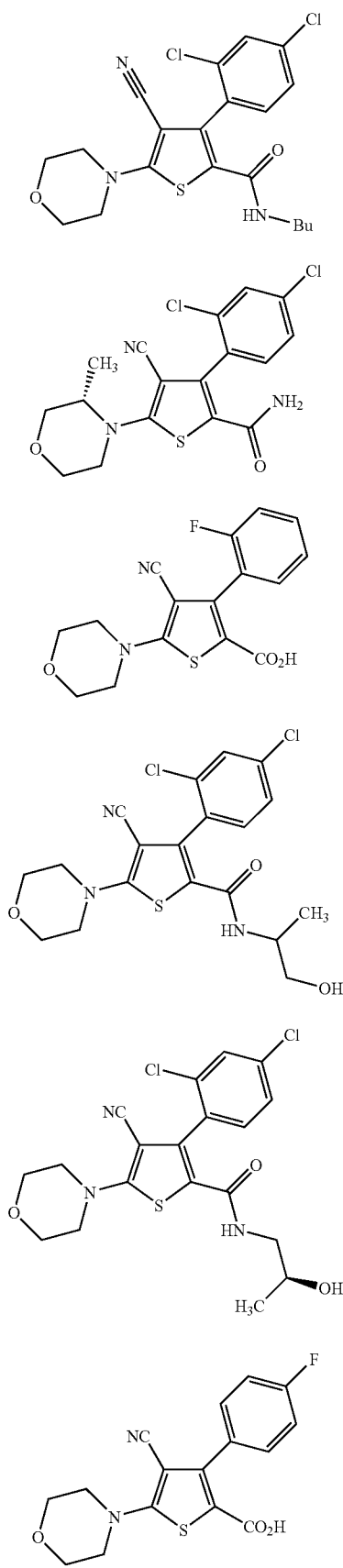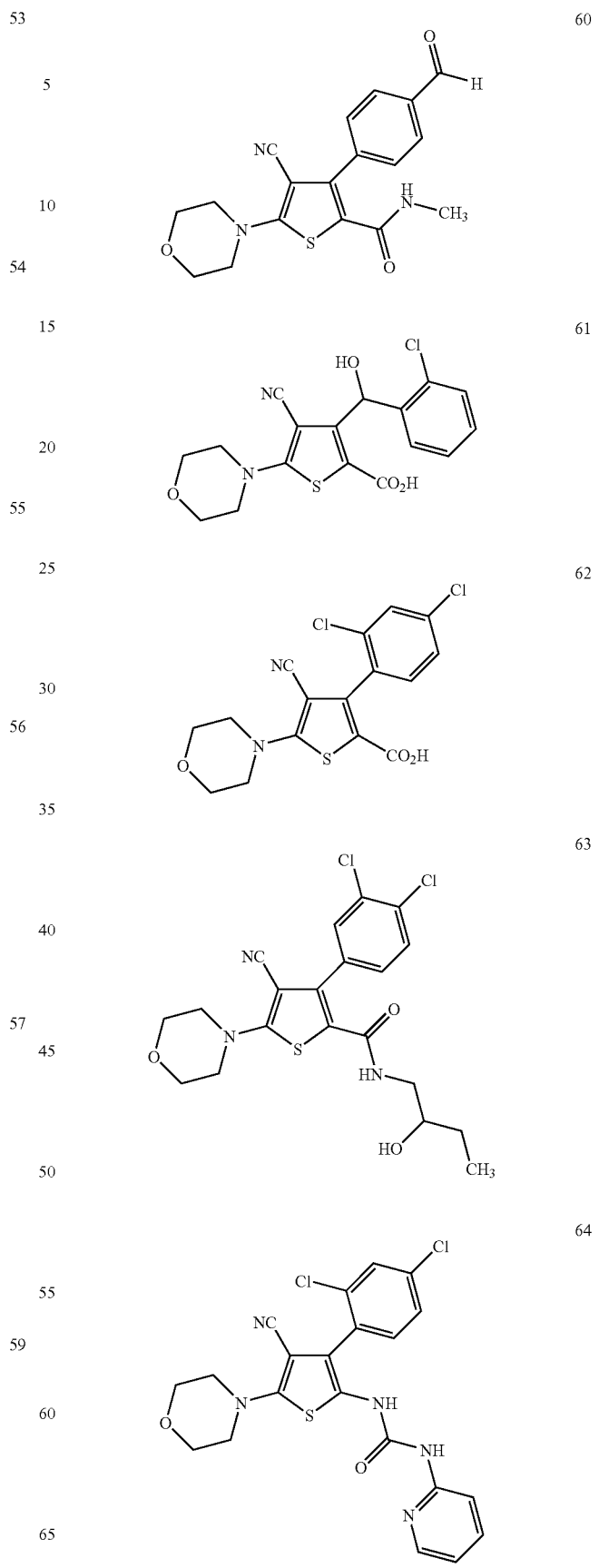

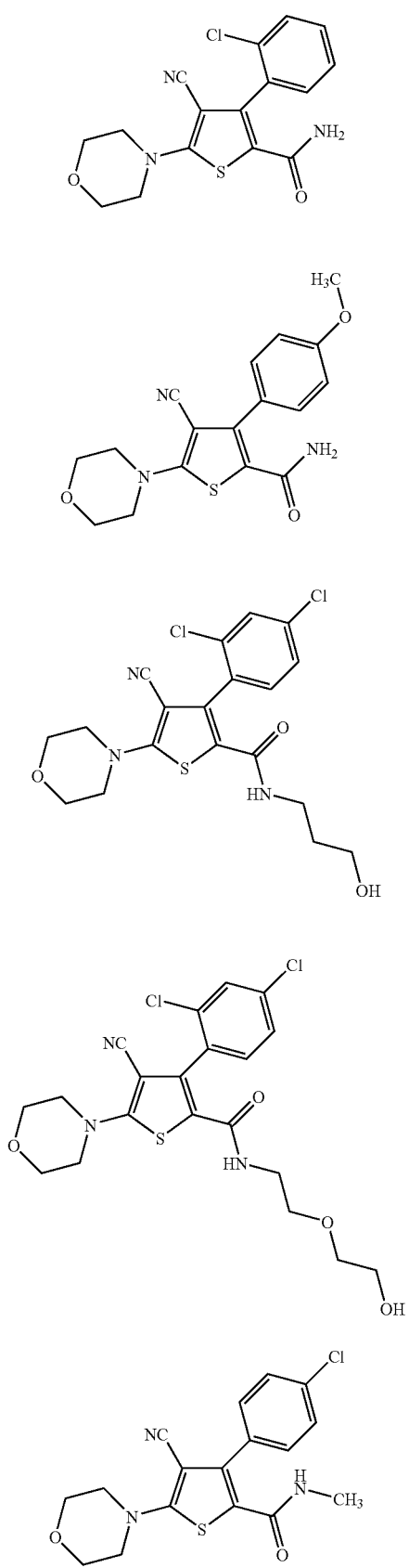
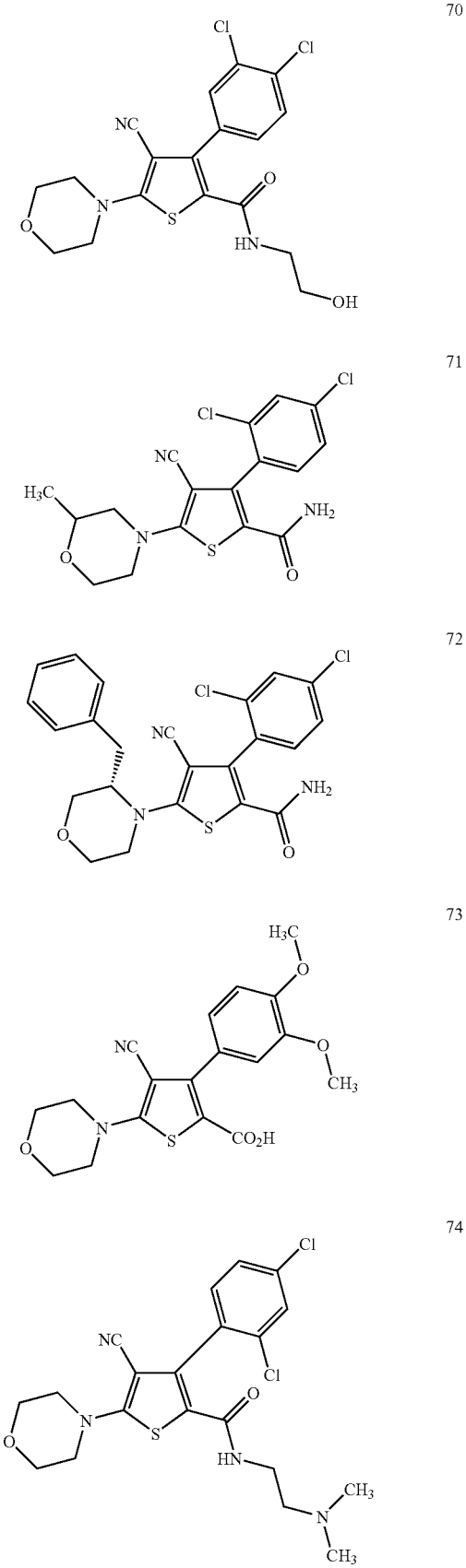

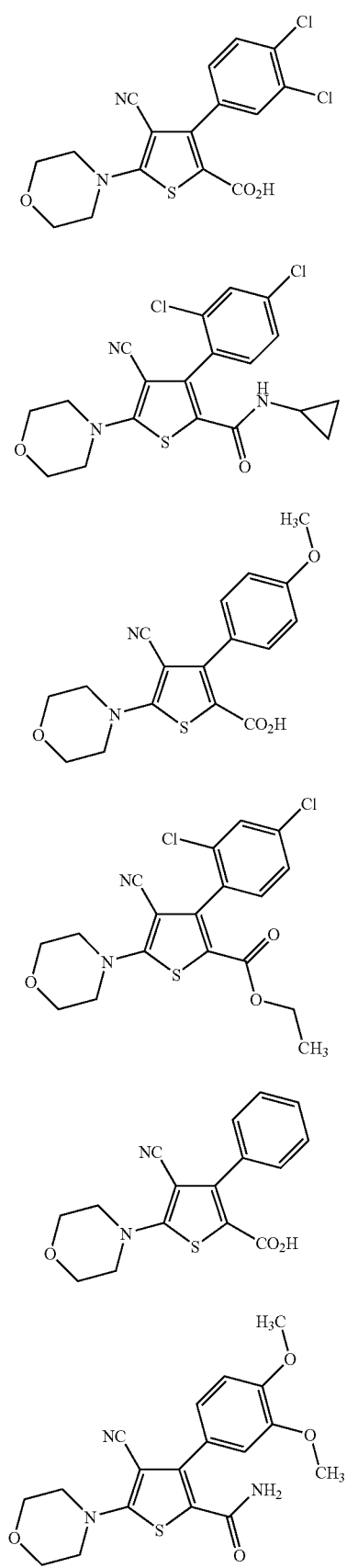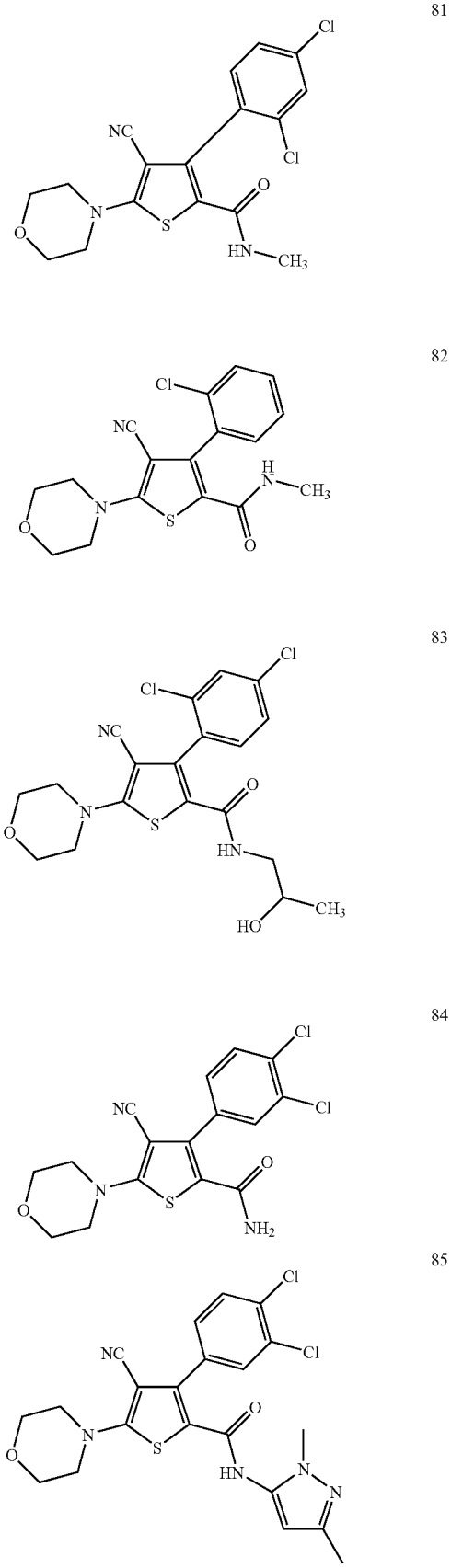

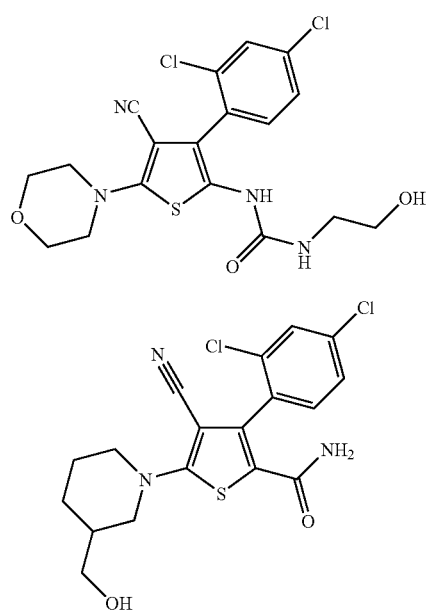
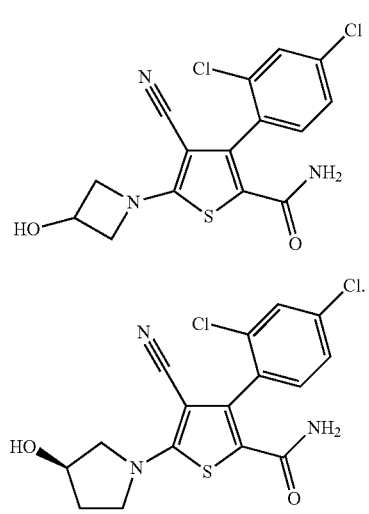
11. A composition comprising a compound of claim 1 and a pharmaceutically acceptable carrier.
* * * * *